US006888032B2

(12) United States Patent
Buchwald et al.

(10) Patent No.: US 6,888,032 B2
(45) Date of Patent: May 3, 2005

(54) COPPER-CATALYZED FORMATION OF CARBON-HETEROATOM AND CARBON-CARBON BONDS

(75) Inventors: Stephen L. Buchwald, Newton, MA (US); Artis Klapars, Scotch Plains, NJ (US); Fuk Y. Kwong, Sai Wan Ho (CN); Eric R. Streiter, Cambridge, MA (US); Jacopo Zanon, Venice (IT)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 10/631,480

(22) Filed: Jul. 31, 2003

(65) Prior Publication Data

US 2004/0138468 A1 Jul. 15, 2004

Related U.S. Application Data

(60) Provisional application No. 60/400,902, filed on Aug. 2, 2002.

(51) Int. Cl.[7] ............................................. C07C 319/04

(52) U.S. Cl. ........................................... 568/38; 58/59

(58) Field of Search ........................... 568/38, 58, 59

(56) References Cited

U.S. PATENT DOCUMENTS

| | | | |
|---|---|---|---|
| 2,490,813 A | 12/1949 | Hughes et al. ............... | 260/581 |
| 4,259,519 A | 3/1981 | Stille ........................... | 560/193 |
| 4,423,234 A | 12/1983 | Plummer et al. ............. | 549/80 |
| 4,642,374 A | 2/1987 | Lucy et al. ................... | 560/204 |
| 4,659,803 A | 4/1987 | Bartmann et al. ........... | 528/491 |
| 4,734,521 A | 3/1988 | Frazier ........................ | 560/204 |
| 4,764,625 A | 8/1988 | Turner et al. ................ | 548/442 |
| 4,983,774 A | 1/1991 | Cahiez et al. ................ | 568/319 |
| 5,159,115 A | 10/1992 | Pappas et al. ............... | 564/401 |
| 5,300,675 A | 4/1994 | Elango ......................... | 560/55 |
| 5,405,981 A | 4/1995 | Lipshutz ...................... | 556/112 |
| 5,705,697 A | 1/1998 | Goodbrand et al. ........ | 564/405 |
| 5,808,055 A | 9/1998 | Nakajima et al. ........... | 540/544 |
| 5,908,939 A | 6/1999 | Baak et al. .................. | 549/407 |
| 6,180,836 B1 | 1/2001 | Cheng et al. ................ | 568/803 |
| 6,239,312 B1 | 5/2001 | Villanti et al. ............... | 562/526 |
| 6,271,419 B1 | 8/2001 | Desmurs et al. ............. | 564/82 |
| 6,399,820 B2 | 6/2002 | Desmurs et al. ............. | 562/834 |
| 6,541,639 B2 | 4/2003 | Zhou et al. ................... | 546/249 |
| 6,610,871 B1 | 8/2003 | Duebner et al. .............. | 556/28 |
| 2001/0020113 A1 | 9/2001 | Desmurs et al. ............. | 562/834 |
| 2001/0047013 A1 | 11/2001 | Lang et al. ................... | 514/318 |
| 2002/0010347 A1 | 1/2002 | Bonrath et al. .............. | 549/411 |
| 2003/0045740 A1 | 3/2003 | Douglas et al. .............. | 558/335 |
| 2003/0065187 A1 | 4/2003 | Buchwald et al. ........... | 564/192 |
| 2004/0019216 A1 | 1/2004 | Buchwald et al. ........... | 548/469 |

FOREIGN PATENT DOCUMENTS

RU          2148613          5/2000

OTHER PUBLICATIONS

U.S. Provisional Appl. No. 60/220,932, filed Jul. 26, 2000, Zhou et al.

Arai et al.; "The Ullmann Condensation Reaction of Haloanthraquinone Derivatives With Amines in Aprotic Solvents. IV. Kinetic Studies of the Condensation with Ethylenediamines", Bulletin of the Chemical Society of Japan 52(6): 1731–1734, (1979).

Avendano et al.; "The Problem of the Existence of C(Ar)– H . . . N Intramolecular Hydrogen Bonds in a Family of 9–azaphenyl–9H–carbazoles", J. Chem. Soc. Perkin Trans. 2, pp. 1547–1555, (1993).

Beletskaya et al, "Pd– and Cu–catalyzed selective Arylation of Benzotriazole" Tetrahedron Letters, vol. 39, pp. 5617–5620, (1998).

Duplantier et al.; "7–Oxo–4,5,6,7–tetrahydro–1H–pyrazolo [3,4–c] pyridines as Novel Inhibitors of Human Eosinophil Phosphodiesterase", J. Med. Chem. 41: 2268–2277, (1998).

Fabian, "Kinetics and Mechanism of Complex–formation Reactions of Ammonia and Methylamine with Copper (II) Complexes in Aqueous Solution", J. Chem. Soc. Dalton Trans. 1994.

Faith, Keyes, and Clarks's Industrial Chemicals, 4th ed., pges 674–678, John Wiley & Sons (1975).

(Continued)

Primary Examiner—Taofiq Solola
(74) Attorney, Agent, or Firm—Dana M. Gordon; Foley Hoag, LLP

(57) ABSTRACT

One aspect of the present invention relates to copper-catalyzed carbon-heteroatom and carbon-carbon bond-forming methods. In certain embodiments, the present invention relates to copper-catalyzed methods of forming a carbon-sulfur bond between the sulfur atom of a thiol moiety and the activated carbon of an aryl, heteroaryl, or vinyl halide or sulfonate. In other embodiments, the present invention relates to copper(II)-catalyzed methods of forming a carbon-nitrogen bond between the nitrogen atom of an amide and the activated carbon of an aryl, heteroaryl, or vinyl halide or sulfonate. In certain embodiments, the present invention relates to copper-catalyzed methods of forming a carbon-carbon bond between the carbon atom of cyanide ion and the activated carbon of an aryl, heteroaryl, or vinyl halide or sulfonate. In another embodiment, the present invention relates to a copper-catalyzed method of transforming an aryl, heteroaryl, or vinyl chloride or bromide into the corresponding aryl, heteroaryl, or vinyl iodide. Yet another embodient of the present invention relates to a tandem method, which may be practiced in a single reaction vessel, wherein the first step of the method involves the copper-catalyzed formation of an aryl, heteroaryl, or vinyl iodide from the corresponding aryl, heteroaryl, or vinyl chloride or bromide; and the second step of the method involves the copper-catalyzed formation of an aryl, heteroaryl, or vinyl nitrile, amide or sulfide from the aryl, heteroaryl, or vinyl iodide formed in the first step.

25 Claims, 16 Drawing Sheets

OTHER PUBLICATIONS

Goodbrand and Hu; "Ligand–Accelerated Catalysis of the Ullmann Condensation: application to Hole Conducting Triarylamines", J. Org. Chem. 64: 670–674, (1999).

Greiner Alfred; "An Improvement of the N–Arylation of Amides; Application to the Synthesis of Substituted 3–(N–Acetyl–N–phenylamino)–pyridines", Synthesis No. 4: 312–313, (Apr. 1989).

Gauthier and Frechet; "Phase–Transfer Catalysis in the Ullmann Synthesis of Substituted Triphenylamines", Synthesis, No. 4: 383–385, (Apr. 1987).

Gujadhur et al.; "Formation of Aryl–nitrogen Bonds Using a Soluble Copper (I) Catalyst", Tetrahedron Letters 42: 4791–4793, (2001).

International Search Report Completed on Jul. 11, 2002 and Mailed on Sep. 12, 2002.

Ito et al.; "Synthesis of Oligo (m–aniline)", Tetrahedron Letters 36(48): 8809–8812, (1995).

Joyeau et al.; "Synthesis of Benzocarbacephem and Benzocarbacephem Derivatives by Copper–Promoted Intramolecular Aromatic Substitution", J. Chem. Soc. Perkin Trans. I, pp. 1899–1907, (1987).

Kametari et al.; "Studies on the Syntheses of Heterocyclic Compounds. Part 865.1/$_7$A Novel Synthesis of Indole Derivates by Intramolecular Nucleophilic Aromatic Substitution", J.C. S. Perkin I, pp. 290–294, (1981).

Kang et al.; "Copper–Catalyzed N–Arylation of Amines with Hypervalent Iodonium Salts", Synlett No. 7: 1022–1024, (2000).

Kato et al.; "Water–Soluble Receptors For Cyclic–AMP and Their Use for Evaluation Phosphate–Guanidinium Interactions", J. Am. Chem. Soc. 116: 3279–3284, (1994).

Kiyomori et al, "An Efficient Copper–Catalyzed Coupling of Aryl Halides with Imidazoles" Tetrahedron Letters, vol. 40, pp. 2657–2660 (1999).

Kondratov and Shein; "Nucleophilic Substitution In The Aromatic Series.L.V. Reaction of O–Nitrochlorobenzene with Ammonia in the Presence of Copper Compounds", Zhumal Organicheskoi Khimii, vo. 15(11): 2387–2390 (1979) (as abstracted by CAPLVS).

Lexy and Kauffmann; "Synthese, Lithiierung und Oxidative Kupplung von 1,3,5– Tri(1–Pyrazolyl) benzol", Chem. Ber. 113:2755–2759 (1980).

Lindley James; "Copper Assisted Nucleophilic Substitution of Aryl Halogen", Tetrahedron 40(9): 1433–1456, (1984).

Murakami et al.; Fisher Indolization of Ethyl Pyruvate 2–[2–(Trifluoromethyl) Phenyl]– Phenylhydrazone and New Insight Into the Mechanism of the Goldberg Reaction. (Fisher Indolization and Its Related Compounds. XXVI [1]), Chem. Pharm. Bull. 43(8): 1281–1286 (1995).

Palkowitz et al.; "Discovery and Synthesis of [6–Hydroxy–3–[4–[2–(1–piperidinyl)ethoxy]phenoxy]–2–(4–Hydroxyphenyl)]benzo[b]thiophene: A Novel, Highly Potent, Selective Estrogen Receptor Modulator", Journal od Medicinal Chemistry 40(10): 1407–1416, (May 9, 1997).

Renger Bernd; "Direkte N–Arylierung von Amiden: Eine Verbesserung der Goldberg–Reaktion", Synthesis, No. 9: 856–860, (1985).

Sawyer et al.; "Synthesis of Diaryl Ethers, Diaryl Thioethers, and Diarylamines Mediated by Potassium Fluoride–Alumina and 18–Crown–6: Expansion of Scope and Utility [1]", J. Org. Chem. 63: 6338–6343, (1988).

Smith III and Sawyer; "A Novel and Selective Method for the N–Arylation of Indoles Mediated by $KF/Al_2O_3$", Tetrahedron Letters 37(3): 299–302, (1996).

Smith III and Sawyer; "An $S_NAr$–Based Preparation of 1–(2–, 3–, and 4–Pyridyl) Indoles Using Potassium Fluoride/Alumina", Heterocycles51(1): 157–160, (1999).

Steglich and Hoefle, "Hypemucleophilic Acylation Catalysts. II. Simple Preparation Of Acyl–5–Oxazolinones From 5–Acyloxyoxazoles" Tetrahedron Letters, vol. 54, pp. 4727–4730 (1970). CAPLUS abstract.

Straumanis and Circulus,"New Complex Compounds of Mercury And Copper Halides With Aliphatic Amines", Z. Anorg. Allgem. Chem., vol. 230, pp. 65–87 (1936). CAPLUS abstract.

Sugahara and Ukita, "A Facile Copper–Catalyzed Ullmann Condensation: N–Arylation of Heterocyclic Compounds Containing an —NHCO— Moiety", Chem. Pharm. Bull. 45(4): 719–721 (1977).

Tokmakov and Grandberg; "Rearrangement of 1–Arylindoles to 5H–Dibenz[b, f]azepines", Tetrahedron 51(7): 2091–2098, (1995).

Unangst et al.; "Synthesis of Novel 1–Phenyl–1H–Indole–2–Carboxylic Acids. I Utilization Of Ullmann and Dieckmann Reactions for the Preparation of 3–Hydroxy, 3–Alkoxy, and 3–Alkyl Derivatives", Journal of Heterocyclic Chemistry, 24(3): 811–815, (May–Jun. 1987).

Vainshtein and Tomilenko; "Exchange of Halogens in Halobenzenes in a Reaction with Ammonia with Participation of Copper", Zhumal Vsesoyuznogo Khimicheskogo Obshchestva im. D.I. Mendeleeva, 13(6): 709–710, (1968) (as abstracted by CAPLVS).

Vedejs E.; "Substituted Isoquinolines by Noyori Transfer Hydrogenation: Enantioselective Synthesis of Chiral Diamines Containing an aniline Subunit", J. Org. Chem. 64: 6724–6729, (1999).

Yamamoto and Kurata; "Ullmann Condensation Using Copper or Copper Oxide as the Reactant. Arylation of Active Hydrogen Compounds (imides, amides, amines, phenol, benzoic acid, and phenylacetylene)", Can. J. Chem. 61: 86–91, (1983).

Figure 2

| Entry | ArI | RSH | Product | % yield[a] |
|---|---|---|---|---|
| | | 5 mol% CuI | | |
| | ArI + HS-Ar | 2 eq. HOCH₂CH₂OH → ArSAr | | |
| | 1.0 mmol  1.0 mmol | 2 eq. K₂CO₃ | | |
| | | iPrOH, 80 °C, 18-22 h | | |
| 1 | 2-iodobenzyl alcohol | 4-methoxybenzenethiol | product | 89 |
| 2 | 3,5-dimethyliodobenzene | 2-chlorobenzenethiol | product | 87 |
| 3 | 3-methoxyiodobenzene | 2-isopropylbenzenethiol | product | 93 |
| 4 | 2-iodotoluene | 2-isopropylbenzenethiol | product | 88 |
| 5 | 3,5-dimethyliodobenzene | methyl 2-mercaptobenzoate | product | 86[c] |
| 6 | 2-iodoaniline | 4-tert-butylbenzenethiol | product | 90 |
| 7 | 2-isopropyliodobenzene | 4-methoxybenzenethiol | product | 94[d] |
| 8 | 2-isopropyliodobenzene | 2-isopropylbenzenethiol | product | 91[d] |
| 9 | 3-iodopyridine | 4-acetamidobenzenethiol | product | 83 |
| 10 | 5-iodoindole | 4-methoxybenzenethiol | product | 90 |
| 11 | 3-methoxyiodobenzene | 2-mercaptopyridine | product | 19[b] |

[a] Isolated yield. [b] GC yield. [c] DME was used as solvent instead of 2-propanol/ethylene glycol.
[d] With 20 mol% CuI, 1.2 eq. ArSH, tert-Amyl alcohol as solvent, 100 °C, 20 h.

Figure 3
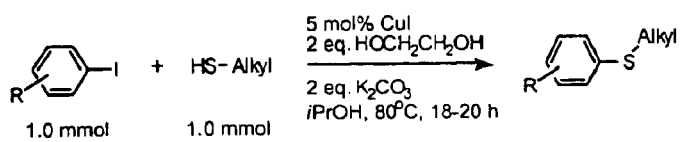
| Entry | Arl | RSH | Product | % yield[a] |
|---|---|---|---|---|
| 1 |  | 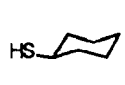 | 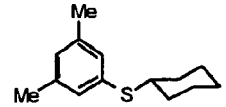 | 72 |
| 2 |  | 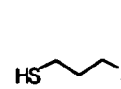 | 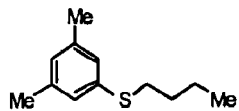 | 95 |
| 3 | 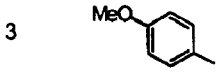 | 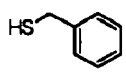 | 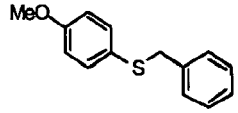 | 90 |
| 4 | 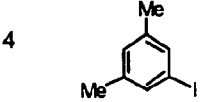 | 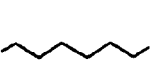 | 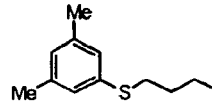 | 92 |
[a] Isolated yield.

| Entry | Cu cat. | % Conv | % Yield[a] |
|---|---|---|---|
| 1 | CuI | 94 | 93 |
| 2 | CuCl | 99 | 99 |
| 3 | CuBr | 99 | 99 (94 iso.) |
| 4 | CuOAc | 96 | 96 |
| 5 | $CuCl_2 \cdot H_2O$ | 97 | 96 |
| 6 | $CuBr_2$ | 99 | 99 |
| 7 | $CuF_2$ | 99 | 99 |
| 8 | $Cu(OAc)_2$ | 99 | 99 |
| 9 | $Cu(acac)_2$ | 92 | 92 |
| 10 | $Cu(OTf)_2$ | 79 | 78 |
| 11 | $CuSO_4 \cdot 5H_2O$ | 63 | 59 |

[a] GC yield was reported.

| Entry | Base | % Conv | % Yield[a] |
|---|---|---|---|
| 1 | K₃PO₄ | 96 | 94 |
| 2 | K₂CO₃ | 98 | 98 |
| 3 | Cs₂CO₃ | 60 | 47 |
| 4 | Na₂CO₃ | 91 | 90 |
| 5 | NaOt-Bu | 96 | 95 |
| 6 | DBU | 72 | 70 |
| 7 | Et₃N | 68 | 64 |
| 8 | pyridine | 20 | 13 |
| 9 | DBU (slow addition in 4 h) | 84 | 80 |
| 10 | Et₃N (slow addition in 4 h) | 61 | 55 |

[a] GC yield was reported.

Figure 7
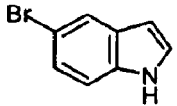
| Entry | Aryl Bromide | Aryl Iodide | Yield |
|---|---|---|---|
| 1 | 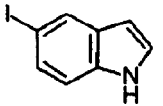 | 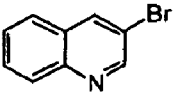 | 98% |
| 2 | 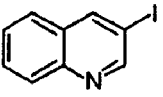 | 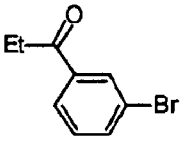 | 97% |
| 3 | 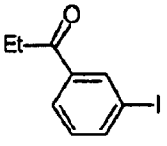 | 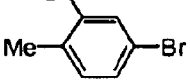 | 98% |
| 4 | 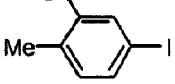 | 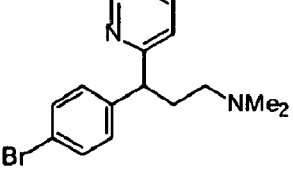 | 95% |
| 5 | 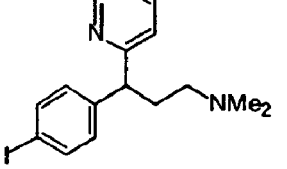 | 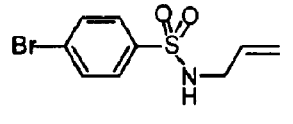 | 100% |
| 6 | 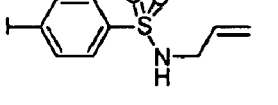 | 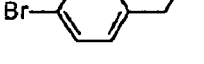 | 96% |
| 7 | 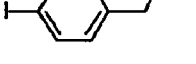 | 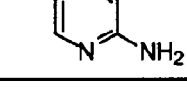 | 97% |
| 8 | 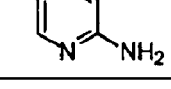 | | 95% |

| Entry | Ligand | Yield of 5-Iodo-*m*-xylene | Entry | Ligand | Yield of 5-Iodo-*m*-xylene |
|---|---|---|---|---|---|
| 1 | MeHN──⟨cyclohexane⟩──NHMe | 95% | 8 | H₂N–C(Me)(Me)–NH₂ | 22% |
| 2 | MeHN⌒NHMe | 70% | 9 | H₂N–CH(Ph)–CH(Ph)–NH₂ | 14% |
| 3 | MeHN⌒NH₂ | 71% | 10 | H₂N⌒NH⌒NH₂ | 30% |
| 4 | EtHN⌒NH₂ | 60% | | | |
| 5 | nBuHN⌒NH₂ | 71% | 11 | H₂N⌒⌒NH₂ | 52% |
| 6 | Me₂N⌒NH₂ | 20% | 12 | MeHN⌒⌒NHMe | 8% |
| 7 | Me₂N⌒NHMe | 18% | 13 | MeHN⌒OH | 1% |

| Entry | Solvent | % Conv | % Yield[a] |
|---|---|---|---|
| 1 | iPrOH | 81 | 80 |
| 2[b] | iPrOH | 98 | 96 |
| 3 | DMF | 58 | 55 |
| 4[b] | DMF | 67 | 66 |
| 5 | DME | 86 | 86 |
| 6[b] | DME | 60 | 49 |
| 7 | Toluene | 35 | Trace |
| 8[b] | Toluene | 37 | Trace |
| 9 | Dioxane | 55 | 39 |
| 10[b] | Dioxane | 63 | 53 |

[a] GC yield was reported. [b] With 2 eq. of ethylene glycol.

Copper-catalyzed conversion of aryl bromides into aryl iodides.[a]

[a] Isolated yields (average of two runs); >95% purity as determined by GC and $^1$H NMR. [b] With 1.0 equiv of hexamethyldisilazane. [c] Performed in 4:1 m-xylene/diglyme solvent mixture at 130 °C for 22 h. [d] Performed in n-pentanol 130 °C for 40 h. [e] With 10 mol% of ligand 3 in n-pentanol at 130 °C for 22 h.

Conversion of 5-bromo-*m*-xylene into 5-iodo-*m*-xylene using NaI or KI in *n*-BuOH or DMF. Performed with 5.0 mol% CuI, 10 mol% *trans-N,N'*-Dimethyl-1,2-cyclohexanediamine, 1.0 equiv of aryl halide, and 2.0 equiv of the halide salt at 110 °C.

Conversion of 5-bromo-*m*-xylene into 5-iodo-*m*-xylene using NaI or TBAI (tetrabutylammonium iodide); and the reverse reaction using NaBr or TBAB (tetrabutylammonium bromide). Performed in DMF at 110 °C with 5.0 mol% CuI, 10 mol% *trans-N,N'*-Dimethyl-1,2-cyclohexanediamine, 1.0 equiv of aryl halide, and 1.0 equiv of the halide salt.

Copper-catalyzed cyanation of 5-bromo-*m*-xylene. Performed in toluene at 110 °C with 10 mol% of CuI, 1.0 equiv of ligand *N,N'*-dimethyl-1,2-diaminoethylene, 20 mol% of KI, and 1.2 equiv of NaCN.

Figure 15

| Entry | Ar-Br | Ar-CN | Temp.,°C | Yield, %[a] |
|---|---|---|---|---|
| 1 | 3,5-dimethylphenyl-Br | 3,5-dimethylphenyl-CN | 110 | 90 |
| 2 | 3,4-dimethoxyphenyl-Br | 3,4-dimethoxyphenyl-CN | 110 | 91 |
| 3 | 1-bromonaphthalene | 1-cyanonaphthalene | 130 | 90 |
| 4 | 2-bromobiphenyl | 2-cyanobiphenyl | 130 | 98 |
| 5 | 4-(hydroxymethyl)phenyl-Br | 4-(hydroxymethyl)phenyl-CN | 110 | 80[b] |
| 6 | ethyl 4-bromophenylacetate | ethyl 4-cyanophenylacetate | 130 | 70 |
| 7 | 2-bromo-N,N-dimethylaniline | 2-cyano-N,N-dimethylaniline | 130 | 85 |
| 8 | 4-bromo-2-fluoroacetanilide | 4-cyano-2-fluoroacetanilide | 110 | 90 |
| 9 | 2-bromo-4-methylacetanilide | 2-cyano-4-methylacetanilide | 130 | 70 |

Reaction conditions: 10 mol% CuI, 20 mol% KI, 1.0 equiv ligand 1, 1.2 equiv NaCN, Toluene, 110–130 °C, 24 h. Ligand 1 = Me(H)N-CH₂CH₂-N(H)Me.

[a] Isolated yields (average of two runs); >95% purity as determined by GC and ¹H NMR; all reactions proceeded to >99% conversion of aryl bromide except for entry 7 (98% conversion). [b] Performed for 20 h.

[a] Isolated yields (average of two runs); >95% purity as determined by GC and $^1$H NMR; all reactions proceeded to >99% conversion of aryl bromide. [b] Performed for 20 h.

US 6,888,032 B2

COPPER-CATALYZED FORMATION OF CARBON-HETEROATOM AND CARBON-CARBON BONDS

RELATED APPLICATIONS

This application claims the benefit of priority to U.S. Provisional Application Ser. No. 60/400,902, filed Aug. 2, 2002; the entirety of which is hereby incorporated by reference.

GOVERNMENT SUPPORT

This invention was made with support from the National Institutes of Health (grant number RO1-GM58160); therefore, the government has certain rights in the invention.

BACKGROUND OF THE INVENTION

Palladium-catalyzed methods for the formation of carbon-heteroatom bonds, e.g., carbon-nitrogen bonds, are now widely-exploited in the synthesis of pharmaceuticals, materials with important electronic properties, and ligands for early metal catalysts. See, e.g., Stille, J. K. Angew. Chem., Int. Ed. Engl., 25:508–524 (1986); Miyaura, N. et al., Chem. Rev., 95:2457–2483 (1995); Negishi, E. Acc. Chem. Res., 15:340–348 (1982). Likewise, the palladium-catalyzed coupling to form carbon-carbon bonds between an aryl or vinyl halide and a carbon nucleophile is widely used. However, the ever-increasing cost of palladium detracts from the allure of these powerful methods. Consequently, a need exists for general and efficient catalytic methods for forming carbon-heteroatom and carbon-carbon bonds based on a catalyst that does not comprise a rare, costly transition metal, such as palladium. Likewise, a need also exists for a general and efficient catalytic method for forming carbon-carbon bonds between an aryl or vinyl halide and a carbon nucleophile, based on a catalyst that does not comprise a rare, costly transition metal, such as palladium. Notably, in 1998, bulk palladium sold on the international metal market for roughly five-thousand times the cost of bulk copper. Therefore, based solely on catalyst cost, the aforementioned transformations would be orders of magnitude more appealing if they could be achieved with catalysts comprising copper rather than palladium.

Copper-Catalyzed Carbon-Sulfur Bond Formation

Aryl sulfides are an important class of compounds for biological, material and pharmaceutical applications. Liu, G.; Link, J. T.; Pei, Z.; Reilly, E. B.; Leitza, S.; Nguyen, B.; Marsh, K. C.; Okasinski, G. F.; von Geldern, T. W.; Ormes, M.; Fowler, K.; Gallatin, M. J. Med. Chem. 2000, 43, 4025–4040; Beard, R. L.; Colon, D. F.; Song, T. K.; Davies, P. J. A.; Kochhar, D. M.; Chandraratna, R. A. S. J. Med. Chem. 1996, 39, 3556–3563; Nagai, Y.; Irie, A.; Nakamura, H.; Hino, K.; Uno, H.; Nishimura, H. J. Med. Chem. 1982, 25, 1065–1070; Pinchart, A.; Dallaire, C.; Gingras, M. Tetrahedron Lett. 1998, 39, 543–546; Hay, A. S.; Ding, Y. Macromolecules 1997, 30, 1849–1850; Hay, A. S.; Wang, Z. Y.; Tsuchida, E.; Yamamoto, K.; Oyaizu, K.; Suzuki, F. Macromolecules 1995, 28, 409–415; Miki, H.; Nakahama, T.; Yokoyama, S.; Mashiko, S. U.S. Patent Application Publication US 20020072583 A1; Wang, Y.; Chackalamannil, S.; Chang, W.; Greenlee, W.; Ruperto, V.; Duffy, R. A.; McQuade, R.; Lachowicz, J. E. Bioorg. Med. Chem. Lett. 2001, 11, 891–894; Bonnet, B.; Soullez, D.; Girault, S.; Maes, L.; Landry, V.; Davioud-Charvet, E.; Sergheraert, C. Bioorg. Med. Chem. 2000, 8, 95–103; Sawyer, J. S.; Schmittling, E. A.; Palkowitz, J. A.; Smith III, W. J. J. Org. Chem. 1998, 63, 6338–6343. Traditional transition metal catalyzed methods for the construction of aryl-sulfur bonds usually require harsh reaction conditions; for example, the coupling of aryl halides with arenethiolate anion using Ni complexes requires high temperature (~200° C.) and a strong base (NaH); besides, side products are commonly observed. Diederich, F.; Stang, P. J. Metal-catalyzed Cross-Coupling Reactions, Wiley-VCH 1998; Hassan, J.; Sévignon, M.; Gozzi, C.; Schulz, E.; Lemaire, M. Chem. Rev. 2002, 102, 1359–1470; Cristau, H. J.; Chabaud, B.; Chéne, A.; Christol, H. Synthesis 1981, 892–894.; Takagi, K. Chem. Lett. 1987, 2221–2224. Since Migita's report on palladium-catalyzed diaryl sulfide formation, only a few reports have appeared using palladium complexes as the catalysts, and the substrate scope is narrow. Migita, T.; Shimizu, T.; Asami, Y.; Shiobara, J.-i.; Kato, Y.; Kosugi, M. Bull. Chem. Soc. Jpn. 1980, 53, 1385–1389; Zheng, N.; McWilliams, J. C.; Fleitz, F. J.; Armstrong III, J. D.; Volante, R. P. J. Org. Chem. 1998, 63, 9606–9607; Harr, M. S.; Presley, A. L.; Thorarensen, A. Synlett. 1999, 1579–1581; Schopfer, U.; Schlapbach, A. Tetrahedron 2001, 57, 3069–3073; Li, G. Y. Angew. Chem. Int. Ed. 2001, 40, 1513–1516; Li, G. Y. J. Org. Chem. 2002, 67, 3643–3650; Ciattini, P. G.; Morera, E.; Ortar, G. Tetrahedron Lett. 1995, 36, 4133–4136; Ishiyama, T.; Mori, M.; Suzuki, A.; Miyaura, N. J. Organomet. Chem. 1996, 525, 225–23; Wendeborn, S.; Berteina, S.; Brill, W. K.-D.; Mesmaeker, A. D. Synlett. 1998, 671–675. Catalyst systems such as $Pd(OAc)_2$/Tol-BINAP or $Pd_2(dba)_3$/DPPF allow to couple aryl triflates or aryl iodides only with alkyl thiols and not with aromatic thiols. In addition, they often require a strong base, e.g., NaOt-Bu, which is not compatible with base-sensitive functional groups.

An alternative coupling methodology, copper-catalyzed Ullmann-type coupling, is attractive for large and/or industrial-scale applications. Lindley, J. Tetrahedron 1984, 40, 1433–1456. However, a mild Cu-catalyzed C—S bond formation reaction compatible with a broad range of functional groups remains elusive. Palomo, C.; Oiarbide, M.; López, R.; Gómez-Bengoa, E. Tetrahedron Lett. 2000, 41, 1283–1286; Herradura, P. S.; Pendola, K. A.; Guy, R. K. Org. Lett. 2000, 2, 2019–2012; Kalinin, A. V.; Bower, J. F.; Riebel, P.; Snieckus, V. J. Org. Chem. 1999, 64, 2986–2987.

Copper-Catalyzed Cyanation of Aryl Halides

Aromatic nitrites are very important materials because of their wide application from small laboratory scale to industrial purposes. Since the first cyanation reaction of an aromatic halide was reported, various methods have been developed for the synthesis of aromatic nitrites involving the use of different metals in presence of cyanide sources. Pongratz, A. Monatsh. Chem. 1927, 48, 585; Pongratz, A. Monatsh. Chem. 1929, 52, 7; Ellis, G. P., Rommney-Alexander T. M. Chem. Rev. 1987, 87, 779.

The most convenient cyanation method is the stoichiometric reaction of aryl halides with copper(I) cyanide at high temperature (typically over 150° C.). Aromatic iodides, bromides, chlorides and fluorides are converted by copper(I) cyanide into the nitrites, the iodides being the most reactive. The difference in reactivity between aryl iodides and chlorides is sufficient to permit preferential cyanation of the iodide in presence of a chloride. Suzuki, H.; Hanafusa, T. Synthesis 1974, 53. Unfortunately, the product isolation is very troublesome due to the formation of different copper species in the course of the reaction.

Palladium-catalyzed displacement of aryl halides and triflates with cyanide ion to afford the corresponding aromatic nitrites has been reported as an alternative to the copper-catalyzed process. Sundermeier, M.; Zapf, A.; Beller, M.; Sans, J. *Tetrahedron Lett.* 2001, 42, 6707; Hioki, H.; Nakaoka, R.; Maruyama, A.; Kodama, M. *J. Chem. Soc., Perkin Trans. 1* 2001, 3265; Jiang, B.; Kan, Y.; Zhang A. *Tetrahedron* 2001, 57, 1581. Jin F.; Confalone, P. N.; *Tetrahedron Lett.* 2000, 41, 3271; Maligres, P. E.; Waters M. S.; Fleitz, F. Askin, D. *Tetrahedron Lett.* 1999, 8193; Sakamoto, T.; Oshwa, K. *J. Chem. Soc. Perkin Trans. 1* 1999, 2323; Anderson, B. A.; Bell, E. C.; Ginah, F. O.; Harn, N. K.; Pagh, L. M.; Wepspiec, J. P. *J. Org. Chem.* 1998, 63, 8224. Nickel complexes can also catalyze the cyanation of aromatic halides or heteroaromatic halides into the corresponding aromatic cyanides under the influence of an alkali metal cyanide. Duphar International Research B. V, Nickel catalyst for the cyanation of aromatic halides, European Patent Application 0 613 719 A1, Jul. 9, 1994; Occidental Chemical Corporation, Cyanation of haloaromatics utilizing catalyst generated in situ starting with $NiCl_2$ or $NiCl_2.6H_2O$, European Patent Application 0 384 392 A1; Sakakibara, Y.; Ido, Y.; Sasaki, K.Saki, M.; Uchino, M. *Bull Chem. Soc. Jpn.* 1993, 66, 2776–78; H. Lundbeck A/S, Method for the preparation of Citalopram by nickel-catalyzed cyanation of halo precursors, GB Patent 2 354 240 A1, Mar. 21, 2001; Teijin Ltd., Japan Preparation of 5-(3-cyanophenyl)-3-formylbenzoic acids as intermediates for factor Xa inhibitors. JP Patent 2001335551 A2, Dec. 4, 2001; Cassar, L.; Foa, M.; Montanari, F.; Marinelli, G. P. *J. Organomet. Chem.* 1979, 173, 335–9; Cassar, L. *J. Organomet. Chem.* 1973, 54, C57–C58. Alternative methods involving phase transfer catalysts or the presence of other activating agents have been recently reported. Yu-Qing, C.; Bao-Hua, C.; Ben-Gao, P. *Synth. Commun.* 2001, 31, 2203; Tamon, O.; Jitsuo, K.; Toyooka, Y. *Chem. Lett.* 1998, 5, 425; Aventis Cropscience GMBH, Process for the preparation of 2-cyanopyridines WO 01/17970 A1, Mar. 15, 2001; Mitsui Chemicals, Inc., Japan Process for producing substituted aromatic compound. WO 01/81274 A1, Nov. 1, 2001.

Copper-Catalyzed Halogen Exchange

Aryl and vinyl halides are widely used in organic synthesis to form carbon-carbon and carbon-heteroatom bonds in transition metal-catalyzed processes, such as the Heck, Stille, Suzuki and Ullmann-type coupling reactions. In these processes, aryl iodides are usually more reactive than the corresponding aryl bromides and uniformly more reactive than aryl chlorides, which often fail in cases where aryl iodides work well. Goldfinger, M. B.; Crawford, K. B.; Swager, T. M. *J. Am. Chem. Soc.* 1997, 119, 4578. In addition, $^{125}$I-radiolabelled aryl iodides find an important application in pharmacokinetic studies. Mertens, J.; Vanryckeghem, W.; Bossuyt, A. *J. Labelled Compd. Radiopharm.* 1985, 22, 89; Menge, W. M. P. B.; van der Goot, H.; Timmerman, H. *J. Labelled Compd. Radiopharm.* 1992, 31, 781.

Unfortunately, preparation of functionalized aryl iodides is relatively difficult. Merkushev, E. B. *Synthesis* 1988, 923. For example, iodination of arenes via diazonium salts (the Sandmeyer reaction) requires several steps. Iodination via metallated arenes can be problematic if the substrate contains electrophilic functional groups or acidic protons, both of which are incompatible with the metallated species. While direct iodination is facile in the cases of electron-rich arenes, highly reactive and expensive iodinating reagents are necessary to effect iodination of electron-poor arenes. Barluenga, J.; Gonzalez, J. M.; Garcia-Martin, M. A.; Campos, P. J.; Asensio, G. *J. Org. Chem.* 1993, 58, 2058; Olah, G. A.; Wang, Q.; Sanford, G.; Surya Prakash, G. K. *J. Org. Chem.* 1993, 58, 3194; Chaikovski, V. K.; Kharlova, T. S.; Filimonov, V. D.; Saryucheva, T. A. *Synthesis,* 1999, 748.

Nevertheless, in certain circumstances, nickel- or copper-catalyzed halogen exchange reactions may be used to prepare aryl iodides from aryl bromides or chlorides despite several drawbacks. For example, the nickel-catalyzed halogen exchange usually results in partial conversion of the aryl halides, formation of biaryl sideproducts, and the reaction may require a stoichiometric amount of the nickel catalyst. Takagi, K.; Hayama, N.; Okamoto, T. *Chem. Lett.* 1978, 191; Takagi, K.; Hayama, N.; Inokawa, S. *Bull. Chem. Soc. Jpn.* 1980, 53, 3691; Tsou, T. T.; Kochi, J. K. *J. Org. Chem.* 1980, 45, 1930; Meyer, G.; Rollin, Y.; Perichon, J. *Tetrahedron Lett.* 1986, 27, 3497; Yang, S. H.; Li, C. S.; Cheng, C. H. *J. Org. Chem.* 1987, 52, 691; Bozell, J. J.; Vogt, C. E. *J. Am. Chem. Soc.* 1988, 110, 2655; Hooijdonk, M. C. J. M.; Peters, T. H. A.; Vasilevsky, S. F.; Brandsma, L. *Synth. Commun.* 1994, 24, 1261; Milne, J. E.; Jarowicki, K.; Kocienski, P. J. *Synlett* 2002, 607. The corresponding copper-catalyzed process traditionally requires high temperatures (>150° C.), polar solvents (DMF or HMPA), and a large excess of both copper(I) iodide and potassium iodide. Suzuki, H.; Kondo, A.; Inouye, M.; Ogawa, T. *Synthesis* 1985, 121; Suzuki, H.; Kondo, A.; Ogawa, T. *Chem. Lett.* 1985, 411; Clark, J. H.; Jones, C. W. *Chem. Commun.* 1987, 1409; Suzuki H.; Aihara, M.; Yamamoto, H.; Takamoto, Y.; Ogawa, T. *Synthesis* 1988, 236.

SUMMARY OF THE INVENTION

The present invention relates to copper-catalyzed carbon-heteroatom and carbon-carbon bond-forming methods. In certain embodiments, the present invention relates to copper-catalyzed methods of forming a carbon-sulfur bond between the sulfur atom of a thiol moiety and the activated carbon of an aryl, heteroaryl, or vinyl halide or sulfonate. In other embodiments, the present invention relates to copper (II)-catalyzed methods of forming a carbon-nitrogen bond between the nitrogen atom of an amide and the activated carbon of an aryl, heteroaryl, or vinyl halide or sulfonate. In certain embodiments, the present invention relates to copper-catalyzed methods of forming a carbon-carbon bond between the carbon atom of cyanide ion and the activated carbon of an aryl, heteroaryl, or vinyl halide or sulfonate. In another embodiment, the present invention relates to a copper-catalyzed method of transforming an aryl, heteroaryl, or vinyl chloride or bromide into the corresponding aryl, heteroaryl, or vinyl iodide. Yet another embodient of the present invention relates to a tandem method, which may be practiced in a single reaction vessel, wherein the first step of the method involves the copper-catalyzed formation of an aryl, heteroaryl, or vinyl iodide from the corresponding aryl, heteroaryl, or vinyl chloride or bromide; and the second step of the method involves the copper-catalyzed formation of an aryl, heteroaryl, or vinyl nitrile, amide or sulfide from the aryl, heteroaryl, or vinyl iodide formed in the first step. Importantly, the methods of the present invention are relatively inexpensive to practice due to the low cost of the copper comprised by the catalysts.

BRIEF DESCRIPTION OF THE FIGURES

FIG. 2 tabulates examples of the copper-catalyzed arylation of thiophenols and a thiopyridine using aryl iodides.

FIG. 3 tabulates examples of the copper-catalyzed arylation of alkylthiols using aryl iodides.

FIG. 7 tabulates examples of the copper-catalyzed formation of aryl iodides and heteroaryl iodides from aryl bromides and heteroaryl bromides, respectively.

FIG. 15 depicts copper-catalyzed cyanation of aryl bromides.

DETAILED DESCRIPTION OF THE INVENTION

Figure 1:
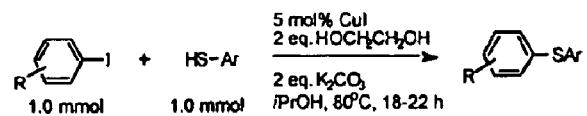
FIG. 1 tabulates examples of the copper-catalyzed arylation of thiophenols using aryl iodides.

The present invention relates to copper-catalyzed carbon-heteroatom and carbon-carbon bond-forming methods. In certain embodiments, the present invention relates to copper-catalyzed methods of forming a carbon-sulfur bond between the sulfur atom of a thiol moiety and the activated carbon of an aryl, heteroaryl, or vinyl halide or sulfonate. In other embodiments, the present invention relates to copper (II)-catalyzed methods of forming a carbon-nitrogen bond between the nitrogen atom of an amide and the activated carbon of an aryl, heteroaryl, or vinyl halide or sulfonate. In certain embodiments, the present invention relates to copper-catalyzed methods of forming a carbon-carbon bond between the carbon atom of cyanide ion and the activated carbon of an aryl, heteroaryl, or vinyl halide or sulfonate. In another embodiment, the present invention relates to a copper-catalyzed method of transforming an aryl, heteroaryl, or vinyl chloride or bromide into the corresponding aryl, heteroaryl, or vinyl iodide. Yet another embodiment of the present invention relates to a tandem method, which may be practiced in a single reaction vessel, wherein the first step of the method involves the copper-catalyzed formation of an aryl, heteroaryl, or vinyl iodide from the corresponding aryl, heteroaryl, or vinyl chloride or bromide; and the second step of the method involves the copper-catalyzed formation of an aryl, heteroaryl, or vinyl nitrile, amide or sulfide from the aryl, heteroaryl, or vinyl iodide formed in the first step. Importantly, the methods of the present invention are relatively inexpensive to practice due to the low cost of the copper comprised by the catalysts.

Copper-Catalyzed Carbon-Sulfur Bond Formation

Remarkably, we have discovered a general, efficient and operationally-simple Cu-catalyzed C—S bond formation reaction. 5-Iodo-m-xylene and thiophenol were used as the prototype substrates for preliminary optimization of the reaction conditions. Copper(I) complexes generally gave superior results compared to copper(II) sources in terms of conversion and yield of the desired diaryl sulfide product. Both $K_3PO_4$ and $K_2CO_3$ were found to be effective bases in this coupling reaction. Organic bases such as DBU or $Et_3N$ gave slightly lower yield of the diaryl sulfide. Ethylene glycol was found to be an excellent additive. Presumably, it serves as a co-solvent and ligand in the reaction. Its major function may be to get and keep the Cu(I) species in solution. In accord with this notion, fairly good results were obtained using DME, DMF, or dioxane as solvents in the absence of any additional ligand.

Thus, a system comprising 5 mol % of CuI, 2 equiv of $K_2CO_3$ and 2 equiv of ethylene glycol in isopropanol (without pre-drying and degassing) at 80° C. under argon was applied for the coupling of various functionalized aryl iodides with thiols. Both aromatic and aliphatic $NH_2$ groups, phenol, carboxylic acid, ketone, ester, amide and aldehyde functional groups are tolerated under these reaction conditions. No deleterious effect is observed when heterocyclic substrates, such as 5-iodoindole, are used. This protocol is also applicable to ortho-substituted substrates; for example, the sterically hindered 2-isopropylthiophenol can be coupled with 2-iodotoluene in 88% yield at 80° C. A 91% yield was obtained when the highly sterically hindered 2-isopropyliodobenzene and 2-isopropylthiophenol were coupled at 100° C. The presence of functional groups in the ortho position of the aryl iodide substrates are tolerated including a hydroxymethyl group and a free $NH_2$ group. As can be seen from the results in FIG. 2, a thiophenol with an ortho carboxymethyl group can be coupled in good yield. In addition, alkyl thiols were also found to be effective nucleophiles. Aryl bromides can be used for the arylation of thiols if the aryl bromide is first converted into the corresponding aryl iodide using CuI (10 mol %), a 1,2-diaminoalkane ligand (e.g., 20 mol % of N,N'-dimethylethylenediamine) and sodium iodide (2 equiv) before the addition of the thiol starting material. In summary, we have developed a general and efficient Cu-catalyzed arylation method for both aryl and alkyl thiols under mild conditions that tolerate a wide variety of functional groups.

Copper(II) Complexes for the N-Arylation of Amides

Recently, Cu(II) complexes with $CuN_4$ coordination modes have attracted a considerable amount of attention due to their potential as models for Cu(II) proteins. Karlin, K. D.; Zubieta, J. *Copper Coordination Chemistry: Biochemical and Inorganic Perspectives*; Adenine Press: New York, 1983. Among these compounds, the bis(trans-1,2-cyclohexanediamine)copper(II) bromide complex stimulated our interest as a possible air-stable precatalyst for the Cu-catalyzed amidation of aryl halides. Dhar, S.; Reddy, P. A. N.; Nethaji, M.; Mahadevan, S.; Saha, M. K.; Chakravarty, A. R. *Inorg. Chem.* 2002, 41, 3469.

Due to the greater activity observed with trans-N,N'-dimethyl-1,2-cyclohexanediamine relative to trans-1,2-cyclohexanediamine as a ligand in the Cu-catalyzed amidation of aryl halides, the bis(trans-N,N'-dimethyl-1,2-cyclohexanediamine)copper(II) bromide complex was synthesized. We have discovered a significant increase in activity with the bis(trans-N,N'-dimethyl-1,2-cyclohexanediamine)copper(II) bromide complex relative to analogous Cu(I) complex in amidation reactions carried out by premixing the amide and precatalyst. For example, in the amidation of 3,5-dimethyl-1-iodobenzene using 2-pyrrolidinone with a Cu(I)-trans-N,N'-dimethyl-1,2- cyclohexanediamine catalyst system an induction period lasting ca. 400 min was observed when the catalyst was mixed with 2-pyrrolidinone prior to the commencement of the reaction. In contrast, using the bis(trans-N,N'-dimethyl-1,2-cyclohexanediamine)copper(II) bromide complex no induction period was observed under identical reaction conditions.

Copper-Catalyzed Cyanation of Aryl Halides

We have discovered a high yielding process for the preparation of aromatic nitrites, which does not suffer from the drawbacks of known processes. In particular, the process of the invention does not require the use of an expensive palladium-based catalyst, nor does it require stoichiometric amounts of heavy metal copper or nickel cyanides, which are difficult to recover and produce toxic effluent streams when used on an industrial scale. Further, the process does not require the use of large amounts of polar solvents, which also present purification problems. This method is applicable to a variety of different aryl bromides; the reaction conditions are quite mild; and the purification of the product does not require laborious work-up procedures. In certain embodiments, the method utilizes sodium or potassium cyanide as the cyanide source.

Moreover, our method allows the copper-catalyzed conversion of aryl bromides to aromatic cyanides in presence of cyanide salts of alkali metals and a catalytic amount of potassium or sodium iodide as a halide exchange agent. Aromatic iodides, bromides, chlorides and fluorides are converted by copper(I) cyanide into the nitriles, but the iodides show much higher reactivity. We obtained in one pot the copper-catalyzed conversion of aryl bromides into the corresponding aryl iodides, followed by copper-catalyzed displacement of iodide by the cyanide to give the aromatic nitrites. The use of a catalytic amount (10 mol %) of copper(I) iodide as a copper source, N,N'-dimethylethylenediamine as a ligand, a catalytic amount (20 mol %) of sodium or potassium iodide, and a stoichiometric amount of sodium cyanide in presence of an aryl bromide with toluene as the solvent at 110° C. under an inert atmosphere, allowed us to obtain the corresponding aromatic nitrile in good to excellent yields (60–98%). Aryl bromides with various functional groups are also suitable substrates for the method because of the mild reaction conditions. Surprisingly, the cyanation of aryl bromides was much more sensitive to the nature of the copper precatalyst compared to the reaction with the corresponding aryl iodide; for example, CuI performed dramatically better than either CuBr or CuCN. This result can be rationalized assuming in situ copper-catalyzed conversion of the aryl bromide into the more reactive aryl iodide followed by the cyanation of the resulting aryl iodide. In accord with this hypothesis, addition of 20 mol % KI to the reaction mixture improved the efficiency of the cyanation reaction. Consequently, 10 mol % of CuI, 20 mol % of KI, 1.0 equiv of the inexpensive N,N'-dimethyl-1,2-aminoethylene, and 1.2 equiv of NaCN in toluene at 110° C. temperature was identified as a highly efficient system for the conversion of aryl bromides into aromatic nitriles via concurrent halogen exchange.

Figure 14:
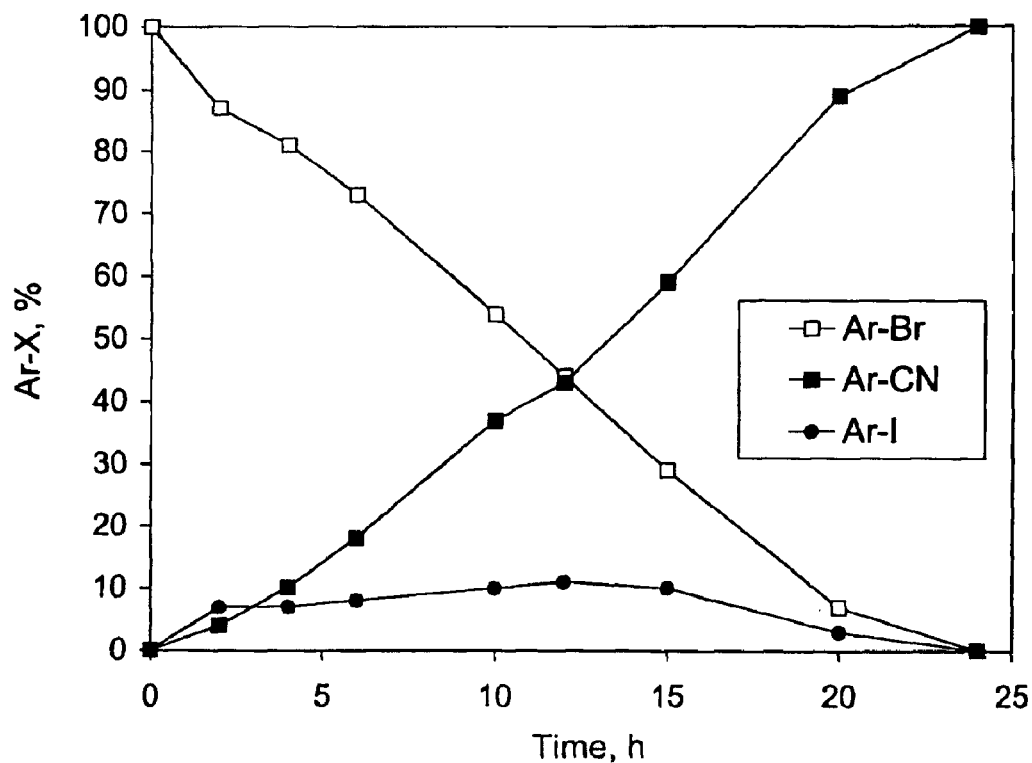
FIG. 14 depicts the reaction composition during a copper-catalyzed cyanation of 5-bromo-m-xylene.
Figure 16:
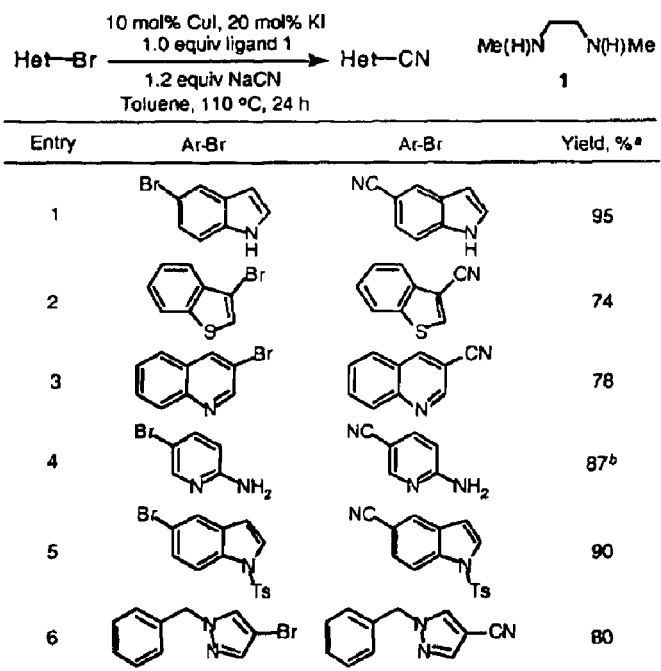
FIG. 16 depicts copper-catalyzed cyanation of heteroaryl bromides.

The success of the halide exchange-cyanation reaction largely relies on matching the relative rates of the two steps (halogen exchange and cyanation) in the domino reaction sequence. This is achieved by proper choice of the iodide salt, the cyanide salt and the solvent thus ensuring optimal concentrations of the iodide and cyanide salts in the solution. Using the combination of KI, NaCN, and toluene, about 5–10% of the aryl iodide (according to GC analysis) is present throughout the reaction, the concentration of aryl iodide decreasing only towards the end of the cyanation reaction (FIG. 14). This result indicates that the rate of halide exchange is comparable to the rate of the cyanation of the resulting aryl iodide. If polar solvents, such as DMF or sulfolane, that dissolve sodium cyanide relatively well, are used instead of toluene, very low conversion (<5%) of the aryl bromide is observed. Apparently, high concentration of the dissolved cyanide in the reaction mixture strongly inhibits both the halide exchange and the aryl cyanation reaction. Similar effect has been noted before in both palladium- and copper-catalyzed aryl cyanation reactions. See House, H. O.; Fischer, W. F., Jr. *J. Org. Chem.* 1969, 34, 3626 and Takagi, K.; Sasaki, K.; Sakakibara, Y. *Bull. Chem. Soc. Jpn.* 1991, 64, 1118.

The copper-catalyzed halide exchange-cyanation reaction tolerates a wide range of functional groups including strongly electron donating substituents, potentially C—H acidic groups, as well as free N—H and O—H groups. Although the cyanation reaction is slower with ortho-substituted aryl bromides, high yields of the aromatic nitriles can still be obtained at a slightly higher reaction temperature (130° C.). In addition, various heteroaryl bromides are also excellent substrates for the cyanation reaction. Even heterocyclic substrates containing N—H groups are well tolerated and do not suffer N-arylation, presumably because of the high affinity of the cyanide nucleophile towards the copper (I) catalyst.

Copper-Catalyzed Halogen Exchange

We have discovered that amine ligands, particularly 1,2-diaminoalkanes, greatly accelerate the copper-catalyzed halogen exchange reaction of aryl halides. N,N'-Dimethyl-1,2-diaminoalkanes are the most effective ligands although a wide variety of other amines, such as ethylenediamine, 1,2-cyclohexanediamine, and 1,3-diaminopropane, are effective. A system derived from 5 mol % CuI, 10 mol % of racemic trans-N,N'-dimethyl-1,2-cyclohexanediamine, and 2 equivalents of NaI in 1,4-dioxane as solvent at 110° C. effects conversion of aryl bromides into aryl iodides in 90–100% yields. See Exemplification. A variety of functional groups is tolerated in the aryl bromide starting material including an aliphatic ester, nitrile, and a free N—H group. In addition, a carboxylic acid group was tolerated in one example provided that hexamethyldisilazane is included in the reaction mixture to derivatize the carboxylic acid as the more soluble TMS ester, which can be readily cleaved during workup of the reaction. The halogen exchange reaction is sensitive to steric hindrance in the aryl bromide. Thus, formation of 1-iodo-2-cyclohexylbenzene required 40 h at 130° C. Various heteroaryl bromides (e.g., 5-bromoindole, 3-bromoquinoline) and vinyl bromides are excellent reaction substrates as well. Reaction temperatures as low as 70° C. are sufficient in the case of vinyl bromides. An unactivated aryl chloride can be converted into the corresponding aryl iodide although higher reaction temperature (130° C.) is required. Iodide sources other than NaI (for example, KI), and solvents ranging from non-polar, such as toluene, to polar aprotic (sulfolane) or even protic solvents (tert-amyl alcohol) can also be used. Interestingly, the halide exchange reaction proceeds best in solvents in which the iodide source is only partially soluble. In summary, we have discovered an improved method for the copper-catalyzed halogen exchange in aryl, heteroaryl and vinyl halides, which employs a much lower catalyst loading (5 mol % instead of several equivalents) and lower reaction temperatures (typically 110° C. instead of >150° C.) than the previously reported methods.

Figure 11:
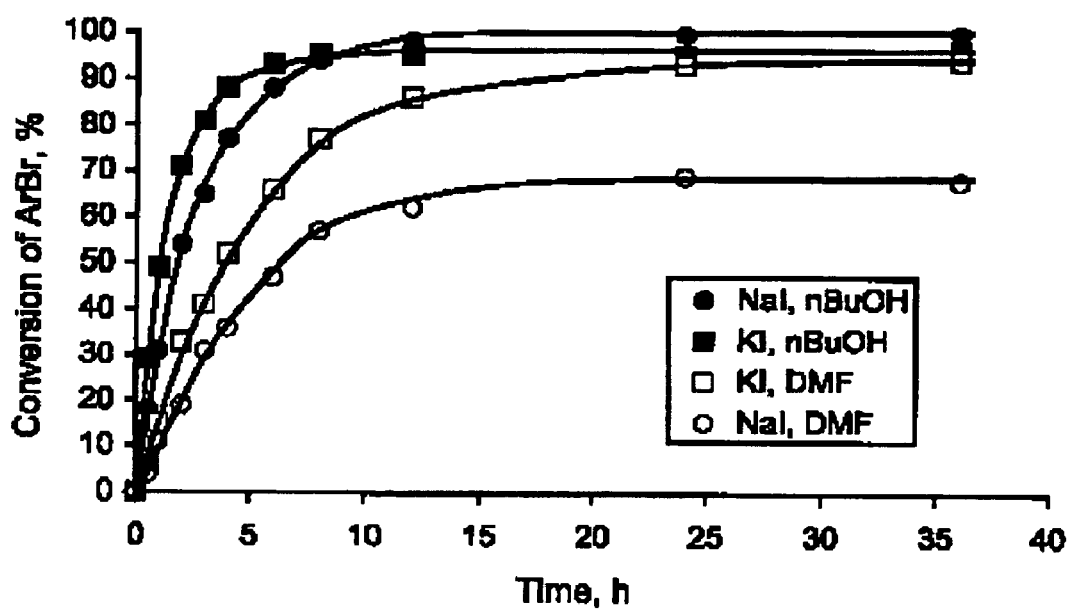
FIG. 11 depicts conversion of 5-bromo-m-xylene into 5-iodo-m-xylene using NaI or KI in n-BuOH or DMF as solvents.

The copper-catalyzed halogen exchange in aryl halides is an equilibrium reaction in which the position of the equilibrium is influenced by the solubility difference of the halide salts, in analogy to the Finkelstein reaction (halogen exchange in alkyl halides). For example, NaI in dioxane or n-butanol provides higher equilibrium conversion (99.5%) of 5-bromo-m-xylene into 5-iodo-m-xylene than either NaI or KI in DMF, which have been historically recommended for the copper-catalyzed halogen exchange (FIG. 11). See Goldfinger, M. B.; Crawford, K. B.; Swager, T. M. *J. Am. Chem. Soc.* 1997, 119, 4578. The rate of the halogen exchange exhibits an interesting dependence on the total concentration of the halide salts in the solution. Thus, NaI in DMF is the only combination in FIG. 11 that gives a homogeneous solution initially, and it also provides the lowest rate. This is further emphasized by FIG. 12 where the completely soluble tetrabutylammonium halides provide lower rates of halogen exchange (in either direction) than sodium halides, which give heterogeneous reaction mixtures. We speculate that a high concentration of the halide salts in the solution inhibits the desired halogen exchange reaction via formation of poorly reactive halocuprate complexes. See Liedholm, B.; Nilsson, M. *Acta Chem. Scand. A* 1984, 38, 555. Nevertheless, there seems to exist an optimal range of the halide concentrations because the halogen exchange reaction is sluggish in nonpolar solvents such as toluene and xylene that dissolve the iodide salt only sparingly. In those cases, solubilizing additives, such as diglyme, can be of great benefit (FIG. 13). While neither pure m-xylene or diglyme are well-suited as solvents, the use of a mixture of 5–60% diglyme in m-xylene gives excellent results. Thus, the success of the current method relies on a combination of multiple factors; most importantly, on proper choice of the ligand, solvent, and the halide salt.

Definitions

For convenience, certain terms employed in the specification, examples, and appended claims are collected here.

The term "nucleophile" is recognized in the art, and as used herein means a chemical moiety having a reactive pair of electrons. Examples of nucleophiles include uncharged compounds such as water, amines, mercaptans and alcohols, and charged moieties such as alkoxides, thiolates, carbanions, and a variety of organic and inorganic anions. Illustrative anionic nucleophiles include simple anions such as hydroxide, azide, cyanide, thiocyanate, acetate, formate or chloroformate, and bisulfite. Organometallic reagents such as organocuprates, organozincs, organolithiums, Grignard reagents, enolates, acetylides, and the like may, under appropriate reaction conditions, be suitable nucleophiles. Hydride may also be a suitable nucleophile when reduction of the substrate is desired.

The term "electrophile" is art-recognized and refers to chemical moieties which can accept a pair of electrons from a nucleophile as defined above. Electrophiles useful in the method of the present invention include cyclic compounds such as epoxides, aziridines, episulfides, cyclic sulfates, carbonates, lactones, lactams and the like. Non-cyclic electrophiles include sulfates, sulfonates (e.g. tosylates), chlorides, bromides, iodides, and the like The terms "electrophilic atom", "electrophilic center" and "reactive center" as used herein refer to the atom of the substrate which is attacked by, and forms a new bond to, the nucleophile. In most (but not all) cases, this will also be the atom from which the leaving group departs.

The term "electron-withdrawing group" is recognized in the art and as used herein means a functionality which draws electrons to itself more than a hydrogen atom would at the same position. Exemplary electron-withdrawing groups include nitro, ketone, aldehyde, sulfonyl, trifluoromethyl, —CN, chloride, and the like. The term "electron-donating group", as used herein, means a functionality which draws electrons to itself less than a hydrogen atom would at the same position. Exemplary electron-donating groups include amino, methoxy, and the like.

The term "polar solvent" refers to a solvent with a dielectric constant(s) greater than or equal to about 20. For example, water, methanol, dimethyl sulfoxide, N,N-dimethylformamide and acetonitrile are polar solvents.

The terms "Lewis base" and "Lewis basic" are recognized in the art, and refer to a chemical moiety capable of donating a pair of electrons under certain reaction conditions. Examples of Lewis basic moieties include uncharged compounds such as alcohols, thiols, olefins, and amines, and charged moieties such as alkoxides, thiolates, carbanions, and a variety of other organic anions.

The term "Bronsted base" is art-recognized and refers to an uncharged or charged atom or molecule, e.g., an oxide, amine, alkoxide, or carbonate, that is a proton acceptor.

The terms "Lewis acid" and "Lewis acidic" are art-recognized and refer to chemical moieties which can accept a pair of electrons from a Lewis base.

The term "meso compound" is recognized in the art and means a chemical compound which has at least two chiral centers but is a chiral due to an internal plane, or point, of symmetry.

The term "chiral" refers to molecules which have the property of non-superimposability on their mirror image partner, while the term "achiral" refers to molecules which are superimposable on their mirror image partner. A "prochiral molecule" is an achiral molecule which has the potential to be converted to a chiral molecule in a particular process.

The term "stereoisomers" refers to compounds which have identical chemical constitution, but differ with regard to the arrangement of their atoms or groups in space. In particular, the term "enantiomers" refers to two stereoisomers of a compound which are non-superimposable mirror images of one another. The term "diastereomers", on the other hand, refers to the relationship between a pair of stereoisomers that comprise two or more asymmetric centers and are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product. The subject method is said to produce a "stereoselectively-enriched" product (e.g., enantioselectively-enriched or diastereoselectively-enriched) when the yield of a particular stereoisomer of the product is greater by a statistically significant amount relative to the yield of that stereoisomer resulting from the same reaction run in the absence of a chiral catalyst. For example, an enantioselective reaction catalyzed by one of the subject chiral catalysts will yield an e.e. for a particular enantiomer that is larger than the e.e. of the reaction lacking the chiral catalyst.

The term "regioisomers" refers to compounds which have the same molecular formula but differ in the connectivity of the atoms. Accordingly, a "regioselective process" is one which favors the production of a particular regioisomer over others, e.g., the reaction produces a statistically significant preponderance of a certain regioisomer.

The term "reaction product" means a compound which results from the reaction of a nucleophile and a substrate. In general, the term "reaction product" will be used herein to refer to a stable, isolable compound, and not to unstable intermediates or transition states.

The term "substrate" is intended to mean a chemical compound which can react with a nucleophile, or with a ring-expansion reagent, according to the present invention, to yield at least one product having a stereogenic center.

The term "catalytic amount" is recognized in the art and means a substoichiometric amount relative to a reactant.

As discussed more fully below, the reactions contemplated in the present invention include reactions which are enantioselective, diastereoselective, and/or regioselective. An enantioselective reaction is a reaction which converts an achiral reactant to a chiral product enriched in one enantiomer. Enantioselectivity is generally quantified as "enantiomeric excess" (ee) defined as follows:

% Enantiomeric Excess A (ee)=(% Enantiomer A)−(% Enantiomer B)

where A and B are the enantiomers formed. Additional terms that are used in conjunction with enatioselectivity include "optical purity" or "optical activity". An enantioselective reaction yields a product with an e.e. greater than zero. Preferred enantioselective reactions yield a product with an e.e. greater than 20%, more preferably greater than 50%, even more preferably greater than 70%, and most preferably greater than 80%.

A diastereoselective reaction converts a chiral reactant (which may be racemic or enantiomerically pure) to a product enriched in one diastereomer. If the chiral reactant is racemic, in the presence of a chiral non-racemic reagent or catalyst, one reactant enantiomer may react more slowly than the other. This class of reaction is termed a kinetic resolution, wherein the reactant enantiomers are resolved by differential reaction rate to yield both enantiomerically-enriched product and enantimerically-enriched unreacted substrate. Kinetic resolution is usually achieved by the use of sufficient reagent to react with only one reactant enantiomer (i.e. one-half mole of reagent per mole of racemic substrate). Examples of catalytic reactions which have been used for kinetic resolution of racemic reactants include the Sharpless epoxidation and the Noyori hydrogenation.

A regioselective reaction is a reaction which occurs preferentially at one reactive center rather than another non-identical reactive center. For example, a regioselective reaction of an unsymmetrically substituted epoxide substrate would involve preferential reaction at one of the two epoxide ring carbons.

The term "non-racemic" with respect to the chiral catalyst, means a preparation of catalyst having greater than 50% of a given enantiomer, more preferably at least 75%. "Substantially non-racemic" refers to preparations of the catalyst which have greater than 90% ee for a given enantiomer of the catalyst, more preferably greater than 95% ee.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 of fewer. Likewise, preferred cycloalkyls have from 4–10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths.

The terms "alkenyl" and "alkynyl" refer to unsaturated aliphatic groups analogous in length and possible substitution to the alkyls described above, but which contain at least one double or triple carbon-carbon bond, respectively.

The term "organometallic" refers to compounds comprising a metallic atom (such as mercury, zinc, lead, magnesium or lithium) or a metalloid atom (such as silicon, or tin) that is bonded directly to a carbon atom, such as methyl magnesium bromide, phenyl lithium, and phenyl-trimethyl-tin.

The terms "amine" and "amino" are art-recognized and refer to both unsubstituted and substituted amines, e.g., a moiety that can be represented by the general formula:

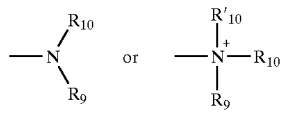

wherein $R_9$, $R_{10}$ and $R'_{10}$ each independently represent a group permitted by the rules of valence.

The abbreviation "DBU" refers to 1,8-diazabicyclo[5.4.0] undec-7-ene, which has the following structure:

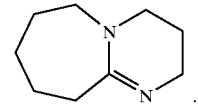

The term "acylamino" is art-recognized and refers to a moiety that can be represented by the general formula:

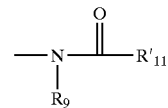

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

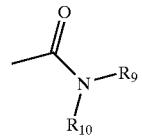

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art recognized and includes such moieties as can be represented by the general formula:

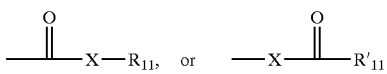

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

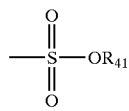

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutane-sulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The term "sulfonylamino" is art recognized and includes a moiety that can be represented by the general formula:

The term "sulfamoyl" is art-recognized and includes a moiety that can be represented by the general formula:

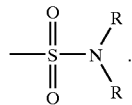

The term "sulfonyl", as used herein, refers to a moiety that can be represented by the general formula:

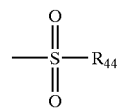

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

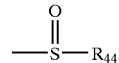

in which $R_{44}$ is selected from the group consisting of hydrogen, alkyl, alkenyl, alkynyl, cycloalkyl, heterocyclyl, aralkyl, or aryl.

The term "sulfate", as used herein, means a sulfonyl group, as defined above, attached to two hydroxy or alkoxy groups. Thus, in a preferred embodiment, a sulfate has the structure:

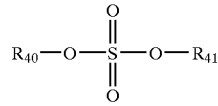

in which $R_{40}$ and $R_{41}$ are independently absent, a hydrogen, an alkyl, or an aryl. Furthermore, $R_{40}$ and $R_{41}$, taken together with the sulfonyl group and the oxygen atoms to which they are attached, may form a ring structure having from 5 to 10 members.

Analogous substitutions can be made to alkenyl and alkynyl groups to produce, for example, alkenylamines, alkynylamines, alkenylamides, alkynylamides, alkenylimines, alkynylimines, thioalkenyls, thioalkynyls, carbonyl-substituted alkenyls or alkynyls, alkenoxyls, alkynoxyls, metalloalkenyls and metalloalkynyls.

The term "aryl" as used herein includes 4-, 5-, 6- and 7-membered single-ring aromatic groups which may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycle". The aromatic ring can be substituted at one or more ring positions with such substituents as described above, as for example, halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —CN, or the like.

The terms "heterocycle" or "heterocyclic group" refer to 4 to 10-membered ring structures, more preferably 5 to 7 membered rings, which ring structures include one to four heteroatoms. Heterocyclic groups include pyrrolidine, oxolane, thiolane, imidazole, oxazole, piperidine, piperazine, morpholine. The heterocyclic ring can be substituted at one or more positions with such substituents as described above, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —CN, or the like.

The terms "polycycle" or "polycyclic group" refer to two or more cyclic rings (e.g., cycloalkyls, cycloalkenyls, cycloalkynyls, aryls and/or heterocycles) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —CN, or the like.

The term "heteroatom" as used herein means an atom of any element other than carbon or hydrogen. Preferred heteroatoms are nitrogen, oxygen, sulfur, phosphorus and selenium.

For purposes of this invention, the chemical elements are identified in accordance with the Periodic Table of the Elements, CAS version, Handbook of Chemistry and Physics, 67th Ed., 1986–87, inside cover.

The terms ortho, meta and para apply to 1,2-, 1,3- and 1,4-disubstituted benzenes, respectively. For example, the names 1,2-dimethylbenzene and ortho-dimethylbenzene are synonymous.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms, represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Methods of the Invention

In certain embodiments, a method of the present invention is represented by Scheme 1:

Scheme 1

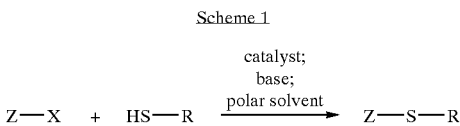

wherein

X represents I, Br, Cl, alkylsulfonate, or arylsulfonate;

Z represents optionally substituted aryl, heteroaryl, or alkenyl;

catalyst comprises a copper atom or ion;

base represents a Bronsted base; and

R represents optionally substituted alkyl, cycloalkyl, aryl, heteroaryl, aralkyl, heteroaralkyl, alkenylalkyl, or alkynylalkyl.

In certain embodiments, the methods of the present invention are represented by Scheme 1 and the attendant definitions, wherein X represents I.

In certain embodiments, the methods of the present invention are represented by Scheme 1 and the attendant definitions, wherein X represents Br.

In certain embodiments, the methods of the present invention are represented by Scheme 1 and the attendant definitions, wherein Z represents optionally substituted aryl.

In certain embodiments, the methods of the present invention are represented by Scheme 1 and the attendant definitions, wherein Z represents optionally substituted phenyl.

In certain embodiments, the methods of the present invention are represented by Scheme 1 and the attendant definitions, wherein the base is a carbonate, phosphate, oxide, hydroxide, alkoxide, aryloxide, amine, metal amide, fluoride, or guanidine.

In certain embodiments, the methods of the present invention are represented by Scheme 1 and the attendant definitions, wherein the base is potassium phosphate, potassium carbonate, cesium carbonate, sodium tert-butoxide, or sodium carbonate.

In certain embodiments, the methods of the present invention are represented by Scheme 1 and the attendant definitions, wherein X represents I; and Z represents optionally substituted aryl.

In certain embodiments, the methods of the present invention are represented by Scheme 1 and the attendant definitions, wherein X represents I; and Z represents optionally substituted phenyl.

In certain embodiments, the methods of the present invention are represented by Scheme 1 and the attendant definitions, wherein X represents I; Z represents optionally substituted aryl; and the base is a carbonate, phosphate, oxide, hydroxide, alkoxide, aryloxide, amine, metal amide, fluoride, or guanidine.

In certain embodiments, the methods of the present invention are represented by Scheme 1 and the attendant definitions, wherein X represents I; Z represents optionally substituted phenyl; and the base is a carbonate, phosphate, oxide, hydroxide, alkoxide, aryloxide, amine, metal amide, fluoride, or guanidine.

In certain embodiments, the methods of the present invention are represented by Scheme 1 and the attendant definitions, wherein X represents I; Z represents optionally substituted aryl; and the base is potassium phosphate, potassium carbonate, cesium carbonate, sodium tert-butoxide, or sodium carbonate.

In certain embodiments, the methods of the present invention are represented by Scheme 1 and the attendant definitions, wherein X represents I; Z represents optionally substituted phenyl; and the base is potassium phosphate, potassium carbonate, cesium carbonate, sodium tert-butoxide, or sodium carbonate.

In certain embodiments, the methods of the present invention are represented by Scheme 1 and the attendant definitions, wherein X represents Br; and Z represents optionally substituted aryl.

In certain embodiments, the methods of the present invention are represented by Scheme 1 and the attendant definitions, wherein X represents Br; and Z represents optionally substituted phenyl.

In certain embodiments, the methods of the present invention are represented by Scheme 1 and the attendant definitions, wherein X represents Br; Z represents optionally substituted aryl; and the base is a carbonate, phosphate, oxide, hydroxide, alkoxide, aryloxide, amine, metal amide, fluoride, or guanidine.

In certain embodiments, the methods of the present invention are represented by Scheme 1 and the attendant definitions, wherein X represents Br; Z represents optionally substituted phenyl; and the base is a carbonate, phosphate, oxide, hydroxide, alkoxide, aryloxide, amine, metal amide, fluoride, or guanidine.

In certain embodiments, the methods of the present invention are represented by Scheme 1 and the attendant definitions, wherein X represents Br; Z represents optionally substituted aryl; and the base is potassium phosphate, potassium carbonate, cesium carbonate, sodium tert-butoxide, or sodium carbonate.

In certain embodiments, the methods of the present invention are represented by Scheme 1 and the attendant definitions, wherein X represents Br; Z represents optionally substituted phenyl; and the base is potassium phosphate, potassium carbonate, cesium carbonate, sodium tert-butoxide, or sodium carbonate.

In certain embodiments, the methods of the present invention are represented by Scheme 1 and the attendant definitions, wherein the catalyst is present in less than or equal to about 10 mol % relative to Z—X.

In certain embodiments, the methods of the present invention are represented by Scheme 1 and the attendant definitions, wherein the catalyst is present in less than or equal to about 5 mol % relative to Z—X.

In certain embodiments, the methods of the present invention are represented by Scheme 1 and the attendant definitions, wherein the method is conducted at a temperature less than about 150 C.

In certain embodiments, the methods of the present invention are represented by Scheme 1 and the attendant definitions, wherein the method is conducted at a temperature less than about 100 C.

In certain embodiments, the methods of the present invention are represented by Scheme 1 and the attendant definitions, wherein the method is conducted at a temperature less than about 90 C.

In certain embodiments, the methods of the present invention are represented by Scheme 1 and the attendant definitions, wherein the method is conducted at a temperature less than about 85 C.

In certain embodiments, a method of the present invention is represented by Scheme 2:

Scheme 2

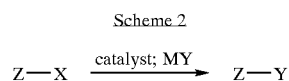

wherein

M represents an alkali metal cation, alkaline earth cation, transition metal cation, lanthanide cation, actinide cation, ammonium ion, or phosphonium ion;

X represents I, Br or Cl;

Y represents I, Br, or Cl;

Z represents optionally substituted aryl, heteroaryl or alkenyl; and catalyst comprises a copper atom or ion, and a ligand.

In certain embodiments, the methods of the present invention are represented by Scheme 2 and the attendant definitions, wherein M represents a sodium cation, potassium cation or copper cation.

In certain embodiments, the methods of the present invention are represented by Scheme 2 and the attendant definitions, wherein X represents Br.

In certain embodiments, the methods of the present invention are represented by Scheme 2 and the attendant definitions, wherein Y represents I.

In certain embodiments, the methods of the present invention are represented by Scheme 2 and the attendant definitions, wherein the ligand comprised by the catalyst is an optionally substituted diamine.

In certain embodiments, the methods of the present invention are represented by Scheme 2 and the attendant definitions, wherein the ligand comprised by the catalyst is an optionally substituted 1,2-diaminocyclohexane, 1,2-diaminoalkane, 1,3-diaminoalkane, or 1,10-phenanthroline.

In certain embodiments, the methods of the present invention are represented by Scheme 2 and the attendant definitions, wherein the ligand comprised by the catalyst is an optionally substituted 1,2-diaminocyclohexane, 1,2-diaminoethane, 1,3-diaminopropane, or 1,10-phenanthroline.

In certain embodiments, the methods of the present invention are represented by Scheme 2 and the attendant definitions, wherein the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2- diaminocyclohexane, or a mixture of cis- and trans-N-tolyl-1,2-diaminocyclohexane.

In certain embodiments, the methods of the present invention are represented by Scheme 2 and the attendant definitions, wherein the ligand comprised by the catalyst is trans-N,N'-dimethyl-1,2-diaminocyclohexane or N,N'-dimethylethylenediamine.

In certain embodiments, the methods of the present invention are represented by Scheme 2 and the attendant definitions, wherein M represents a sodium cation, potassium cation or copper cation; and X represents Br.

In certain embodiments, the methods of the present invention are represented by Scheme 2 and the attendant definitions, wherein M represents a sodium cation, potassium cation or copper cation; X represents Br; and Y represents I.

In certain embodiments, the methods of the present invention are represented by Scheme 2 and the attendant definitions, wherein M represents a sodium cation, potassium cation or copper cation; X represents Br; Y represents I; and the ligand comprised by the catalyst is an optionally substituted diamine.

In certain embodiments, the methods of the present invention are represented by Scheme 2 and the attendant definitions, wherein M represents a sodium cation, potassium cation or copper cation; X represents Br; Y represents I; and the ligand comprised by the catalyst is an optionally substituted 1,2-diaminocyclohexane, 1,2-diaminoalkane, 1,3-diaminoalkane, or 1,10-phenanthroline.

In certain embodiments, the methods of the present invention are represented by Scheme 2 and the attendant definitions, wherein M represents a sodium cation, potassium cation or copper cation; X represents Br; Y represents I; and the ligand comprised by the catalyst is an optionally substituted 1,2-diaminocyclohexane, 1,2-diaminoethane, 1,3-diaminopropane, or 1,10-phenanthroline.

In certain embodiments, the methods of the present invention are represented by Scheme 2 and the attendant definitions, wherein M represents a sodium cation, potassium cation or copper cation; X represents Br; Y represents I; and the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, or a mixture of cis- and trans-N-tolyl-1,2-diaminocyclohexane.

In certain embodiments, the methods of the present invention are represented by Scheme 2 and the attendant definitions, wherein M represents a sodium cation, potassium cation or copper cation; X represents Br; Y represents I; and the ligand comprised by the catalyst is trans-N,N'-dimethyl-1,2-diaminocyclohexane or N,N'-dimethylethylenediamine.

In certain embodiments, the methods of the present invention are represented by Scheme 2 and the attendant definitions, wherein the catalyst is present in less than or equal to about 10 mol % relative to Z—X.

In certain embodiments, the methods of the present invention are represented by Scheme 2 and the attendant definitions, wherein the catalyst is present in less than or equal to about 5 mol % relative to Z—X.

In certain embodiments, the methods of the present invention are represented by Scheme 2 and the attendant definitions, wherein the method is conducted at a temperature less than about 150 C.

In certain embodiments, the methods of the present invention are represented by Scheme 2 and the attendant definitions, wherein the method is conducted at a temperature less than about 140 C.

In certain embodiments, the methods of the present invention are represented by Scheme 2 and the attendant definitions, wherein the method is conducted at a temperature less than about 125 C.

In certain embodiments, the methods of the present invention are represented by Scheme 2 and the attendant definitions, wherein the method is conducted at a temperature less than about 115 C.

In certain embodiments, a method of the present invention is represented by Scheme 3:

Scheme 3

wherein

M represents an alkali metal cation, alkaline earth cation, transition metal cation, lanthanide cation, actinide cation, ammonium ion, or phosphonium ion;

Z represents optionally substituted aryl, heteroaryl or alkenyl; and catalyst comprises a copper atom or ion, and a ligand.

In certain embodiments, the methods of the present invention are represented by Scheme 3 and the attendant definitions, wherein M represents a sodium cation, potassium cation or copper cation.

In certain embodiments, the methods of the present invention are represented by Scheme 3 and the attendant definitions, wherein the ligand comprised by the catalyst is an optionally substituted diamine.

In certain embodiments, the methods of the present invention are represented by Scheme 3 and the attendant definitions, wherein the ligand comprised by the catalyst is an optionally substituted 1,2-diaminocyclohexane, 1,2-diaminoalkane, 1,3-diaminoalkane, or 1,10-phenanthroline.

In certain embodiments, the methods of the present invention are represented by Scheme 3 and the attendant definitions, wherein the ligand comprised by the catalyst is an optionally substituted 1,2-diaminocyclohexane, 1,2-diaminoethane, 1,3-diaminopropane, or 1,10-phenanthroline.

In certain embodiments, the methods of the present invention are represented by Scheme 3 and the attendant definitions, wherein the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, or a mixture of cis- and trans-N-tolyl-1,2-diaminocyclohexane.

In certain embodiments, the methods of the present invention are represented by Scheme 3 and the attendant definitions, wherein the ligand comprised by the catalyst is trans-N,N'-dimethyl-1,2-diaminocyclohexane or N,N'-dimethylethylenediamine.

In certain embodiments, the methods of the present invention are represented by Scheme 3 and the attendant definitions, wherein M represents a sodium cation, potassium cation or copper cation; and the ligand comprised by the catalyst is an optionally substituted diamine.

In certain embodiments, the methods of the present invention are represented by Scheme 3 and the attendant definitions, wherein M represents a sodium cation, potassium cation or copper cation; and the ligand comprised by the catalyst is an optionally substituted 1,2-diaminocyclohexane, 1,2-diaminoalkane, 1,3-diaminoalkane, or 1,10-phenanthroline.

In certain embodiments, the methods of the present invention are represented by Scheme 3 and the attendant definitions, wherein M represents a sodium cation, potassium cation or copper cation; and the ligand comprised by the catalyst is an optionally substituted 1,2-diaminocyclohexane, 1,2-diaminoethane, 1,3-diaminopropane, or 1,10-phenanthroline.

In certain embodiments, the methods of the present invention are represented by Scheme 3 and the attendant definitions, wherein M represents a sodium cation, potassium cation or copper cation; and the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, or a mixture of cis- and trans-N-tolyl-1,2-diaminocyclohexane.

In certain embodiments, the methods of the present invention are represented by Scheme 3 and the attendant definitions, wherein M represents a sodium cation, potassium cation or copper cation; and the ligand comprised by the catalyst is trans-N,N'-dimethyl-1,2-diaminocyclohexane or N,N'-dimethylethylenediamine.

In certain embodiments, the methods of the present invention are represented by Scheme 3 and the attendant definitions, wherein the catalyst is present in less than or equal to about 15 mol % relative to Z—I.

In certain embodiments, the methods of the present invention are represented by Scheme 3 and the attendant definitions, wherein the catalyst is present in less than or equal to about 10 mol % relative to Z—I.

In certain embodiments, the methods of the present invention are represented by Scheme 3 and the attendant definitions, wherein the catalyst is present in less than or equal to about 5 mol % relative to Z—I.

In certain embodiments, the methods of the present invention are represented by Scheme 3 and the attendant definitions, wherein the method is conducted at a temperature less than about 150 C.

In certain embodiments, the methods of the present invention are represented by Scheme 3 and the attendant definitions, wherein the method is conducted at a temperature less than about 140 C.

In certain embodiments, the methods of the present invention are represented by Scheme 3 and the attendant definitions, wherein the method is conducted at a temperature less than about 125 C.

In certain embodiments, the methods of the present invention are represented by Scheme 3 and the attendant definitions, wherein the method is conducted at a temperature less than about 115 C.

In certain embodiments, a method of the present invention is represented by Scheme 4:

Scheme 4

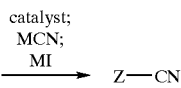

wherein
M represents independently for each occurrence an alkali metal cation, alkaline earth cation, transition metal cation, lanthanide cation, actinide cation, ammonium ion, or phosphonium ion;
X represents Br or Cl;
Z represents optionally substituted aryl, heteroaryl or alkenyl; and
catalyst comprises a copper atom or ion, and a ligand.

In certain embodiments, the methods of the present invention are represented by Scheme 4 and the attendant definitions, wherein M represents independently for each occurrence a sodium cation, potassium cation or copper cation.

In certain embodiments, the methods of the present invention are represented by Scheme 4 and the attendant definitions, wherein X represents Br.

In certain embodiments, the methods of the present invention are represented by Scheme 4 and the attendant definitions, wherein the ligand comprised by the catalyst is an optionally substituted diamine.

In certain embodiments, the methods of the present invention are represented by Scheme 4 and the attendant definitions, wherein the ligand comprised by the catalyst is an optionally substituted 1,2-diaminocyclohexane, 1,2-diaminoalkane, 1,3-diaminoalkane, or 1,10-phenanthroline.

In certain embodiments, the methods of the present invention are represented by Scheme 4 and the attendant definitions, wherein the ligand comprised by the catalyst is an optionally substituted 1,2-diaminocyclohexane, 1,2-diaminoethane, 1,3-diaminopropane, or 1,10-phenanthroline.

In certain embodiments, the methods of the present invention are represented by Scheme 4 and the attendant definitions, wherein the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, or a mixture of cis- and trans-N-tolyl-1,2-diaminocyclohexane.

In certain embodiments, the methods of the present invention are represented by Scheme 4 and the attendant definitions, wherein the ligand comprised by the catalyst is trans-N,N'-dimethyl-1,2-diaminocyclohexane or N,N'-dimethylethylenediamine.

In certain embodiments, the methods of the present invention are represented by Scheme 4 and the attendant definitions, wherein M represents independently for each occurrence a sodium cation, potassium cation or copper cation; and X represents Br.

In certain embodiments, the methods of the present invention are represented by Scheme 4 and the attendant definitions, wherein M represents independently for each occurrence a sodium cation, potassium cation or copper cation; X represents Br; and the ligand comprised by the catalyst is an optionally substituted diamine.

In certain embodiments, the methods of the present invention are represented by Scheme 4 and the attendant definitions, wherein M represents independently for each occurrence a sodium cation, potassium cation or copper cation; X represents Br; and the ligand comprised by the catalyst is an optionally substituted 1,2-diaminocyclohexane, 1,2-diaminoalkane, 1,3-diaminoalkane, or 1,10-phenanthroline.

In certain embodiments, the methods of the present invention are represented by Scheme 4 and the attendant definitions, wherein M represents independently for each occurrence a sodium cation, potassium cation or copper cation; X represents Br; and the ligand comprised by the catalyst is an optionally substituted 1,2-diaminocyclohexane, 1,2-diaminoethane, 1,3-diaminopropane, or 1,10-phenanthroline.

In certain embodiments, the methods of the present invention are represented by Scheme 4 and the attendant definitions, wherein M represents independently for each occurrence a sodium cation, potassium cation or copper cation; X represents Br; and the ligand comprised by the catalyst is cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, or a mixture of cis- and trans-N-tolyl-1,2-diaminocyclohexane.

In certain embodiments, the methods of the present invention are represented by Scheme 4 and the attendant definitions, wherein M represents independently for each occurrence a sodium cation, potassium cation or copper cation; X represents Br; and the ligand comprised by the catalyst is trans-N,N'-dimethyl-1,2-diaminocyclohexane or N,N'-dimethylethylenediamine.

In certain embodiments, the methods of the present invention are represented by Scheme 4 and the attendant definitions, wherein the catalyst is present in less than or equal to about 15 mol % relative to Z—X.

In certain embodiments, the methods of the present invention are represented by Scheme 4 and the attendant definitions, wherein the catalyst is present in less than or equal to about 10 mol % relative to Z—X.

In certain embodiments, the methods of the present invention are represented by Scheme 4 and the attendant definitions, wherein the catalyst is present in less than or equal to about 5 mol % relative to Z—X.

In certain embodiments, the methods of the present invention are represented by Scheme 4 and the attendant definitions, wherein the method is conducted at a temperature less than about 150 C.

In certain embodiments, the methods of the present invention are represented by Scheme 4 and the attendant definitions, wherein the method is conducted at a temperature less than about 140 C.

In certain embodiments, the methods of the present invention are represented by Scheme 4 and the attendant definitions, wherein the method is conducted at a temperature less than about 125 C.

In certain embodiments, the methods of the present invention are represented by Scheme 4 and the attendant definitions, wherein the method is conducted at a temperature less than about 115 C.

Catalysts of the Invention

The catalysts used in the methods of the present invention comprise a copper atom or ion. The copper atom or ion of the catalyst may be derived from any commercially available copper salt, e.g., a copper (I) or copper (II) salt. In certain embodiments, the copper atom or ion is provided as copper (I) iodide. In other embodiments, the copper atom or ion is provided as copper (I) oxide.

In certain embodiments, e.g., catalysts used in transformations of aryl, heteroaryl or vinyl chlorides or bromides to the corresponding iodides, the catalysts also comprise a ligand. The ligand of a catalyst comprises a Lewis basic atom, e.g., selected from nitrogen, oxygen, sulfur, phosphorus, and arsenic, such that the Lewis basic atom is capable of interacting with the aforementioned copper atom or ion. The ligand of a catalyst may be a chelating ligand, i.e., a ligand comprising two Lewis basic atoms, e.g., selected from nitrogen, oxygen, phosphorus, and arsenic, with a spatial relationship therebetween, such that the Lewis basic atoms are capable of interacting simultaneously with the aforementioned copper atom or ion. For example, a chelating ligand may be a diamine, aminoalcohol, or a bis-phosphine. In certain embodiments, a chelating ligand is a 1,2-diamine, or 1,3-diamine. In certain embodiments, a chelating ligand is a 1,2-diaminocyclohexane, a 1,10-phenanthroline, a 2-hydroxyethyl amine, or a 1,2-diaminoethane. In certain embodiments, a chelating ligand is 1,2-diaminocyclohexane, N,N'-dimethyl-1,2-diaminocyclohexane, N-tolyl-1,2-diaminocyclohexane, 1,10-phenanthroline, ethanolamine, 1,2-diaminoethane, or N,N'-dimethyl-1,2-diaminoethane. In certain embodiments, a chelating ligand is cis-1,2-diaminocyclohexane, trans-1,2-diaminocyclohexane, or a mixture of cis- and trans-1,2-diaminocyclohexane. Additionally, with respect to asymmetric chelating ligands, the ligand may be provided as a single enantiomer, a mixture of stereoisomers, or a racemic mixture. In certain embodiments, the ligand serves as the solvent for a method of the present invention. For example, in an embodiment wherein the ligand comprised by the catalyst is an amine that is a liquid under the conditions for practicing a method of the present invention, the method may be practiced using said amine as the solvent.

The copper atom or ion and the ligand of the catalyst of the methods of the present invention may be added to the reaction mixture separately or simultaneously, or they maybe added in the form of preformed catalyst complex. Although the methods of the present invention do not require the formation of a copper-chelating ligand complex, such complexes are likely present. Moreover, the identity of the ligand effects various characteristics of the methods of the present invention.

In certain embodiments, the catalyst of a method of the present invention is covalently tethered to a solid support, e.g., a polymer bead or a resin. For example, the ligand of a catalyst of the present invention may be covalently tethered to a solid support, e.g., a Wang resin. Additionally, one or more of the substrates of a method of the present invention may be covalently tethered to a solid support, e.g., a polymer bead or a resin. For example, the Z—X substrate of a method of the present invention may be covalently tethered to a solid support, e.g., a Wang resin. Alternatively, the nucleophilic substrate, i.e., the substrate that effectively replaces X in Z—X, of a method of the present invention may be covalently tethered to a solid support, e.g., a Wang resin. Further, in certain embodiments, both substrates may be covalently tethered to a solid support. In certain embodiments, one or more of the substrates or the catalyst or any of them are isolated in a semi-permeable membrane, e.g., a dialysis bag.

Suitable Bases

A wide range of Bronsted bases may be used in the methods of the present invention. Generally, any Bronsted base may be used in the methods of the present invention. For example, suitable bases include $K_3PO_4$, $K_2CO_3$, $Na_2CO_3$, $Tl_2CO_3$, $Cs_2CO_3$, K(OtBu), Li(OtBu), Na(OtBu), K(OPh), and Na(OPh), or mixtures thereof. Suitable Bronsted bases also include amines, e.g., triethylamine and DBU. In certain embodiments, the Bronsted base used will be selected from the group consisting of phosphates, carbonates, and alkoxides. In certain embodiments, the base is selected from the group consisting of potassium phosphate, potassium carbonate, and cesium carbonate.

Typically, there is no need to use large excesses of base in the methods of the present invention. In certain embodiments, no more than four equivalents of base are used, relative to the nucleophilic reactant. In other embodiments, no more than two equivalents of base are used, relative to the nucleophilic reactant. Further, in reactions using the corresponding anion of the nucleophilic reactant in place of its conjugate base, there may be no need for additional base.

Nucleophiles

Nucleophiles which are useful in the methods of the present invention may be selected by the skilled artisan according to several criteria. In general, a suitable nucleophile will have one or more of the following properties: 1) It will be capable of reaction with the substrate at the desired electrophilic site; 2) It will yield a useful product upon reaction with the substrate; 3) It will not react with the substrate at functionalities other than the desired electrophilic site; 4) It will react with the substrate at least partly through a mechanism catalyzed by the chiral catalyst; 5) It will not substantially undergo further undesired reaction after reacting with the substrate in the desired sense; and 6) It will not substantially react with or degrade the catalyst. It will be understood that while undesirable side reactions (such as catalyst degradation) may occur, the rates of such reactions can be rendered slow—through the selection of reactants and conditions—in comparison with the rate of the desired reaction(s).

Routine experimentation may be necessary to determine the preferred nucleophile for a given transformation. For example, a sulfur-containing nucleophile, such as an thiol, thiolate anion, or thiourea, may be used to form an carbon-sulfur bond. Likewise, a carbon nucleophile, e.g., cyanide ion, may be used to form a carbon-carbon bond. Further, halide ions may be used to form carbon-halogen bonds. Additional suitable nucleophiles will be apparent to those of ordinary skill in the art of organic chemistry. A nucleophile introduced in the reaction mixture as an anion may comprise a conventional counterion, e.g., an alkali metal cation, alkaline earth cation, or ammonium ion. In certain embodiments, the nucleophilic moiety may be part of the substrate, resulting in an intramolecular bond-forming reaction.

Aryl, Heteroaryl or Vinyl Halides or Sulfonates

The methods of the present invention may be used to form a bond between the halogen-bearing or sulfonate-bearing carbon atom of an aryl halide or sulfonate, heteroaryl halide or sulfonate, or vinyl halide or sulfonate, and a nucleophilic atom of a second molecule or ion. Of course, as mentioned supra, the halogen-bearing carbon of the aryl halide, heteroaryl halide, or vinyl halide, or the sulfonate-bearing carbon of the aryl sulfonate, heteroaryl sulfonate, or vinyl sulfonate, and the nucleophilic atom of a second molecule or ion may be part of a single molecule, rendering the bond-formation intramolecular.

In certain embodiments, an aryl halide or sulfonate is used, wherein its aryl moiety is a radical of an aromatic hydrocarbon (single or polycylic), such as benzene, naphthalene, anthracene and phenanthrene. In certain embodiments, the aryl halide may be selected from the group consisting of optionally-substituted phenyl halides.

In certain embodiments, a heteroaryl halide or sulfonate is used, wherein its heteroaryl moiety is a radical of an heteroaromatic (single or polycylic), such as pyrrole, thiophene, thianthrene, furan, pyran, isobenzofuran, chromene, xanthene, phenoxathiin, pyrrole, imidazole, pyrazole, thiazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, perimidine, phenanthroline, phenazine, phenarsazine, phenothiazine, furazan, phenoxazine, pyrrolidine, oxolane, thiolane, oxazole, piperidine, piperazine, morpholine.

In general, suitable aromatic compounds have the formula $Z_pArX$, wherein Ar is aryl or heteroaryl; and X is a sulfonate or a halogen selected from the group consisting of chlorine, bromine, and iodine. In certain embodiments, X is a halide selected from the group consisting of chlorine, bromine, and iodine. In certain embodiments, X represents a sulfonate moiety. Further, Z represents one or more optional substituents on the aromatic ring, though each occurence of Z (p>1) is independently selected. By way of example only, each incidence of substitution independently can be, as valence and stability permit, a halogen, a lower alkyl, a lower alkenyl, a lower alkynyl, a carbonyl (e.g., an ester, a carboxylate, or a formate), a thiocarbonyl (e.g., a thiolester, a thiolcarboxylate, or a thiolformate), an aldehyde, an amino, an acylamino, an amido, an amidino, a cyano, a nitro, an azido, a sulfonyl, a sulfoxido, a sulfate, a sulfonate, a sulfamoyl, a sulfonamido, a phosphoryl, a phosphonate, a phosphinate, $—(CH_2)_m—R_8$, $—(CH_2)_m—OH$, $—(CH_2)_m—$O-lower alkyl, $—(CH_2)_m—$O-lower alkenyl, $—(CH_2)_m—$O$—(CH_2)_n—R_8$, $—(CH_2)_m—SH$, $—(CH_2)_m—$S-lower alkyl, $—(CH_2)_m—$S-lower alkenyl, $—(CH_2)_m—$S$—(CH_2)_n—R_8$, or protecting groups of the above or a solid or polymeric support; $R_8$ represents a substituted or unsubstituted aryl, aralkyl, cycloalkyl, cycloalkenyl, or heterocycle; and n and m are independently for each occurrence zero or an integer in the range of 1 to 6. When the aryl moiety is phenyl, p is in the range of 0 to 5. For fused rings, where the number of potential substitution sites on the aryl moiety is greater than five, the range defined for p must be adjusted appropriately.

Reaction Conditions

The methods of the present invention may be performed under a wide range of conditions, though it will be understood that the solvents and temperature ranges recited herein are not limitative and only correspond to a preferred mode of the process of the invention.

In general, it will be desirable that reactions are run using mild conditions which will not adversely affect the reactants, the catalyst, or the product. For example, the reaction temperature influences the speed of the reaction, as well as the stability of the reactants, products and catalyst.

In certain embodiments, the methods of the present invention are conducted at a temperature less than about 150 C. In certain embodiments, the methods of the present invention are conducted at a temperature less than about 140 C. In certain embodiments, the methods of the present invention are conducted at a temperature less than about 110 C. In certain embodiments, the methods of the present invention are conducted at a temperature less than about 100 C. In certain embodiments, the methods of the present invention are conducted at a temperature less than about 90 C.

In general, the subject reactions are carried out in a liquid reaction medium. The reactions may be run without addition of solvent. Alternatively, the reactions may be run in an inert solvent, preferably one in which the reaction ingredients, including the catalyst, are substantially soluble. Suitable solvents include ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, xylene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents.

The invention also contemplates reaction in a biphasic mixture of solvents, in an emulsion or suspension, or reaction in a lipid vesicle or bilayer. In certain embodiments, it may be preferred to perform the catalyzed reactions in the solid phase with one of the reactants anchored to a solid support.

In certain embodiments it is preferable to perform the reactions under an inert atmosphere of a gas such as nitrogen or argon.

The reaction processes of the present invention can be conducted in continuous, semi-continuous or batch fashion and may involve a liquid recycle operation as desired. The processes of this invention are preferably conducted in batch fashion. Likewise, the manner or order of addition of the reaction ingredients, catalyst and solvent are also not generally critical to the success of the reaction, and may be accomplished in any conventional fashion.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the metal catalyst. When complete conversion is not desired or not obtainable, the starting materials can be separated from the product and then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, one or more of the reactants or the catalyst can be immobilized by attachment to or incorporation into a polymer or other insoluble matrix.

Subsequent Transformations

A product synthesized by a method of the present invention may be either an end-product or an intermediate in a synthesis scheme. In cases where the product synthesized by a method of the present invention is an intermediate, the product may be subjected to one or more additional transformations to yield the desired end-product. The set of additional transformations contemplated comprises isomerizations, hydrolyses, oxidations, reductions, additions, eliminations, olefinations, functional group interconversions, transition metal-mediated reactions, transition metal-catalyzed reactions, bond-forming reactions, cleavage reactions, fragmentation reactions, thermal reactions, photochemical reactions, cycloadditions, sigmatropic rearrangements, electrocyclic reactions, chemoselective reactions, regioselective reactions, stereoselective reactions, diastereoselective reactions, enantioselective reactions, and kinetic resolutions. The invention expressly comprises use of a method of the present invention as a step—either initial, intermediate or final—in the synthesis of known or new pharmaceuticals, e.g., antivirals, antibiotics, and analgesics.

Combinatorial Libraries

The subject methods of the present invention readily lend themselves to the creation of combinatorial libraries of compounds for the screening of pharmaceutical, agrochemical or other biological or medical activity or material-related qualities. A combinatorial library for the purposes of the present invention is a mixture of chemically related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property may be done by conventional methods.

Diversity in a library can be created at a variety of different levels. For instance, the substrate aryl groups used in a combinatorial approach can be diverse in terms of the core aryl moiety, e.g., a variegation in terms of the ring structure, and/or can be varied with respect to the other substituents.

A variety of techniques are available in the art for generating combinatorial libraries of small organic molecules. See, for example, Blondelle et al. (1995) *Trends Anal. Chem.* 14:83; the Affymax U.S. Pat. Nos. 5,359,115 and 5,362,899: the Ellman U.S. Pat. No. 5,288,514: the Still et al. PCT publication WO 94/08051; Chen et al. (1994) *JACS* 116:2661: Kerr et al. (1993) *JACS* 115:252; PCT publications WO92/10092, WO93/09668 and WO91/07087; and the Lerner et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO 94/08051, e.g., being linked to a polymer bead by a hydrolyzable or photolyzable group, e.g., located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay.

Exemplification

The invention now being generally described, it will be more readily understood by reference to the following examples which are included merely for purposes of illustration of certain aspects and embodiments of the present invention, and are not intended to limit the invention.

EXAMPLE 1

General Procedure for Cu-Catalyzed Carbon-Sulfur Bond Formation (See FIGS. 1–3)

Cu(I) iodide (10 mg, 0.05 mmol), potassium carbonate (276 mg, 2.0 mmol) and aryl iodide (1.0 mmol, if a solid at ambient temperature) were added to a screw-capped test tube with a Teflon-lined septum. The tube was evacuated and backfilled with argon (3 cycles). 2-Propanol (1.0 mL, bench top grade solvent without degassing and pre-drying), ethylene glycol (111 μL, 2.0 mmol, bench top grade solvent), aryl iodide (1.0 mmol, if a liquid at ambient temperature) and thiols (1.0 mmol) were added by syringes at room temperature. The tube was heated to 80° C. and stirred for 18–22 hours. The reaction mixture was then allowed to reach room temperature. Ethyl acetate (approx. 5 mL) and dodecane (227 μL, GC standard) were added. The aliquot was analyzed by GC. The reaction mixture was then filtered and concentrated. The crude product was purified by column chromatography on silica gel to afford the desired thioether. See FIGS. 1–3.

EXAMPLE 2

Figure 4:
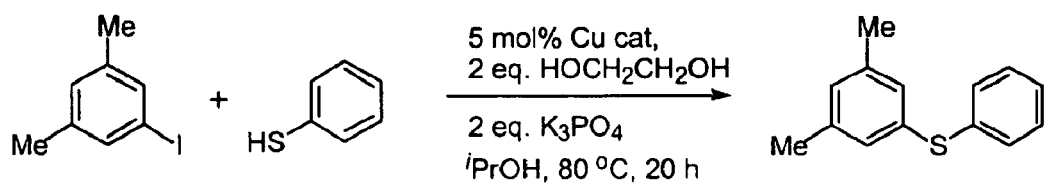
FIG. 4 tabulates examples of the copper-catalyzed arylation of thiophenol with 3,5-dimethylphenyl iodide using various copper catalysts.

Cu-Catalyst Screening for Cu-Catalyzed Carbon-Sulfur Bond Formation (See FIG. 4)

Copper complex (0.05 mmol) and potassium carbonate (276 mg, 2.0 mmol) were added to a screw-capped test tube with a Teflon-lined septum. The tube was evacuated and backfilled with argon (3 cycles). 2-Propanol (1.0 mL, bench top grade solvent without degassing or pre-drying), ethylene glycol (111 μL, 2.0 mmol, bench top grade solvent) and 5-iodo-m-xylene (144 μL, 1.0 mmol), thiophenol (103 μL, 1.0 mmol) were added by syringes at room temperature. The tube was heated to 80° C. and stirred for 20 hours. The reaction mixture was then allowed to reach room temperature. Ethyl acetate (approx. 5 mL) and dodecane (227 μL, GC standard) were added. The aliquot was analyzed by GC or GC-MS. See FIG. 4.

EXAMPLE 3

Figure 5:
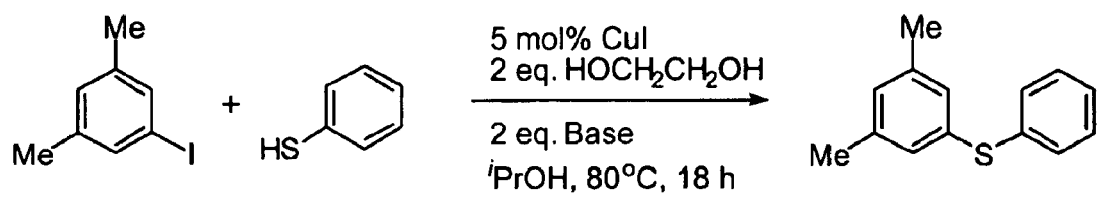
FIG. 5 tabulates examples of the copper-catalyzed arylation of thiophenol with 3,5-dimethylphenyl iodide using various bases.

Base Screening in Cu-Catalyzed Carbon-Sulfur Bond Formation (See FIG. 5)

Copper(I) iodide (10 mg, 0.05 mmol) and base (2.0 mmol, if solid) were added to a screw-capped test tube with a Teflon-lined septum. The tube was evacuated and backfilled with argon (3 cycles). 2-Propanol (1.0 mL, bench top grade solvent without degassing and pre-drying), ethylene glycol (111 μL, 2.0 mmol, bench top grade solvent), base (2.0 mmol, if liquid) and 5-iodo-m-xylene (144 μL, 1.0 mmol), thiophenol (103 μL, 1.0 mmol) were added by syringes at room temperature. The tube was heated to 80° C. and stirred for 20 hours. The reaction mixture was then allowed to reach room temperature. Ethyl acetate (approx. 5 mL) and dodecane (227 μL, GC standard) were added. The aliquot was analyzed by GC. See FIG. 5.

EXAMPLE 4

Figure 6:
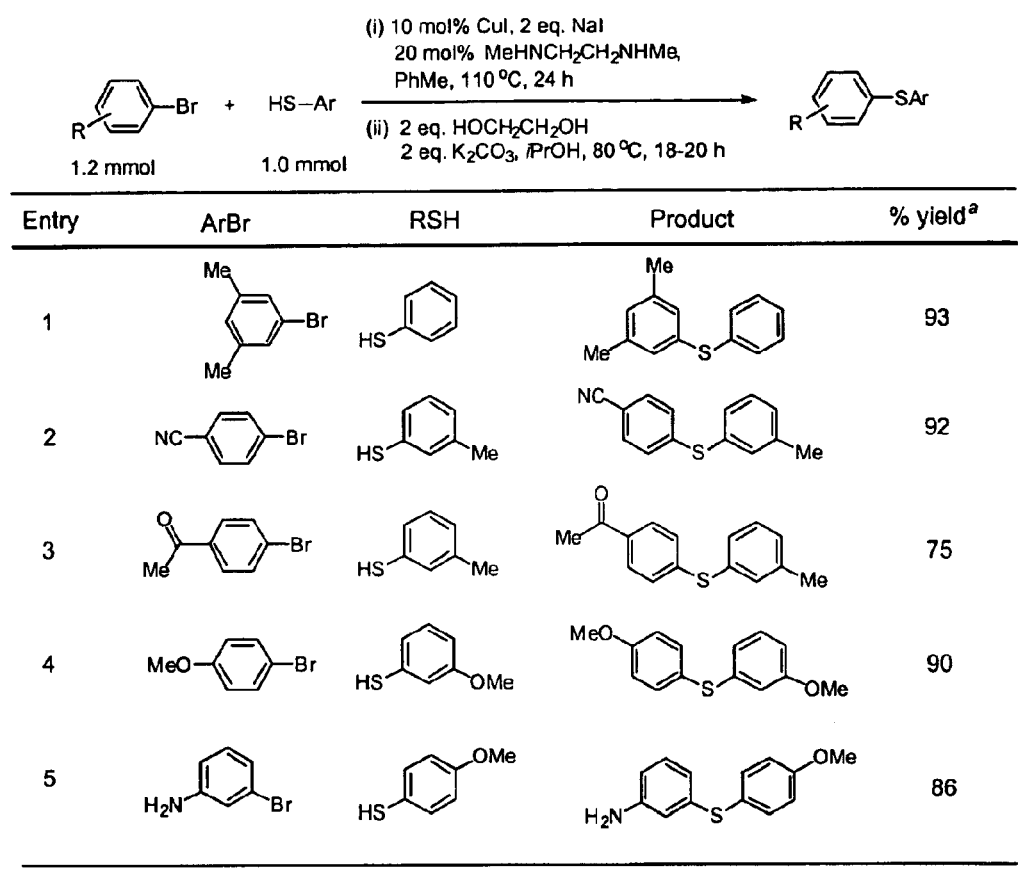
FIG. 6 tabulates examples of the copper-catalyzed arylation of thiophenols using aryl bromides.

Cu-Catalyzed Carbon-Sulfur Bond Formation from Aryl Bromides (See FIG. 6)

Copper(I) iodide (19 mg, 0.1 mmol), sodium iodide (300 mg, 2.0 mmol) and aryl bromide (1.2 mmol, if solid) were added to a screw-capped test tube with a Teflon-lined septum. The tube was evacuated and backfilled with argon (3 cycles). Dry toluene (1 mL), aryl bromide (1.2 mmol, if liquid) and N,N'-dimethylethylenediamine (0.2 mmol) were added by syringes at room temperature. The reaction was stirred to 110° C. for 24 hours. The reaction mixture was allowed to room temperature and the solvent was removed in vacuo. 2-Propanol (1.0 mL, bench top grade without degassing and pre-drying), ethylene glycol (111 μL, bench top grade), aryl thiol (1.0 mmol) and potassium carbonate (276 mg, 2.0 mmol) were added at room temperature. The reaction was heated to 80° C. and stirred for 18–20 hours. The reaction was allowed to reach room temperature. Ethyl acetate (approx. 5 mL) and dodecane (227 μL, GC standard) were added. The organic phase was analyzed by GC and GC-MS. The reaction was then filtered and concentrated. The crude product was purified by column chromatography on silica gel to afford the desired diaryl sulfide product. See FIG. 6.

EXAMPLE 5

Cu-Catalyzed Conversion of Aryl Bromides into Aryl Iodides (See FIG. 7)

A Schlenk tube was charged with CuI (9.6 mg, 0.0504 mmol, 5.0 mol %), aryl bromide (if it is a solid; 1.00 mmol), NaI (300 mg, 2.00 mol), briefly evacuated and backfilled with argon. trans-N,N'-Dimethyl-1,2-cyclohexanediamine (16 μL, 0.10 mmol, 10 mol %), aryl bromide (if it is a liquid; 1.00 mmol), and dioxane (1.0 mL) were added under argon. The Schlenk tube was sealed with a Teflon valve and the reaction mixture was stirred at 110° C. for 22–23 h. The resulting suspension was allowed to reach room temperature, diluted with 30% aq ammonia (5 mL), poured into water (20 mL), and extracted with dichloromethane (3×15 mL). The combined organic phases were dried (MgSO$_4$ or Na$_2$SO$_4$), concentrated, and the residue was purified by flash chromatography on silica gel to provide the desired product.

5-Iodoindole (FIG. 7, Entry 1)

Following the general procedure, 5-bromoindole (197 mg, 1.00 mmol) was converted into 5-iodoindole. Purification of the crude product by column chromatography on silica gel (hexane-ethyl acetate 10:1 followed by hexane-ethyl acetate 3:1) provided the desired product as a white solid (238 mg, 98% yield).

3-Iodoquinoline (FIG. 7, Entry 2)

Following the general procedure, 3-bromoquinoline (136 μL, 1.00 mmol) was converted into 3-iodoquinoline. Purification of the crude product by column chromatography on silica gel (hexane-ethyl acetate 8:1) provided the desired product as a white solid (248 mg, 97% yield).

3-Iodopropiophenone (FIG. 7, Entry 3)

Following the general procedure, 3-bromopropiophenone (214 mg, 1.00 μmmol) was converted into 3-iodopropiophenone. Purification of the crude product by column chromatography on silica gel (hexane-ethyl acetate 10:1) provided the desired product as a colorless oil (256 mg, 98% yield).

4-Iodo-2-nitrotoluene (FIG. 7, Entry 4)

Following the general procedure, 4-bromo-2-nitrotoluene (216 mg, 1.00 mmol) was converted into 4-iodo-2-nitrotoluene. Purification of the crude product by column chromatography on silica gel (hexane-ethyl acetate 10:1) provided the desired product as pale yellow fine needles (249 mg, 95% yield).

1-(4-Iodophenyl)-1-(2-pyridyl)-3-dimethylaminopropane (FIG. 7, Entry 5)

Following the general procedure, 1-(4-bromophenyl)-1-(2-pyridyl)-3-dimethylaminopropane (256 µL, 1.00 mmol) was converted into 1-(4-iodophenyl)-1-(2-pyridyl)-3-dimethylaminopropane. Purification of the crude product by column chromatography on silica gel (dichloromethane-dichloromethane (saturated with 30% aq ammonia)-methanol 30:20:2) provided the desired product as a pale tan oil (365 mg, 100% yield).

N-Allyl-4-iodobenzenesulfonamide (FIG. 7, Entry 6)

Following the general procedure, N-allyl-4-bromobenzenesulfonamide (277 mg, 1.00 mmol) was converted into N-allyl-4-iodobenzenesulfonamide. Purification of the crude product by column chromatography on silica gel (hexane-ethyl acetate 4:1) provided the desired product as white crystals (309 mg, 96% yield).

4-Iodophenylacetonitrile (FIG. 7, Entry 7)

Following the general procedure, 4-bromophenylacetonitrile (197 mg, 1.00 mmol) was converted into 4-iodophenylacetonitrile. Purification of the crude product by column chromatography on silica gel (hexane-ethyl acetate 5:1) provided the desired product as a tan solid (236 mg, 97% yield).

2-Amino-5-iodopyridine (FIG. 7, Entry 8)

Following the general procedure, 2-amino-5-bromopyridine (173 mg, 1.00 mmol) was converted into 2-amino-5-iodopyridine. Purification of the crude product by column chromatography on silica gel (hexane-ethyl acetate 2:3) provided the desired product as a pale tan solid (209 mg, 95% yield).

EXAMPLE 6

Preparation of 3-Iodobenzo[b]thiophene Using m-Xylene—Diglyme Solvent Mixture

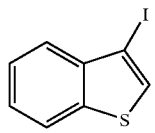

A Schlenk tube was charged with CuI (9.6 mg, 0.0504 mmol, 5.0 mol %), NaI (300 mg, 2.00 mmol), evacuated and backfilled with argon. trans-N,N'-Dimethyl-1,2-cyclohexanediamine (16 µL, 0.10 mmol, 10 mol %), 3-bromobenzo[b]thiophene (131 µL, 1.00 mmol), m-xylene (0.80 mL), and diglyme (0.20 mL) were added under argon. The Schlenk tube was sealed with a Teflon valve and the reaction mixture was stirred at 130° C. for 22 h. The resulting suspension was allowed to reach room temperature, diluted with hexane (10 mL), and filtered through silica gel (2×2 cm) eluting with hexane (50 mL). The filtrate was concentrated, and the residue was purified by flash chromatography on silica gel to provide 3-iodobenzo[b]thiophene (243 mg, 93% yield) as a pale yellow liquid.

EXAMPLE 7

Preparation of 3-Iodobenzoic Acid through an in situ Generated Trimethylsilyl Ester

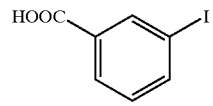

A Schlenk tube was charged with CuI (9.6 mg, 0.0504 mmol, 5.0 mol %), 3-bromobenzoic acid (210 mg, 1.00 mmol), NaI (300 mg, 2.00 mmol), evacuated and backfilled with argon. trans-N,N'-Dimethyl-1,2-cyclohexanediamine (16 µL, 0.10 mmol, 10 mol %), 1,1,1,3,3,3-hexamethyldisilazane (211 µL, 1.00 mmol), and dioxane (1.0 mL) were added under argon. The Schlenk tube was sealed with a Teflon valve and the reaction mixture was stirred at 110° C. for 23 h. The resulting suspension was allowed to reach room temperature, poured into 10% aq HCl (20 mL), and extracted with dichloromethane (3×15 mL). The combined organic phases were dried (Na$_2$SO$_4$) and concentrated. The residue was dissolved in dichloromethane (50 mL) and washed with an aqueous solution of 1% HCl and 1% Na$_2$SO$_3$. The aqueous phase was extracted with with dichloromethane (2×20 mL). The organic phases were combined, dried (Na$_2$SO$_4$) and concentrated. The solid residue was washed with hexane (3×15 mL) and dried to provide 3-iodobenzoic acid (222 mg, 90% yield) as white, fine needles.

EXAMPLE 8

Preparation of 2-Iodotoluene Using Various Iodide Sources

A Schlenk tube was charged with CuI (9.6 mg, 0.0504 mmol, 5.0 mol %), iodide source (2.00 mmol), evacuated and backfilled with argon. trans-N,N'-Dimethyl-1,2-cyclohexanediamine (16 µL, 0.10 mmol, 10 mol %), 2-bromotoluene (121 µL, 1.01 mmol), and dioxane (1.0 mL) were added under argon. The Schlenk tube was sealed with a Teflon valve and the reaction mixture was stirred at 110° C. for 23 h. The resulting suspension was allowed to reach room temperature. Ethyl acetate (2 mL) and dodecane (internal GC standard, 230 µL) were added to the reaction mixture. A 50 µL sample of the supernatant solution was diluted with ethyl acetate (1 mL) and analyzed by GC. The results are tabulated below.

| Entry | Iodide Source | Yield of 2-Iodotoluene |
| --- | --- | --- |
| 1 | LiI | 73% |
| 2 | NaI | 84% |
| 3 | KI | 82% |
| 4 | RbI | 80% |
| 5 | CsI | 65% |

EXAMPLE 9

Preparation of 5-Iodo-m-xylene Using Various Solvents

A Sclenk tube was charged with CuI (9.6 mg, 0.0504 mmol, 5.0 mol %), sodium iodide (fine powder, dried, 300 mg, 2.00 mmol), evacuated and backfilled with argon.

trans-N,N'-Dimethyl-1,2-cyclohexanediamine (16 µL, 0.10 mmol, 10 mol %), 5-bromo-m-xylene (136 µL, 1.00 mmol), and solvent (1.0 µL) were added under argon. The Schlenk tube was sealed with a Teflon valve and the reaction mixture was stirred at 110° C. for 23 h. The resulting suspension was allowed to reach room temperature. Ethyl acetate (2 mL) and dodecane (internal GC standard, 230 µL) were added to the reaction mixture. A 50 µL sample of the supernatant solution was diluted with ethyl acetate (1 mL) and analyzed by GC. The results are tabulated below.

| Entry | Solvent | Yield of 5-Iodo-m-xylene |
|---|---|---|
| 1 | Toluene | 98% |
| 2 | α,α,α-Trifluorotoluene | 49% |
| 3 | Dioxane | 99% |
| 4 | N-Methylpyrrolidinone | 49% |
| 5 | Sulfolane | 99% |
| 6 | tert-Amyl alcohol | 99% |

EXAMPLE 10

Preparation of 5-Iodo-m-xylene Using Various Amounts of the Catalyst

A Schlenk tube was charged with CuI, sodium iodide (fine powder, dried, 300 mg, 2.00 mmol), evacuated and backfilled with argon. N,N'-Dimethylethylenediamine, 5-bromo-m-xylene (136 µL, 1.00 mmol), and toluene (1.0 mL) were added under argon. The Schlenk tube was sealed with a Teflon valve and the reaction mixture was stirred at 110° C. for 22 h. The resulting suspension was allowed to reach room temperature. Ethyl acetate (2 mL) and dodecane (internal GC standard, 230 µL) were added to the reaction mixture. A 50 µL sample of the supernatant solution was diluted with ethyl acetate (1 mL) and analyzed by GC. The results are tabulated below.

| Entry | Amount of CuI | Amount of N,N'-Dimethylethylenediamine | Yield of 5-Iodo-m-xylene |
|---|---|---|---|
| 1 | 9.6 mg (0.050 mmol) | 11 µL (0.10 mmol) | 78% |
| 2 | 19.5 mg (0.102 mmol) | 11 µL (0.10 mmol) | 70% |
| 3 | 19.5 mg (0.102 mmol) | 21.5 µL (0.202 mmol) | 89% |
| 4 | 19.5 mg (0.102 mmol) | 107 µL (1.01 mmol) | 95% |
| 5 | 38.5 mg (0.202 mmol) | 43 µL (0.404 mmol) | 96% |

EXAMPLE 11

Figure 8:
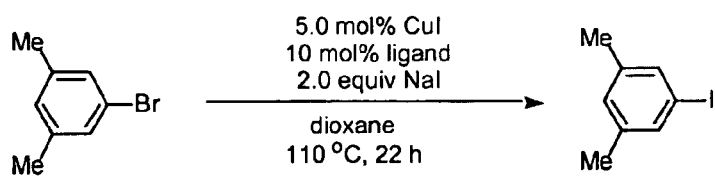
FIG. 8 tabulates examples of the copper-catalyzed formation of 3,5-dimethylphenyl iodide from 3,5-dimethylphenyl bromide using various ligands.

Preparation of 5-Iodo-m-xylene Using Various Ligands (See FIG. 8)

Thirteen test tubes with screw threads were charged with CuI (9.6 mg, 0.0504 mmol, 5.0 mol %), sodium iodide (300 mg, 2.00 mmol), evacuated and backfilled with argon. Meanwhile, a stock solution of 5-bromo-m-xylene (2.04 mL, 15.0 mmol) and dodecane (0.68 mL) in dioxane (15 mL) was prepared. To each test tube was added 1.18 mL of the stock solution and 0.10 mmol of ligand. The reaction mixtures in the sealed test tubes were stirred at 110° C. for 22 h. The resulting suspensions were allowed to reach room temperature. Ethyl acetate (2 mL) was added to each reaction mixture. A 50 µL sample of the supernatant solution was diluted with ethyl acetate (1 mL) and analyzed by GC. See FIG. 8.

EXAMPLE 12

Preparation of 4-Iodotoluene from 4-Chlorotoluene

A Schlenk tube was charged with CuI (77 mg, 0.404 mmol, 10 mol %), NaI (915 mg, 6.10 mmol), evacuated and backfilled with argon. trans-N,N'-Dimethyl-1,2-cyclohexanediamine (126 µL, 0.802 mmol, 20 mol %), 4-chlorotoluene (0.48 mL, 4.05 mmol), and diglyme (0.50 mL) were added under argon. The Schlenk tube was sealed with a Teflon valve and the reaction mixture was stirred at 130° C. for 22 h. The resulting suspension was allowed to reach room temperature. Ethyl acetate (3 mL) and dodecane (internal GC standard, 230 µL) were added to the reaction mixture. A 50 µL sample of the supernatant solution was diluted with ethyl acetate (1 mL) and analyzed by GC to provide 25% yield of 4-iodotoluene.

EXAMPLE 13

Preparation of 4-Bromotoluene from 4-Chlorotoluene

A Schlenk tube was charged with CuBr (29 mg, 0.202 mmol, 10 mol %), KBr (240 mg, 2.02 mmol), evacuated and backfilled with argon. trans-N,N'-Dimethyl-1,2-cyclohexanediamine (63 µL, 0.401 mmol, 20 mol %), and 4-chlorotoluene (0.95 µL, 8.01 mmol) were added under argon. The Schlenk tube was sealed with a Teflon valve and the reaction mixture was stirred at 150° C. for 40 h. The resulting suspension was allowed to reach room temperature. Ethyl acetate (3 mL) and dodecane (internal GC standard, 460 µL) were added to the reaction mixture. A 50 µL sample of the supernatant solution was diluted with ethyl acetate (1 mL) and analyzed by GC to provide 35% yield of 4-bromotoluene.

EXAMPLE 14

Benzo[b]thiophene-3-carbonitrile

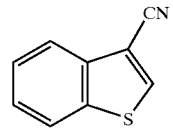

An oven dried screw cap test tube was charged with NaCN (60 mg, 1.225 mmol), dried KI (34 mg, 0.205 mmol, 20 mol %) and CuI (20 mg, 0.105 mmol, 10 mol %), evacuated and backfilled with argon three times. 3-Bromo-benzo[b]thiophene (135 µL, 1.032 mmol), N,N'-dimethylethylenediamine (110 µL, 1.033 mmol) and anhydrous toluene (700 µL) were added under argon. The tube was sealed and the reaction mixture was stirred magnetically at 110° C. for 24 h. The resulting suspension was cooled to room temperature, 2 mL of ethyl acetate, 1 mL of ammonium hydroxide (30%) and 1 mL of water were added. The mixture was stirred at 25° C. for 10 min, then the organic layer was separated and the aqueous layer was extracted three times with ethyl acetate (3×2 mL). The combined organic layers were washed with 5 mL of water and dried over MgSO₄. The solvent was removed at reduced pressure. Purification of the residue by flash chromatography on silica gel (2×15 cm; hexane/ethyl acetate 10:1) provided 122 mg (74% yield) of the title compound as a pale yellow solid.

EXAMPLE 15

1-(Toluene-4-sulfonyl)-indole-5-carbonitrile

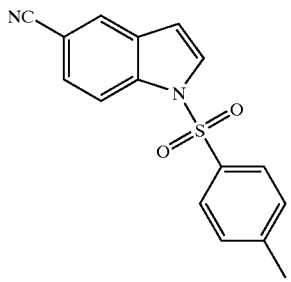

An oven dried screw cap test tube was charged with NaCN (106 mg, 2.163 mmol), dried KI (60 mg, 0.361 mmol, 20 mol %), CuI (34 mg, 0.178 mmol, 10 mol %), 5-bromo-1-(toluene-4-sulfonyl)-1H-indole (630 mg, 1.803 mmol), evacuated and backfilled with argon three times. N,N'-dimethylethylenediamine (195 μL, 1.832 mmol) and anhydrous toluene (1.1 mL) were added under argon. The tube was sealed and the reaction mixture was stirred magnetically at 110° C. for 24 h. The resulting yellow suspension was cooled to room temperature, 2 mL of ethyl acetate, 1 mL of ammonium hydroxide (30%) and 1 mL of water were added. The mixture was stirred at 25° C. for 10 min, then the organic layer was separated and the aqueous layer was extracted three times with ethyl acetate (3×2 mL). The organic layers combined were washed with 5 mL of water and dried over MgSO$_4$. The solvent was removed at reduced pressure. Purification of the residue by flash chromatography on silica gel (2×15 cm; hexane/ethyl acetate 10:1) provided 459 mg (86% yield) of the title compound as a white solid.

EXAMPLE 16

Naphthalene-1-carbonitrile

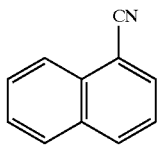

From 1-Bromonaphthalene

An oven dried screw cap test tube was charged with NaCN (127 mg, 2.592 mmol), dried KI (72 mg, 0.434 mmol, 20 mol %) and CuI (41 mg, 0.215 mmol, 10 mol %), evacuated and backfilled with argon three times. 1-Bromonaphthalene (300 μL, 2.157 mmol), N,N'-dimethylethylenediamine (230 μL, 2.16 mmol) and anhydrous toluene (1.4 mL) were added under argon. The tube was sealed and the reaction mixture was stirred magnetically at 110° C. for 24 h. The resulting yellow suspension was cooled to room temperature, 2 mL of ethyl acetate, 1 mL of ammonium hydroxide (30%) and 1 mL of water were added. The mixture was stirred at 25° C. for 10 min, then the organic layer was separated and the aqueous layer was extracted three times with ethyl acetate (3×2 mL). The combined organic layers were washed with 5 mL of water and dried over MgSO$_4$. The solvent was removed at reduced pressure. Purification of the residue by flash chromatography on silica gel (2×15 cm; hexane/ethyl acetate 10:1) provided 232 mg (70% yield) of the title compound as a colorless oil.

From 1-Iodonaphthalene

An oven dried screw cap test tube was charged with NaCN (96 mg, 1.959 mmol) and CuI (31 mg, 0.163 mmol, 10 mol %), evacuated and backfilled with argon three times. 1-Iodonaphthalene (240 μL, 1.64 mmol), N,N'-dimethylethylenediamine (175 μL, 1.644 mmol) and anhydrous toluene (1 mL) were added under argon. The tube was sealed and the reaction mixture was stirred magnetically at 110° C. for 24 h. The resulting yellow suspension was cooled to room temperature, 2 mL of ethyl acetate, 1 mL of ammonium hydroxide (30%) and 1 mL of water were added. The mixture was stirred at 25° C. for 10 min, then the organic layer was separated and the aqueous layer was extracted three times with ethyl acetate (3×2 mL). The combined organic layers were washed with 5 mL of water and dried over MgSO$_4$. The GC analysis showed complete consumption of starting material, and formation of the title compound (confirmed by GC-MS).

EXAMPLE 17

Biphenyl-2-carbonitrile

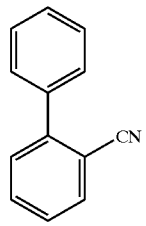

An oven dried screw cap test tube was charged with NaCN (93 mg, 1.898 mmol), dried KI (52 mg, 0.313 mmol, 20 mol %) and CuI (29 mg, 0.152 mmol, 10 mol %), evacuated and backfilled with argon three times. 2-Bromobiphenyl (270 μL, 1.566 mmol), N,N'-dimethylethylenediamine (170 μL, 1.597 mmol) and anhydrous toluene (1 mL) were added under argon. The tube was sealed and the reaction mixture was stirred magnetically at 110° C. for 24 h. The resulting yellow suspension was cooled to room temperature, 2 mL of ethyl acetate, 1 mL of ammonium hydroxide (30%) and 1 mL of water were added. The mixture was stirred at 25° C. for 10 min, then the organic layer was separated and the aqueous layer was extracted three times with ethyl acetate (3×2 mL). The combined organic layers were washed with 5 mL of water and dried over MgSO$_4$. The solvent was removed at reduced pressure. Purification of the residue by flash chromatography on silica gel (2×15 cm; hexane/ethyl acetate 10:1) provided 190 mg (68% yield) of the title compound as a colorless oil.

EXAMPLE 18

Quinoline-3-carbonitrile

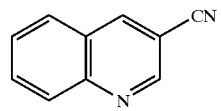

An oven dried screw cap test tube was charged with NaCN (98 mg, 2.0 mmol), dried KI (32 mg, 0.168 mmol, 20 mol %) and CuI (56 mg, 0.337 mmol, 10 mol %), evacuated and backfilled with argon three times. 3-Bromoquinoline (225 μL, 1.66 mmol), N,N'-dimethylethylenediamine (180 μL, 1.69 mmol) and anhydrous toluene (1 mL) were added under argon. The tube was sealed and the reaction mixture was stirred magnetically at 110° C. for 24 h. The resulting yellow suspension was cooled to room temperature, 2 mL of ethyl acetate, 1 mL of ammonium hydroxide (30%) and 1 mL of water were added. The mixture was stirred at 25° C. for 10 min, then the organic layer was separated and the aqueous layer was extracted three times with ethyl acetate (3×2 mL). The combined organic layers were washed with 5 mL of water and dried over MgSO$_4$. The solvent was removed at reduced pressure. Purification of the residue by flash chromatography on silica gel (2×15 cm; hexane/ethyl acetate 10:1) provided 188 mg (74% yield) of the title compound as a white solid.

EXAMPLE 19

3,5-Dimethylbenzonitrile

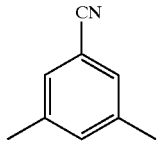

Method A: KI in a Sealed Tube

An oven dried screw cap test tube was charged with NaCN (59 mg, 1.20 mmol), dried KI (33 mg, 0.199 mmol, 20 mol %) and CuI (20 mg, 0.105 mmol, 10 mol %), evacuated and backfilled with argon three times. 1-Bromo-3,5-dimethylbenzene (135 μL, 0.994 mmol), N,N'-dimethylethylenediamine (110 μL, 1.033 mmol) and anhydrous toluene (650 μL) were added under argon. The tube was sealed and the reaction mixture was stirred magnetically at 110° C. for 24 h. The resulting yellow suspension was cooled to room temperature, 2 mL of ethyl acetate, 150 μL of n-dodecane as internal standard, 1 mL of ammonium hydroxide (30%) and 1 mL of water were added. The mixture was stirred at 25° C. for 10 min then the organic layer was washed with 1 mL of water and dried over MgSO$_4$. The GC analysis showed a conversion of 90% with a 86% yield of the title product, calculated vs internal standard.

Method B: NaI in a Sealed Tube

An oven dried screw cap test tube was charged with NaCN (88 mg, 1.796 mmol), dried NaI (44 mg, 0.294 mmol, 20 mol %) and CuI (28 mg, 0.147 mmol, 10 mol %), evacuated and backfilled with argon three times. 1-Bromo-3,5-dimethylbenzene (200 μL, 1.472 mmol), N,N'-dimethylethylenediamine (160 μL, 1.503 mmol) and anhydrous toluene (1 mL) were added under argon. The tube was sealed and the reaction mixture was stirred magnetically at 110° C. for 24 h. The resulting yellow suspension was cooled to room temperature, 2 mL of ethyl acetate, 1 mL of ammonium hydroxide (30%) and 1 mL of water were added. The mixture was stirred at 25° C. for 10 min then the organic layer was washed with 1 mL of water and dried over MgSO$_4$. The GC analysis showed essentially complete consumption of the starting material, and formation of the title compound (confined by GC-MS).

Method C: KI Under Reflux for 36 h

An oven dried three necked 50 mL round bottom flask was charged with NaCN (1.127 g, 23 mmol), dried KI (630 mg, 3.8 mmol, 20 mol %), evacuated and backfilled with argon three times. Anhydrous toluene (10 mL), 1-bromo-3,5-dimethylbenzene (2.6 mL, 19 mmol), were added under argon. In a separate oven dried flask, CuI (360 mg, 1.9 mmol, 10 mol %) was mixed under stirring with N,N'-dimethylethylenediamine (2 mL, 19 mmol). The resulting dark-green mixture was diluted with anhydrous toluene (2 mL) and added, under vigorous stirring at 25° C., to the mixture containing aryl bromide. The obtained reaction mixture was magnetically stirred under reflux in an argon atmosphere, at 110° C. for 36 h. The resulting yellow suspension was cooled to room temperature. 50 μL of the mixture were diluted with 0.5 mL of ethyl acetate and treated with 0.5 mL of ammonium hydroxide (30%) and water. The resulting organic layer was washed with 1 mL of water and dried over MgSO$_4$. The GC analysis showed essentially complete consumption of the starting material, and formation of the title compound (confirmed by GC-MS).

Method D: Benzotrifluoride as a Solvent at 102° C. in a Sealed Tube

An oven dried screw cap test tube was charged with NaCN (73 mg, 1.489 mmol), dried KI (42 mg, 0.253 mmol, 20 mol %) and CuI (24 mg, 0.126 mmol, 10 mol %), evacuated and backfilled with argon three times. 1-Bromo-3,5-dimethylbenzene (170 μL, 1.251 mmol), N,N'-dimethylethylenediamine (135 μL, 1.271 mmol) and anhydrous benzotrifluoride (825 μL) were added under argon. The tube was sealed and the reaction mixture was stirred magnetically at 102° C. for 24 h. The resulting yellow suspension was cooled to room temperature, 2 mL of ethyl acetate, 1 mL of ammonium hydroxide (30%) and 1 mL of water were added. The mixture was stirred at 25° C. for 10 min, then the organic layer was washed with 1 mL of water and dried over MgSO$_4$. The GC analysis showed complete consumption of the starting material, and formation of the title compound (confirmed by GC-MS).

EXAMPLE 20

2,5-Dimethylbenzonitrile

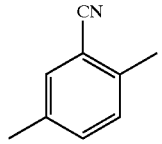

From 2-Bromo-1,4-dimethylbenzene

An oven dried screw cap test tube was charged with NaCN (93 mg, 1.898 mmol), dried KI (52 mg, 0.313 mmol, 20 mol %) and CuI (30 mg, 0.158 mmol, 10 mol %), evacuated and backfilled with argon three times. 2-Bromo-1,4-dimethylbenzene (215 μL, 1.557 mmol), N,N'-dimethylethylenediamine (165 μL, 1.549 mmol) and anhydrous toluene (1 mL) were added under argon. The tube was sealed and the reaction mixture was stirred magnetically at 110° C. for 24 h. The resulting yellow suspension was cooled to room temperature, 2 mL of ethyl acetate, 1 mL of ammonium hydroxide (30%) and 1 mL of water were added. The mixture was stirred at 25° C. for 10 min, then the organic layer was washed with 1 mL of water and dried over MgSO$_4$. The GC analysis showed consumption of the majority of the starting material, and formation of the title compound (as confirmed by GC-MS).

From 2-Iodo-1,4-dimethylbenzene

An oven dried screw cap test tube was charged with NaCN (84 mg, 1.71 mmol) and CuI (27 mg, 0.142 mmol, 10 mol %), evacuated and backfilled with argon three times. 2-Iodo-1,4-dimethylbenzene (205 μL, 1.413 mmol), N,N'- dimethylethylenediamine (150 µL, 1.409 mmol) and anhydrous toluene (900 µL) were added under argon. The tube was sealed and the reaction mixture was stirred magnetically at 110° C. for 24 h. The resulting yellow suspension was cooled to room temperature, 2 mL of ethyl acetate, 150 µL of n-dodecane, as internal standard, 1 mL of ammonium hydroxide (30%) and 1 mL of water were added. The mixture was stirred at 25° C. for 10 min, then the organic layer was separated, washed with 1 mL of water and dried over MgSO$_4$. The GC analysis showed complete conversion of starting material with a yield of title product calculated vs internal standard of 86%.

EXAMPLE 21

3-Trifluoromethylbenzonitrile

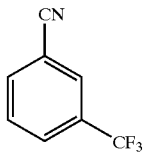

An oven dried screw cap test tube was charged with NaCN (125 mg, 2.551 mmol), dried KI (60 mg, 0.361 mmol, 17 mol %) and CuI (40 mg, 0.210 mmol, 10 mol %), evacuated and backfilled with argon three times. 1-Bromo-3-trifluoromethylbenzene (295 µL, 2.115 mmol), N,N'-dimethylethylenediamine (225 µL, 2.110 mmol) and anhydrous toluene (1.4 mL) were added under argon. The tube was sealed and the reaction mixture was stirred magnetically at 110° C. for 24 h. The resulting yellow suspension was cooled to room temperature, 2 mL of ethyl acetate, 1 mL of ammonium hydroxide (30%) and 1 mL of water were added. The mixture was stirred at 25° C. for 10 min, then the organic layer was washed with 1 mL of water and dried over MgSO$_4$. The GC analysis showed essentially complete consumption of the starting material, and formation of the title compound (as confirmed by GC-MS).

EXAMPLE 22

3,4-Dimethoxybenzonitrile

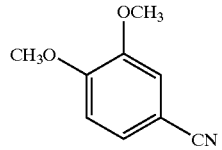

An oven dried screw cap test tube was charged with NaCN (107 mg, 2.184 mmol), dried KI (60 mg, 0.361 mmol, 20 mol %) and CuI (34 mg, 0.210 mmol, 10 mol %), evacuated and backfilled with argon three times. 1-Bromo-3,4-dimethoxybenzene (260 µL, 1.807 mmol), N,N'-dimethylethylenediamine (195 µL, 1.832 mmol) and anhydrous toluene (1.2 mL) were added under argon. The tube was sealed and the reaction mixture was stirred magnetically at 110° C. for 24 h. The resulting yellow suspension was cooled to room temperature, 2 mL of ethyl acetate, 1 mL of ammonium hydroxide (30%) and 1 mL of water were added. The mixture was stirred at 25° C. for 10 min, then the organic layer was washed with 1 mL of water and dried over MgSO$_4$. The GC analysis showed complete conversion of starting material with formation of the title product (confirmed by GC-MS).

EXAMPLE 23

Nicotinonitrile

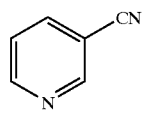

An oven dried screw cap test tube was charged with NaCN (129 mg, 2.633 mmol), dried KI (72 mg, 0.433 mmol, 20 mol %) and CuI (42 mg, 0.220 mmol, 10 mol %), evacuated and backfilled with argon three times. 3-Bromopyridine (210 µL, 1.180 mmol), N,N'-dimethylethylenediamine (235 µL, 2.207 mmol) and anhydrous toluene (1.4 mL) were added under argon. The tube was sealed and the reaction mixture was stirred magnetically at 110° C. for 24 h. The resulting yellow suspension was cooled to room temperature, 2 mL of ethyl acetate, 1 mL of ammonium hydroxide (30%) and 1 mL of water were added. The mixture was stirred at 25° C. for 10 min then the organic layer was washed with 1 mL of water and dried over MgSO$_4$. The GC analysis showed complete conversion of starting material with formation of the title product (confirmed by GC-MS).

EXAMPLE 24

Furan-3-carbonitrile

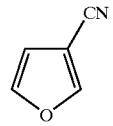

An oven dried screw cap test tube was charged with NaCN (53 mg, 1.083 mmol), dried KI (30 mg, 0.181 mmol, 20 mol %) and CuI (17 mg, 0.089 mmol, 10 mol %), evacuated and backfilled with argon three times. 3-Bromofuran (88 µL, 0.896 mmol), N,N'-dimethylethylenediamine (100 µL, 0.939 mmol) and anhydrous toluene (600 µL) were added under argon. The tube was sealed and the reaction mixture was stirred magnetically at 110° C. for 24 h. The resulting red suspension was cooled to room temperature, 2 mL of ethyl acetate, 1 mL of ammonium hydroxide (30%) and 1 µL of water were added. The mixture was stirred at 25° C. for 10 min, then the organic layer was washed with 1 mL of water and dried over MgSO$_4$. The GC analysis showed essentially complete consumption of the starting material, and formation of the title compound (as confirmed by GC-MS).

EXAMPLE 25

Thiophene-3-carbonitrile

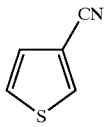

An oven dried screw cap test tube was charged with NaCN (76 mg, 1.551 mmol), dried KI (43 mg, 0.126 mmol, 20 mol %) and CuI (24 mg, 0.126 mmol, 10 mol %), evacuated and backfilled with argon three times. 3-Bromothiophene (120 µL, 1.282 mmol), N,N'-dimethylethylenediamine (140 µL, 1.315 mmol) and anhydrous toluene (850 µL) were added under argon. The tube was sealed and the reaction mixture was stirred magnetically at 110° C. for 24 h. The resulting red suspension was cooled to room temperature, 2 mL of ethyl acetate, 150 µL of n-dodecane, 1 mL of ammonium hydroxide (30%) and 1 mL of water were added. The mixture was stirred at 25° C. for 10 min, then the organic layer was washed with 1 mL of water and dried over MgSO$_4$. The GC analysis showed consumption of the majority of the starting material, and formation of the title compound.

EXAMPLE 26

4-Benzoylbenzonitrile

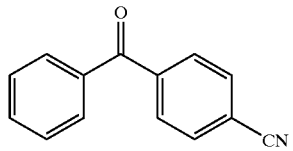

An oven dried screw cap test tube was charged with NaCN (91 mg, 1.857 mmol), dried KI (51 mg, 0.307 mmol, 20 mol %), CuI (30 mg, 0.157 mmol, 10 mol %), (4-bromophenyl)-phenyl-methanone (404 mg, 1.548 mmol), evacuated and backfilled with argon three times. N,N'-dimethylethylenediamine (165 µL, 1.550 mmol) and anhydrous toluene (1 mL) were added under argon. The tube was sealed and the reaction mixture was stirred magnetically at 110° C. for 24 h. The resulting suspension was cooled to room temperature, 2 mL of ethyl acetate, 1 mL of ammonium hydroxide (30%) and 1 mL of water were added. The mixture was stirred at 25° C. for 10 min then the organic layer was washed with 1 mL of water and dried over MgSO$_4$. The GC analysis showed complete conversion of starting material with formation of title product (confirmed by GC-MS).

EXAMPLE 27

1-(3,5-Dimethylphenyl)-pyrrolidin-2-one

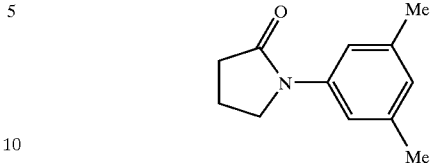

An oven-dried Schlenk flask was evacuated and backfilled with argon. The flask was charged with bis(trans-N,N'-dimethyl-1,2-cyclohexanediamine)copper(II) bromide (12.8 mg, 0.025 mmol) and K$_3$PO$_4$ (330 mg, 1.55 mmol) and then evacuated and backfilled with argon, and toluene (1 mL), 3,5-dimethyliodobenzene (240 mg, 1.03 mmol), 2-pyrrolidinone (108 mg, 1.26 mmol), and dodecane (160 mg, 0.94 mmol, GC internal standard) were added through a rubber septum. The septum was removed: the flask was sealed with a Teflon screwcap, and the mixture was stirred at room temperature for 2 min and then heated to 80° C. with stirring until the starting aryl iodide had been completely consumed as judged by GC analysis. The mixture was cooled to room temperature, diluted with ethyl acetate, and filtered through Celite to give 96% GC yield of the title compound.

EXAMPLE 28

Preparation of Phenyl 3,5-Dimethylphenyl Sulfide Using Copper(I) Oxide

Copper(I) oxide (7.2 mg, 0.05 mmol) and potassium carbonate (276 mg, 2.0 mmol) were added to a screw-capped test tube with a Teflon-lined septum. The tube was evacuated and backfilled with argon (3 cycles). 2-Propanol (1.0 mL, bench top grade solvent without degassing and pre-drying), ethylene glycol (111 µL, 2.0 mmol, bench top grade solvent) and 5-iodo-m-xylene (144 µL, 1.0 mmol) and thiophenol (103 µL, 1.0 mmol) were added by syringes at room temperature. The tube was heated to 80° C. and stirred for 20 hours. The reaction mixture was then allowed to reach room temperature. Ethyl acetate (approx. 5 mL) and dodecane (227 µL, GC standard) were added. The aliquot was analyzed by GC to give 93% conversion of ArI and 93% GC yield of phenyl 3,5-dimethylphenyl sulfide.

EXAMPLE 29

3,5-Dimethyl-benzonitrile

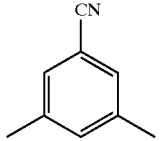

An oven dried screw cap test tube was charged with NaCN (140 mg, 2.857 mmol) dried KI (79 mg, 0.476 mmol, 20 mol %) and CuI (45 mg, 0.236 mmol, 10 mol %), evacuated and backfilled with argon three times. Anhydrous toluene (1550 µl), N,N'-dimethylethylenediamine (255 µl, 2.395 mmol), 1-Bromo-3,5-dimethyl-benzene (255 µl, 1.877 mmol), and benzyl alcohol (155 µl, 1.498 mmol) were added under argon. The tube was sealed and the reaction mixture was stirred magnetically at 110° C. for 12 h. The resulting yellow color suspension was cooled to room temperature, 2 mL of ethyl acetate, 250 μl of n-dodecane as internal standard, 1 mL of ammonium hydroxide 30% and 1 mL of water were added. The mixture was stirred at 25° C. for 10 min then the organic layer was washed with 1 mL of water and dried over MgSO$_4$. The GC analysis showed a conversion of 91% with a yield of the title product, calculated vs internal standard, of 88%.

EXAMPLE 30

1H-Indole-5-carbonitrile

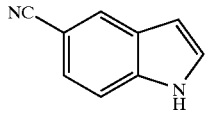

An oven dried screw cap test tube was charged with NaCN (98 mg, 2.00 mmol) dried KI (55 mg, 0.331 mmol, 20 mol %) and CuI (32 mg, 0.168 mmol, 10 mol %), 5-Bromoindole (327 mg, 1.667 mmol), evacuated and backfilled with argon three times. Anhydrous toluene (1.1 mL) and N,N'-dimethylethylenediamine (180 μL, 1.691 mmol) were added under argon. The tube was sealed and the reaction mixture was stirred magnetically at 110° C. for 24 h. The resulting yellow color suspension was cooled to room temperature, 2 mL of ethyl acetate, 1 mL of ammonium hydroxide 30% and 1 mL of water were added. The mixture was stirred at 25° C. for 10 min then the organic layer was separated and the aqueous layer was extracted three times with ethyl acetate (3×2 mL). The organic layers combined were washed with 5 mL of water and dried over MgSO$_4$. The GC analysis showed complete conversion of starting material with a desired product area of 99%. The solvent was removed at reduced pressure. Purification of the residue by flash chromatography on silica gel (2×15 cm; hexane/ethyl acetate 10:1) provided 225 mg (95% yield) of the title compound as a white solid.

EXAMPLE 31

N-(4-Cyano-2-fluoro-phenyl)-acetamide

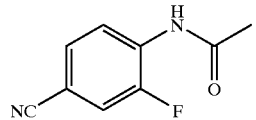

An oven dried screw cap test tube was charged with NaCN (137 mg, 2.796 mmol) dried KI (77 mg, 0.464 mmol, 20 mol %) and CuI (44 mg, 0.231 mmol, 10 mol %), N-(4-Bromo-2-fluoro-phenyl)-acetamide (540 mg, 2.330 mmol), evacuated and backfilled with argon three times. Anhydrous toluene (1.550 mL) and N,N'-dimethylethylenediamine (250 μl, 2.348 mmol) were added under argon. The tube was sealed and the reaction mixture was stirred magnetically at 110° C. for 24 h. The resulting yellow color suspension was cooled to room temperature, 2 mL of ethyl acetate, 1 mL of ammonium hydroxide 30% and 1 mL of water were added. The mixture was stirred at 25° C. for 10 min then the organic layer was separated and the aqueous layer was extracted three times with ethyl acetate (3×2 mL). The organic layers combined were washed with 5 mL of water and dried over MgSO$_4$. The solvent was removed at reduced pressure. Purification of the residue by flash chromatography on silica gel (2×15 cm; hexane/ethyl acetate 10:1) provided 372 mg (90% yield) of the title compound as a pale yellow solid.

EXAMPLE 32

4-Iodobiphenyl

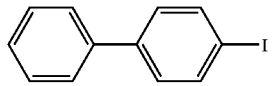

Using Ethylenediamine as Ligand

A Schlenk tube was charged with CuI (19.5 mg, 0.102 mmol, 10 mol %), 4-bromobiphenyl (234 mg, 1.00 mmol), NaI (300 mg, 2.00 mmol), evacuated and backfilled with argon. Ethylenediamine (13.5 μL, 0.202 mmol, 20 mol %) and sulfolane (1.0 mL) were added under argon. The Schlenk tube was sealed with a Teflon valve and the reaction mixture was stirred at 130° C. for 23 h. The resulting suspension was allowed to reach room temperature, poured into hexane (20 mL) and washed with water (3×20 mL). The combined organic phases were dried (MgSO$_4$), concentrated, and the residue was purified by flash chromatography on silica gel (hexane) to provide 262 mg (94% yield) of 4-iodobiphenyl as white crystals.

Using 1,2-cyclohexanediamine as Ligand

The procedure above was followed except that 1,2-cyclohexanediamine (a mixture of the cis- and racemic trans-diastereomers, 24.5 μL, 0.200 mmol, 20 mol %) was used instead of ethylenediamine. The resulting suspension was allowed to reach room temperature. Ethyl acetate (2 mL), water (2 mL), and dodecane (internal GC standard, 230 μL) were added to the reaction mixture. A 50 μL sample of the supernatant solution was diluted with ethyl acetate (1 mL) and analyzed by GC to provide 91% yield of 4-iodobiphenyl.

EXAMPLE 33

1-Iodo-2-methylpropene

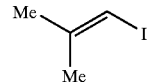

A 50 mL Schlenk tube was charged with CuI (385 mg, 2.02 mmol, 5.0 mol %), NaI (9.00 g, 60.0 mmol), evacuated and backfilled with argon. N,N'-Dimethylethylenediamine (426 μL, 4.00 mmol, 10 mol %), sulfolane (20 mL), and 1-bromo-2-methylpropene (4.10 mL, 40.0 mmol) were added under argon. The Schlenk tube was sealed with a Teflon valve and the reaction mixture was stirred at 90° C. for 24 h. The resulting dark green suspension was allowed to reach room temperature, poured into pentane (100 mL) and washed with a solution of 30% aq ammonia (10 mL) in water (100 mL), followed by water (3×10 mL). The combined organic phases were dried (MgSO$_4$) and concentrated to ~10 mL volume. The residue was distilled collecting the fraction boiling at 120–124° C. to give 4.82 g (66% yield) of 1-iodo-2-methylpropene as a colorless liquid.

EXAMPLE 34

1-Iodo-1-(trimethylsilyl)ethylene

A Schlenk tube was charged with CuI (9.6 mg, 0.0504 mmol, 5.0 mol %), NaI (300 mg, 2.00 mmol), evacuated and backfilled with argon. trans-N,N'-Dimethyl-1,2-cyclohexanediamine (16 μL, 0.10 mmol, 10 mol %), 1-bromo-1-(trimethylsilyl)ethylene (155 μL, 1.00 mmol), and THF (1.0 mL) were added under argon. The Schlenk tube was sealed with a Teflon valve and the reaction mixture was stirred at 70° C. for 15 h. The resulting suspension was allowed to reach room temperature. Dichloromethane (2 mL) and dodecane (internal GC standard, 230 μL) were added to the reaction mixture. A 50 μL sample of the supernatant solution was diluted with ethyl acetate (1 mL) and analyzed by GC to provide 95% conversion of 1-bromo-1-(trimethylsilyl)ethylene and clean formation of 1-iodo-1-(trimethylsilyl)ethylene.

EXAMPLE 35

Preparation of 4-Methylbenzonitrile from an Aryl Chloride

A Schlenk tube was charged with CuCN (108 mg, 1.21 mmol), NaI (150 mg, 1.00 mmol), evacuated and backfilled with argon. trans-N,N'-Dimethyl-1,2-cyclohexanediamine (190 μL, 1.21 mmol) and 4-chlorobenzene (0.95 mL, 8.01 mmol) were added under argon. The Schlenk tube was sealed with a Teflon valve and the reaction mixture was stirred at 130° C. for 20 h. The resulting black suspension was allowed to reach room temperature. Ethyl acetate (3 mL) and dodecane (internal GC standard, 230 μL) were added to the reaction mixture. A 50 μL sample of the supernatant solution was diluted with ethyl acetate (1 mL) and analyzed by GC to provide 60% yield of 4-methylbenzonitrile.

EXAMPLE 36

Figure 9:
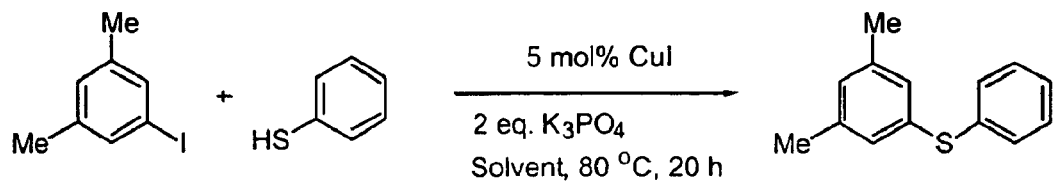
FIG. 9 tabulates examples of the copper-catalyzed arylation of thiophenol with 3,5-dimethylphenyl iodide using various solvents.
Figure 10:
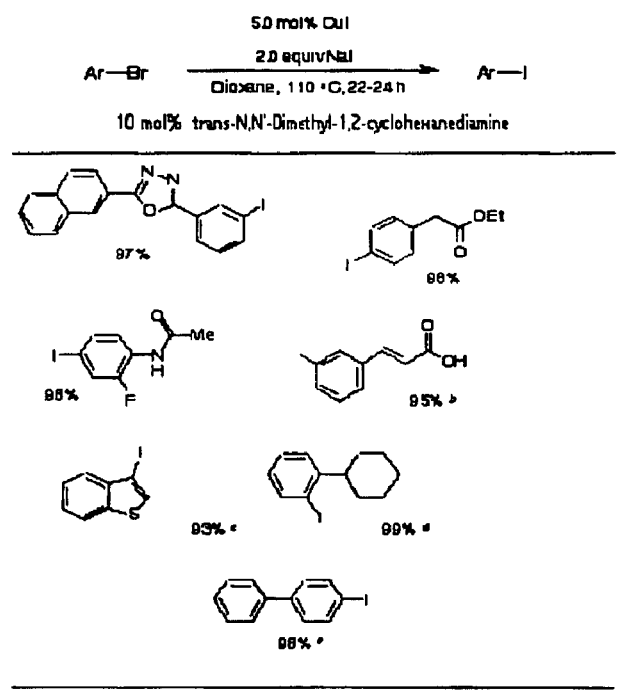
FIG. 10 depicts copper-catalyzed conversion of aryl bromides into aryl iodides.

Preparation of Phenyl 3,5-Dimethylphenyl Sulfide Using Various Solvents (See FIG. 9)

CuI (0.05 mmol) and potassium carbonate (276 mg, 2.0 mmol) were added to a screw-capped test tube with a Teflon-lined septum. The tube was evacuated and backfilled with argon (3 cycles). Solvent (1.0 mL), ethylene glycol (111 μL, 2.0 mmol; for entries 2, 4, 6, 8, 10), 5-iodo-m-xylene (144 μL, 1.0 mmol) and thiophenol (103 μL, 1.0 mmol) were added by syringes at room temperature. The tube was heated to 80° C. and stirred for 20 hours. The reaction mixture was then allowed to reach room temperature. Ethyl acetate (approx. 5 mL) and dodecane (227 μL, GC standard) were added. The aliquot was analyzed by GC or GC-MS. See FIG. 9.

EXAMPLE 37

Benzonitrile from iodobenzene and Copper cyanide Using N,N'-dimethylethylenediamine as Ligand A Schlenk tube was charged with CuCN (108 mg, 1.21 mmol), evacuated, backfilled with Ar. N,N'-Dimethylethylenediamine (21.5 μL, 0.202 mmol, 20 mol %), iodobenzene (112 μL, 1.00 mmol), and toluene (1.0 mL) were added under Ar. The Schlenk tube was sealed with a Teflon valve and the reaction mixture was stirred at 110° C. for 17 h. Dodecane (internal GC standard, 230 μL) and ethyl acetate (2 mL) were added. A 0.1 mL sample of the supernatant solution was diluted with ethyl acetate (1 mL) and analyzed by GC to provide a 31% yield of benzonitrile.

EXAMPLE 38

3,5-Dimethylbenzonitrile from 5-bromo-m-xylene and potassium cyanide using N,N'-dimethylethylenediamine as ligand A Schlenk tube was charged with CuI (19.5 mg, 0.102 mmol, 20 mol %), KCN (78 mg, 1.20 mmol), evacuated, backfilled with Ar. N,N'-Dimethylethylenediamine (21.5 μL, 0.202 mmol, 20 mol %), 5-bromo-m-xylene (136 μL, 1.00 mmol), and toluene (1.0 mL) were added under Ar. The Schlenk tube was sealed with a Teflon valve and the reaction mixture was stirred at 110° C. for 24 h. Dodecane (internal GC standard, 230 μL), ethyl acetate (2 mL), and 30% aq ammonia (1 mL) were added. A 0.1 mL sample of the supernatant solution was diluted with ethyl acetate (1 mL) and analyzed by GC to provide a 15% yield of 3,5-dimethylbenzonitrile.

EXAMPLE 39

General procedure for copper-catalyzed carbon-sulfur bond formation

Copper(I) iodide was purchased from Strem Chemical. Potassium carbonate, 2-propanol, ethylene glycol and hexane were purchased from Mallinckrodt. It should be noted that 2-propanol (bench grade, 4 L bottle) and ethylene glycol (bench grade, 4 L bottle) were used directly without pre-drying or degassing. All thiols and aryl halides were used as received. Silica gel (230–400 mesh) and ethyl acetate were purchased from Merck. Elemental analysis were performed by Atlantic Microlabs, Inc., Norcross, Ga. 30091. $^1$H NMR and $^{13}$C NMR were recorded on a Varian 300 MHz instrument with chemical shifts reported relative to residual deuterated solvent peaks. Gas chromatographic analysis were performed on a Hewlett Packard 6890 instrument with FID detector and a Hewlett Packard 10 m×0.2 mm i.d. HP-1 capillary column. Mass spectra (GC-MS) were recorded on a Hewlett Packard model GCD. All yield reported in the publication represent an average of at least two independent runs. Characterization data for previously unknown compounds were determined from a single run with isolated yields. Compounds described in the literature were characterized by comparing their $^1$H, $^{13}$C NMR and GC-MS to the previously reported data.

Cu(I) iodide (10 mg, 0.05 mmol), potassium carbonate (276 mg, 2.0 mmol) and aryl iodide (1.0 mmol, if solid) were charged into a screw-capped test tube with Teflon-lined septum. The tube was evacuated and backfilled with argon (3 cycles). 2-Propanol (1.0 μL, bench grade solvent without degassing and pre-drying), ethylene glycol (111 μL, 2.0 mmol, bench grade solvent), aryl iodide (1.0 mmol, if liquid) and thiols (1.0 mmol) were added by syringes at room temperature. The tube was heated to 80° C. and stirred for 20–24 hours. The reaction mixture was then allowed to reach room temperature. Ethyl acetate (approx. 5 mL) and dodecane (227 μL, GC standard) were added. The aliquot was analyzed GC. The reaction mixture was then filtered and concentrated. The crude product was purified by flash column chromatography on silica gel to afford the desired thioether.

EXAMPLE 40

3,5-Dimethylphenyl phenyl sulfide

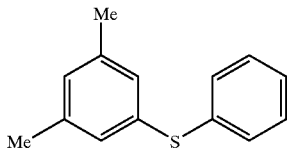

The general procedure in example 39 was followed. 5-Iodo-m-xylene (144 µL, 1.0 mmol), thiophenol (103 µL, 1.0 mmol), CuI (10 mg, 0.05 mmol), K$_2$CO$_3$ (276 mg, 2.0 mmol), ethylene glycol (111 µL, 2.0 mmol) and 2-propanol (1.0 mL) were used to obtain the 3,5-dimethylphenyl phenyl sulfide (196 mg, 92% yield) as colorless liquid. Column chromatography solvent (hexane). R$_f$=0.5 (hexane). $^1$H NMR (CDCl$_3$, 300 MHz) δ 7.19–7.29 (m, 5 H), 6.97 (s, 2 H), 6.87 (s, 1 H). MS (EI) m/z (relative intensity) 214 (100), 137 (30).

EXAMPLE 41

3-Cyanophenyl phenyl sulfide

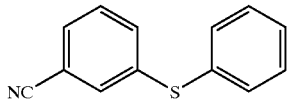

The general procedure in example 39 was followed. 3-Iodobenzonitrile (229 mg, 1.0 mmol), thiophenol (103 µL, 1.0 mmol), CuI (10 mg, 0.05 mmol), K$_2$CO$_3$ (276 mg, 2.0 mmol), ethylene glycol (111 µL, 2.0 mmol) and 2-propanol (1.0 mL) were used to obtain the 3-cyanophenyl phenyl sulfide (181 mg, 86% yield) as colorless liquid. Column chromatography solvent (hexane/ethyl acetate=25/1). R$_f$=0.4 (hexane/ethyl acetate=20/1). $^1$H NMR (CDCl$_3$, 300 MHz) δ 7.30–7.45 (m, 9 H). $^{13}$C NMR (CDCl$_3$, 75 MHz) δ 140.2, 133.6, 132.9, 132.3, 131.7, 130.0, 129.7, 129.6, 129.1, 118.5, 113.5. MS (EI) m/z (relative intensity) 211 (30), 185 (20), 134 (100).

EXAMPLE 42

3-Bromophenyl phenyl sulfide

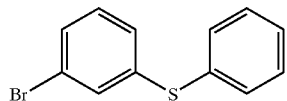

The general procedure in example 39 was followed. 3-bromoiodobenzene (283 mg, 1.0 mmol), thiophenol (103 µL, 1.0 mmol), CuI (10 mg, 0.05 mmol), K$_2$CO$_3$ (276 mg, 2.0 mmol), ethylene glycol (111 µL, 2.0 mmol) and 2-propanol (1.0 µL) were used to obtain the 3-bromophenyl phenyl sulfide (240 mg, 91% yield) as colorless liquid. Column chromatography solvent (hexane). R$_f$=0.6 (hexane). $^1$H NMR (CDCl$_3$, 300 MHz) δ 7.11–7.22 (m, 2 H), 7.28–7.40 (m, 7 H). $^{13}$C NMR (CDCl$_3$, 75 MHz) δ 139.2, 134.1, 132.5, 132.4, 130.6, 129.8, 129.7, 128.6, 128.2, 123.2. MS (EI) m/z (relative intensity) 266 (40), 264 (40).

EXAMPLE 43

3-Nitrophenyl 3-tolyl sulfide

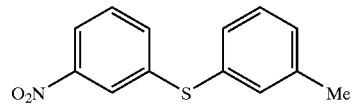

The general procedure in example 39 was followed. 3-Nitroiodobenzene (249 mg, 1.0 mmol), m-thiocresol (119 µL, 1.0 mmol), CuI (10 mg, 0.05 mmol), K$_2$CO$_3$ (276 mg, 2.0 mmol), ethylene glycol (111 µL, 2.0 mmol) and 2-propanol (1.0 mL) were used to obtain the 3-nitrophenyl 3-tolyl sulfide (208 mg, 85% yield) as yellow liquid. Column chromatographic solvent (hexane/ethyl acetate=20/1). R$_f$=0.4 (hexane/ethyl acetate=20/1). $^1$H NMR (CDCl$_3$, 300 MHz) δ 7.95–7.99 (m, 2 H), 7.46 (dt, 1 H, J=7.5 Hz, 0.9 Hz), 7.38 (t, 1 H, J=8.1 Hz), 7.12–7.28 (m, 5 H), 2.36 (s, 3 H). $^{13}$C NMR (CDCl$_3$, 75 MHz) δ 141.0, 140.0, 134.3, 134.2, 131.7, 130.8, 130.0, 129.9, 129.8, 123.1, 122.9, 120.9. MS (EI) m/z (relative intensity) 245 (100), 184 (80).

EXAMPLE 44

4-(3-Tolyl)sulfanylaniline

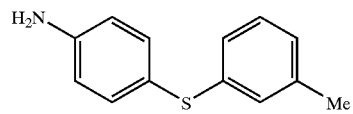

The general procedure in example 39 was followed. 4-Iodoaniline (219 mg, 1.0 mmol), m-thiocresol (119 µL, 1.0 mmol), CuI (10 mg, 0.05 mmol), K$_2$CO$_3$ (276 mg, 2.0 mmol), ethylene glycol (111 µL, 2.0 mmol) and 2-propanol (1.0 mL) were used to obtain the 4-(3-tolyl)sulfanylaniline (194 mg, 90% yield) as pale yellow liquid. Column chromatographic solvent (hexane/ethyl acetate=4/1). R$_f$=0.4 (hexane/ethyl acetate=4/1). $^1$H NMR (CDCl$_3$, 300 MHz) δ 7.28 (dt, 2 H, J=7.5 Hz, 0.9 Hz), 7.08 (t, 1 H, J=7.8 Hz), 6.91 (t, 3 H, J=7.5 Hz), 3.71 (brs, 2 H), 2.26 (s, 3 H). $^{13}$C NMR (CDCl$_3$, 75 MHz) δ 138.8, 138.1, 136.2, 128.9, 128.1, 126.4, 124.6, 117.5, 116.1, 100.0, 21.8. IR (neat, cm$^{-1}$) 3460 (broad), 3377 (broad), 3211, 3051, 3027, 2919. MS (EI) m/z (relative intensity) 219 (100), 92 (80). HRMS (EI), Cald. for C$_{13}$H$_{13}$NS 215.0769. Found 215.0766.

EXAMPLE 45

3-Methoxyphenyl 4-chlorophenyl sulfide

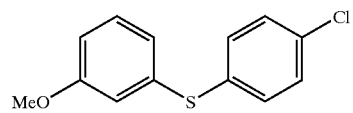

The general procedure in example 39 was followed. 3-Iodoanisole (234 mg, 1.0 mmol), 4-chlorothiophenol (145 mg, 1.0 mmol), CuI (10 mg, 0.05 mmol), K$_2$CO$_3$ (276 mg, 2.0 mmol), ethylene glycol (111 µL, 2.0 mmol) and 2-propanol (1.0 mL) were used to obtain the 3-methoxyphenyl 4-chlorophenyl sulfide (203 mg, 81% yield) as colorless liquid. Column chromatographic solvent (hexane/ethyl acetate=50/1). $R_f$=0.4 (hexane/ethyl acetate=40/1). $^1$H NMR (CDCl$_3$, 300 MHz) δ 7.13–7.26 (m, 2 H), 6.88 (ddd, 2 H, J=1.2 Hz, 1.8 Hz, 7.8 Hz), 6.83 (t, 2 H, J=1.5 Hz), 6.78 (ddd, 2 H, J=0.9 Hz, 2.7 Hz, 8.1 Hz), 3.75 (s, 3 H). $^{13}$C NMR (CDCl$_3$, 75 MHz) δ 160.2, 136.6, 134.3, 133.4, 132.5, 130.3, 129.5, 123.4, 116.4, 113.3, 55.7. IR (neat, cm$^{-1}$) 3065, 3002, 2962, 2949, 2820. MS (E) m/z (relative intensity) 252 (30), 250 (100). Anal Cald for C$_{13}$H$_{11}$ClOS, Cald. C, 62.27; H, 4.42. Found C, 62.58; H, 4.46.

EXAMPLE 46

4-(3-Methoxyphenyl)sulfanylacetophenone

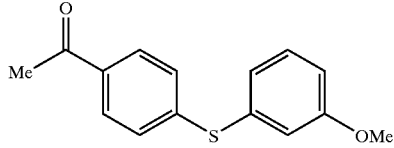

The general procedure in example 39 was followed. 3-Iodoacetophenone (246 mg, 1.0 mmol), 3-methoxythiophenol (124 µL, 1.0 mmol), CuI (10 mg, 0.05 mmol), K$_2$CO$_3$ (276 mg, 2.0 mmol), ethylene glycol (111 µL, 2.0 mmol) and 2-propanol (1.0 mL) were used to obtain the 4-(3-methoxyphenyl)sulfanylacetophenone (209 mg, 81% yield) as pale yellow liquid. Column chromatographic solvent (hexane/ethyl acetate=10/1). $R_f$=0.3 (hexane/ethyl acetate=10/1). $^1$H NMR (CDCl$_3$, 300 MHz) δ 7.80 (dd, 2 H, J=6.6 Hz, 2.1 Hz), 7.29 (t, 1 H, J=7.8 Hz), 7.20–7.24 (m, 2 H), 7.03–7.07 (m, 1 H), 7.00 (m, 1 H), 6.90 (ddd, 1 H, J=8.4 Hz, 2.7 Hz, 1.2 Hz), 3.79 (s, 3 H), 2.55 (s, 3 H). $^{13}$C NMR (CDCl$_3$, 75 MHz) δ 196.2, 160.4, 144.7, 134.7, 133.4, 130.6, 129.1, 127.8, 126.0, 118.6, 114.9, 55.7, 26.9. IR (neat, cm$^{-1}$) 3064, 3002, 2962, 2939, 2836, 1698. MS (EI) m/z (relative intensity) 258 (80), 243 (100). Anal Cald for C$_{14}$H$_{15}$O$_2$S, Cald. C, 69.74; H, 5.46. Found C, 69.47; H, 5.39.

EXAMPLE 47

4-(3,5-Dimethylphenyl)sulfanylphenol

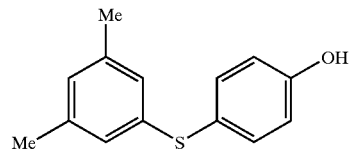

The general procedure in example 39 was followed. 5-Iodo-m-xylene (144 µL, 1.0 mmol), 4-mercaptophenol (126 mg, 1.0 mmol), CuI (10 mg, 0.05 mmol), K$_2$CO$_3$ (276 mg, 2.0 mmol), ethylene glycol (111 µL, 2.0 mmol) and 2-propanol (1.0 mL) were used to obtain the 4-(3,5-dimethylphenyl)sulfanylphenol (207 mg, 90% yield) as colorless liquid. Workup procedure: ethyl acetate (approx. 5 mL) and dodecane (227 µL, GC standard) were added to the reaction mixture after the reaction was completed. The organic layer was neutralized by dilute HCl to pH 8. The aqueous layer was extracted by ethyl acetate (4×10 mL). The combined organic layers were concentrated and purified by column chromatography on silica gel using hexane/ethyl acetate=10/1 as the eluent to afford the titled product. $R_f$=0.3 (hexane/ethyl acetate=10/1). $^1$H NMR (CDCl$_3$, 300 MHz) δ 7.33 (dt, 2 H, J=1.8 Hz, 8.4 Hz), 6.77–6.81 (m, 5 H), 4.83 (s, 1 H), 2.22 (s, 6 H). $^{13}$C NMR (CDCl$_3$, 75 MHz) δ 155.6, 138.8, 137.7, 135.4, 128.1, 126.4, 125.3, 116.6, 21.6. IR (neat, cm$^{-1}$) 3371 (broad), 3031, 2917, 2860. MS (EI) m/z (relative intensity) 230 (100), 215 (20). Anal Cald for C$_{14}$H$_{14}$OS, Cald. C, 73.01; H, 6.13. Found C, 73.21; H, 6.11.

EXAMPLE 48

3-(4-tert-Butylphenyl)sulfanylphenol

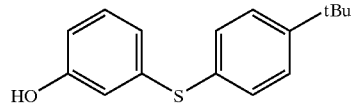

The general procedure in example 39 was followed. 3-Iodophenol (220 mg, 1.0 mmol), 4-tert-butylthiophenol (168 µL, 1.0 mmol), CuI (10 mg, 0.05 mmol), K$_2$CO$_3$ (276 mg, 2.0 mmol), ethylene glycol (111 µL, 2.0 mmol) and 2-propanol (1.0 mL) were used to obtain the 3-(4-tert-butylphenyl)sulfanylphenol (232 mg, 90% yield) as the colorless oil. Workup procedure: ethyl acetate (approx. 5 mL) and dodecane (227 µL, GC standard) were added to the reaction mixture after the reaction was completed. The organic layer was neutralized by dilute HCl to pH 8. The aqueous layer was extracted by ethyl acetate (4×10 mL). The combined organic layers were concentrated and purified by column chromatography on silica gel using hexane/ethyl acetate=10/1 as the eluent to afford the titled product. $R_f$=0.2 (hexane/ethyl acetate=10/1) (Note: same $R_f$ value as the starting material). $^1$H NMR (CDCl$_3$, 300 MHz) δ 7.21–7.34 (m, 2 H), 7.14 (t, 1 H, J=8.1 Hz), 6.95 (t, 1 H, J=8.1 Hz), 6.84–6.88 (m, 1 H), 6.78–6.81 (m, 1 H), 6.64–6.71 (m, 2 H). $^{13}$C NMR (CDCl$_3$, 75 MHz) δ 156.0, 132.5, 131.2, 130.3, 130.1, 124.8, 122.1, 116.3, 115.2, 113.8, 35.0, 31.7. IR (neat, cm$^{-1}$) 3375 (broad), 2962, 2904, 2867. MS (EI) m/z (relative intensity) 258 (100). HRMS (EI), Cald. for C$_{16}$H$_{18}$OS, 258.1073. Found 258.1068.

EXAMPLE 49

3-(4-Methoxyphenyl)sulfanylbenzoic acid

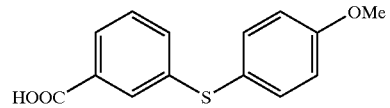

Cu(I) iodide (10 mg, 0.05 mmol), potassium carbonate (414 mg, 3.0 mmol) and 3-iodobenzoic acid (248 mg, 1.0 mmol) were charged into a screw-capped test tube with Teflon-lining. The tube was evacuated and backfilled with argon (3 cycles). 2-Propanol (1.0 mL, bench grade solvent without degassing and pre-drying), ethylene glycol (111 µL, 2.0 mmol, bench grade solvent) and 4-methoxythiophenol (123 µL, 1.0 mmol) were added by syringes at room temperature. The tube was heated to 80° C. and stirred for 24 hours. The reaction mixture was then allowed to reach room temperature. Ethyl acetate (~5 mL), water (~10 mL) and dil. HCl were added to reach pH 3–4. The reaction mixture was extracted with ethyl acetate (2×10 mL) and CH$_2$Cl$_2$ (2×10 mL). The combined organic phase was passed through a short pad of silica (0.5 cm diameter×1 cm height). Solvent was removed and the yellow residue was redissolved in minimum amount of $CH_2Cl_2$. Hexane was added slowly and the solution was stand overnight at room temperature. White crystal was obtained as the titled product (221 mg, 85% yield). $R_f$=0.2 (hexane/ethyl acetate=2/1) (Note: same $R_f$ value as the starting material). Melting point; 121–123° C. $^1$H NMR (CDCl$_3$, 300 MHz) δ 10.68 (brs, 1 H), 7.86 (s, 1 H), 7.82 (dt, 1 H, J=1.8 Hz, 6.6 Hz), 7.42 (dt, 2 H, J=2.1 Hz, 8.7 Hz), 7.28–7.31 (m, 2 H), 6.90 (dt, 2 H, J=2.1 Hz, 8.7 Hz), 3.83 (s, 3 H). $^{13}$C NMR (CDCl$_3$, 75 MHz) δ 172.0, 160.3, 140.3, 136.1, 132.8, 130.2, 129.2, 129.1, 127.4, 123.1, 55.7. IR (neat, cm$^{-1}$) 2964 (broad), 2943, 2902, 2875, 2856, 2840, 2813, 2360, 2342, 1688. MS (EI) m/z (relative intensity) 260 (100). Anal. Cald. for $C_{14}H_{12}O_3S$, Cald. C, 64.60; H, 4.65. Found C, 64.52; H, 4.68.

EXAMPLE 50

Methyl 3-(3-methoxyphenyl)sulfanylbenzoate

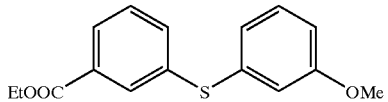

Cu(I) iodide (10 mg, 0.05 mmol), potassium carbonate (276 mg, 2.0 mmol) and Methyl 3-iodobenzoate (276 mg, 1.0 mmol) were charged into a screw-capped test tube with Teflon-lining. The tube was evacuated and backfilled with argon (3 cycles). Anhydrous DME (1.0 mL) and 3-methoxythiophenol (124 μL, 1.0 mmol) were added by syringes at room temperature. The tube was heated to 80° C. and stirred for 22 hours. The reaction mixture was then allowed to reach room temperature. Ethyl acetate (approx. 5 mL) and dodecane (227 μL, GC standard) were added. The aliquot was analyzed GC. The reaction mixture was then filtered and concentrated. The crude product was purified by column chromatography on silica gel using hexane/ethyl acetate=20/1 to afford colorless liquid as the titled product (220 mg, 81% yield). $R_f$=0.5 (hexane/ethyl acetate=10/1). $^1$H NMR (CDCl$_3$, 300 MHz) δ 8.02–8.03 (m, 1 H), 7.89 (dt, 1 H, J=1.2 Hz, 8.1 Hz), 7.45–7.49 (m, 1 H), 7.34 (t, 1 H, J=7.5 Hz), 7.21 (t, 1 H, J=8.1 Hz), 6.86–6.92 (m, 2 H), 6.79 (ddd, 1 H, J=0.6 Hz, 2.4 Hz, 8.1 Hz), 4.34 (q, 2 H, J=7.2 Hz), 3.76 (s, 3 H), 1.37 (t, 3 H, J=7.2 Hz). $^{13}$C NMR (CDCl$_3$, 75 MHz) δ 166.0, 160.2, 136.5, 136.3, 135.2, 132.0, 131.7, 130.3, 129.3, 128.4, 123.7, 116.6, 113.5, 61.5, 55.7, 14.7. IR (neat, cm$^{-1}$) 3064, 2981, 2960, 2937, 2360, 2342, 1717. MS (EI) m/z (relative intensity) 288 (100), 243 (30). Anal. Cald. for $C_{16}H_{16}O_3S$, Cald. C, 66.64; H, 5.59. Found C, 66.87; H, 5.66.

EXAMPLE 51

3-(3-Methoxyphenyl)sulfanylbenzaldehyde

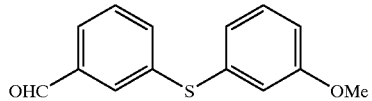

The general procedure in example 39 was followed. 3-Iodobenzaldehyde (232 mg, 1.0 mmol), 3-methoxythiophenol (124 μL, 1.0 mmol), CuI (10 mg, 0.05 mmol), $K_2CO_3$ (276 mg, 2.0 mmol), ethylene glycol (111 μL, 2.0 mmol) and 2-propanol (1.0 mL) were used to obtain the 3-(3-methoxyphenyl)sulfanylbenzaldehyde (205 mg, 85% yield) as colorless liquid. Column chromatographic solvent (hexane/ethyl acetate=15/1). $R_f$=0.4 (hexane/ethyl acetate=10/1). $^1$H NMR (CDCl$_3$, 300 MHz) δ 9.91 (s, 1 H), 7.76–7.77 (m, 1 H), 7.71 (dt, 1 H, J=1.2 Hz, 7.2 Hz), 7.45–7.53 (m, 1 H), 7.42 (t, 1 H, J=7.5 Hz), 7.25 (t, 1 H, J=7.5 Hz), 6.91–6.98 (m, 2 H), 6.84 (ddd, 1 H, J=1.2 Hz, 2.4 Hz, 8.1 Hz), 3.77 (s, 3 H). $^{13}$C NMR (CDCl$_3$, 75 MHz) δ 191.7, 160.3, 138.4, 137.3, 135.8, 135.0, 131.1, 130.5, 129.9, 127.9, 124.6, 117.6, 114.0, 55.7. IR (neat, cm$^{-1}$) 3060, 3006, 2960, 2937, 2834, 2726, 1698. MS (EI) m/z (relative intensity) 244 (100), 227 (30), 211 (40). Anal. Cald. for $C_{14}H_{12}O_2S$, Cald. C, 68.83; H, 4.95. Found C, 69.04; H, 4.94.

EXAMPLE 52

3-(4-Methoxyphenyl)sulfanylbenzylamine

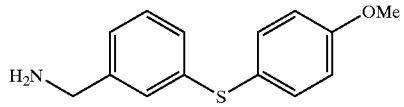

The general procedure in example 39 was followed. 3-Iodobenzylamine (133 μL, 1.0 mmol), 4-methoxythiophenol (123 μL, 1.0 mmol), CuI (10 mg, 0.05 mmol), $K_2CO_3$ (276 mg, 2.0 mmol), ethylene glycol (111 μL, 2.0 mmol) and 2-propanol (1.0 mL) were used to obtain the 3-(4-methoxyphenyl)sulfanylbenzylamine (218 mg, 89% yield) as light yellow liquid. Column chromatographic solvent ($CH_2Cl_2$ (saturated with $NH_3$)/MeOH=30/1). $R_f$=0.4 ($CH_2Cl_2$ (saturated with $NH_3$)/MeOH=30/1), (Note: same $R_f$ value as the starting material). $^1$H NMR (CDCl$_3$, 300 MHz) δ 7.40 (dt, 2 H, J=1.8 Hz, 8.7 Hz), 7.19 (t, 1 H, J=7.8 Hz), 7.06–7.13 (m, 2 H), 7.01 (dt, 1 H, J=1.5 Hz, 7.5 Hz), 6.89 (dt, 2 H, J=2.1 Hz, 8.7 Hz), 3.82 (s, 3 H), 3.79 (s, 2 H), 1.40 (brs, 2 H). $^{13}$C NMR (CDCl$_3$, 75 MHz) δ 159.9, 144.3, 139.0, 135.6, 129.3, 126.9, 126.7, 124.8, 124.3, 115.2, 55.7, 46.6. IR (neat, cm$^{-1}$) 3373 (broad), 3072, 3060, 2939, 2836. MS (EI) m/z (relative intensity) 245 (100), 106 (60). HRMS (EI), Cald. for $C_{14}H_{15}NOS$ 245.0869. Found 245.0862.

EXAMPLE 53

2-(4-Methoxyphenyl)sulfanylbenzylalcohol

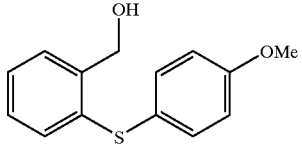

The general procedure in example 39 was followed. 2-Iodobenzylalcohol (234 mg, 1.0 mmol), 4-methoxythiophenol (123 μL, 1.0 mmol), CuI (10 mg, 0.05 mmol), $K_2CO_3$ (276 mg, 2.0 mmol), ethylene glycol (111 μL, 2.0 mmol) and 2-propanol (1.0 mL) were used to obtain the 2-(4-methoxyphenyl)sulfanylbenzylalcohol (219 mg, 89% yield) as colorless liquid. Column chromatographic solvent (hexane/ethyl acetate=5/1). $R_f$=0.3 (hexane/ethyl acetate=5/1). $^1$H NMR (CDCl$_3$, 300 MHz) δ 7.40 (dd, 1 H, J=6.6 Hz, 1.5 Hz), 7.29 (dt, 2 H, J=8.7 Hz, 2.1 Hz), 7.13–7.21 (m, 2 H), 7.08 (dd, 1 H, J=8.1 Hz, 2.1 Hz), 6.86

(dt, 2 H, J=9.0 Hz, 2.1 Hz), 4.78 (d, 2 H, J=6.3 Hz), 3.80 (s, 3 H), 2.12 (t, 1 H, J=6.3 Hz). $^{13}$C NMR (CDCl$_3$, 75 MHz) δ 159.7, 140.0, 135.9, 134.3, 130.8, 128.6, 128.5, 127.1, 124.5, 115.3, 63.9, 55.7. IR (neat, cm$^{-1}$) 3365 (broad), 3015, 2962, 2904, 2867. MS (EI) m/z (relative intensity) 246 (100), 138 (40), 108 (70). HRMS (EI), Cald. for C$_{14}$H$_{14}$O$_2$S 246.0709. Found 246.0707.

EXAMPLE 54

2-(4-tert-Butylphenyl)sulfanylaniline

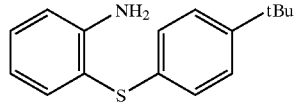

The general procedure in example 39 was followed. 2-Iodoaniline (219 mg, 1.0 mmol), 4-tert-butylthiophenol (166 mg, 1.0 mmol), CuI (10 mg, 0.05 mmol), K$_2$CO$_3$ (276 mg, 2.0 mmol), ethylene glycol (111 μL, 2.0 mmol) and 2-propanol (1.0 mL) were used to obtain the 2-(4-tert-butylphenyl)sulfanylaniline (231 mg, 90% yield) as light yellow liquid. Column chromatographic solvent (hexane/ethyl acetate=20/1). R$_f$=0.4 (hexane/ethyl acetate=10/1). $^1$H NMR (CDCl$_3$, 300 MHz) δ 7.42 (dd, 1 H, J=1.5 Hz, 7.5 Hz), 7.17–7.24 (m, 4 H), 7.00 (dt, 2 H, J=1.8 Hz, 8.4 Hz), 6.70–6.78 (m, 2 H), 4.28 (brs, 2 H), 1.26 (s, 9 H). $^{13}$C NMR (CDCl$_3$, 75 MHz) δ 148.8, 148.7, 137.5, 133.3, 131.1, 126.5, 126.3, 118.9, 115.5, 115.0, 34.8, 31.7. IR (neat, cm$^{-1}$) 3471, 3375, 3072, 3062, 3020, 2962, 2902, 2867. MS (EI) m/z (relative intensity) 257 (70), 242 (100). Anal. Cald. for C$_{16}$H$_{19}$NS, Cald. C, 74.66; H, 7.44. Found C, 74.64; H, 7.30.

EXAMPLE 55

3,5-Dimethylphenyl 2-chlorophenyl sulfide

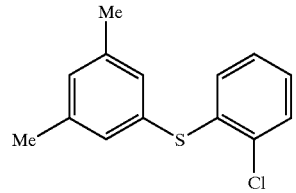

The general procedure in example 39 was followed. 5-Iodo-m-xylene (144 μL, 1.0 mmol), 2-chlorothiophenol (145 mg, 1.0 mmol), CuI (10 mg, 0.05 mmol), K$_2$CO$_3$ (276 mg, 2.0 mmol), ethylene glycol (111 μL, 2.0 mmol) and 2-propanol (1.0 mL) were used to obtain the 3,5-dimethylphenyl 2-chlorophenyl sulfide (215 mg, 87% yield) as colorless liquid. Column chromatographic solvent (hexane). R$_f$=0.5 (hexane/ethyl acetate=50/1). $^1$H NMR (CDCl$_3$, 300 MHz) δ 7.32–7.36 (m, 1 H), 7.05–7.10 (m, 4 H), 6.97 (s, 1 H), 6.88–6.92 (m, 1 H), 2.30 (s, 6 H). $^{13}$C NMR (CDCl$_3$, 75 MHz) δ 139.5, 137.4, 132.7, 131.7, 131.5, 130.6, 129.8, 129.6, 127.3, 126.9, 21.6. IR (neat, cm$^{-1}$) 3060, 3037, 2950, 2917, 2860. MS (EI) m/z (relative intensity) 250 (30), 248 (100).

EXAMPLE 56

Methyl 2-(3,5-dimethylphenyl)sulfanylbenzoate

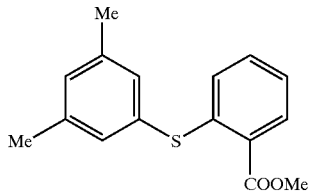

The general procedure in example 39 was followed. 5-Iodo-m-xylene (144 μL, 1.0 mmol), Methyl thiosalicylate (138 μL, 1.0 mmol), CuI (10 mg, 0.05 mmol), K$_2$CO$_3$ (276 mg, 2.0 mmol), and DME (1.0 mL) were used to obtain the methyl 2-(3,5-dimethylphenyl)sulfanylbenzoate (236 mg, 86% yield) as colorless liquid. Column chromatographic solvent (hexane/ethyl acetate 20/1). R$_f$=0.5 (hexane/ethyl acetate=10/1). $^1$H NMR (CDCl$_3$, 300 MHz) δ 7.95 (dd, 1 H, J=1.8 Hz, 8.1 Hz), 7.19–7.25 (m, 1 H), 7.17 (s, 2 H), 7.08 (dt, 1 H, J=1.2 Hz, 7.8 Hz), 7.03 (s, 1 H), 6.81 (dd, 1 H, J=0.9 Hz, 8.1 Hz), 3.94 (s, 3 H), 2.32 (s, 6 H). $^{13}$C NMR (CDCl$_3$, 75 MHz) δ 170.0, 144.0, 139.6, 133.4, 132.5, 131.2, 127.4, 126.5, 124.2, 117.1, 52.5, 21.6. IR (neat, cm$^{-1}$) 2950, 2916, 1712, 1711. MS (EI) m/z (relative intensity) 272 (100), 197 (70). HRMS (EI), Cald. for C$_{16}$H$_{16}$O$_2$S 272.0866. Found 272.0858.

EXAMPLE 57

3-(2-Isopropylphenyl)sulfanylanisole

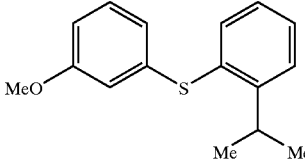

The general procedure in example 39 was followed. 3-Iodoanisole (234 mg, 1.0 mmol), 2-Isopropylbenzenethiol (90% purity, 168 μL, 1.0 mmol), CuI (10 mg, 0.05 mmol), K$_2$CO$_3$ (276 mg, 2.0 mmol), ethylene glycol (111 μL, 2.0 mmol) and 2-propanol (1.0 mL) were used to obtain the 3-(2-isopropylphenyl)sulfanylanisole (241 mg, 93% yield) as colorless liquid. Column chromatographic solvent (hexane/ethyl acetate=40/1). R$_f$=0.3 (hexane/ethyl acetate=40/1). $^1$H NMR (CDCl$_3$, 300 MHz) δ 7.29–7.36 (m, 3 H), 7.09–7.17 (m, 2 H), 6.67–6.73 (m, 3 H), 3.72 (s, 3 H), 3.54 (hept, 1 H, J=6.9 Hz), 1.22 (s, 3 H), 1.19 (s, 3 H). $^{13}$C NMR (CDCl$_3$, 75 MHz) δ 160.1, 150.9, 139.0, 134.5, 132.1, 129.9, 128.9, 126.8, 126.3, 121.4, 114.4, 111.9, 55.6, 31.1, 24.0. IR (neat, cm$^{-1}$) 3060, 2962, 2867, 2834, 2362, 2343. MS (EI) m/z (relative intensity) 258 (100), 241 (30), 225 (30). HRMS (EI), Cald. for C$_{16}$H$_{18}$OS 258.1078. Found 258.1080.

EXAMPLE 58

2-Tolyl 2-Isopropylphenyl sulfide

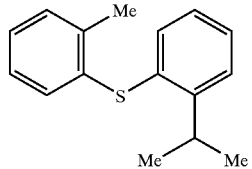

The general procedure in example 39 was followed. 2-Iodotoluene (218 mg, 1.0 mmol), 2-Isopropylbenzenethiol (90% purity, 168 μL, 1.0 mmol), CuI (10 mg, 0.05 mmol), $K_2CO_3$ (276 mg, 2.0 mmol), ethylene glycol (111 μL, 2.0 mmol) and 2-propanol (1.0 mL) were used to obtain the 2-tolyl 2-Isopropylphenyl sulfide (213 mg, 88% yield) as colorless liquid. Column chromatographic solvent (hexane). $R_f$=0.4 (hexane). $^1$H NMR (CDCl$_3$, 300 MHz) δ 7.32 (d, 1 H, J=7.5 Hz), 7.18–7.26 (m, 2 H), 7.13 (dd, 1 H, J=1.5 Hz, 7.2 Hz), 7.09–7.11 (m, 1 H), 7.01–7.08 (m, 2 H), 7.00 (dd, 1 H, J=1.5 Hz, 7.2 Hz), 3.49 (hept, 1 H, J=6.6 Hz), 2.37 (s, 3 H), 1.25 (s, 3 H), 1.22 (s, 3 H). $^{13}$C NMR (CDCl$_3$, 75 MHz) δ 149.6, 138.6, 135.5, 133.1, 132.2, 131.1, 130.6, 127.9, 127.0, 126.8, 126.7, 126.1, 30.9, 23.9, 20.9. IR (neat, cm$^{-1}$) 3060, 3012, 2962, 2867. MS (EI) m/z (relative intensity) 242 (100), 225 (80). Anal. Cald. for $C_{16}H_{18}S$, Cald. C, 79.29; H, 7.49. Found C, 79.33; H, 7.62.

EXAMPLE 59

4-(2-Isopropylphenyl)sulfanylanisole

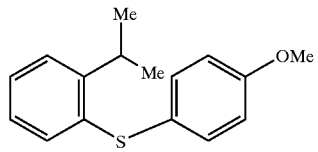

Cu(I) iodide (38 mg, 0.2 mmol) and potassium carbonate (276 mg, 2.0 mmol) were charged into a screw-capped test tube with Teflon-lined septum. The tube was evacuated and backfilled with argon (3 cycles). tert-Amyl alcohol (2-methyl-2-butanol) (1.0 mL, bench grade solvent without degassing and pre-drying), ethylene glycol (111 μL, 2.0 mmol, bench grade solvent), 2-isopropyliodobenzene (246 mg, 1.0 mmol) and 4-methoxythiolphenol (147 μL, 1.2 mmol) were added by syringes at room temperature. The tube was heated to 100° C. and stirred for 24 hours. The reaction mixture was then allowed to reach room temperature. Ethyl acetate (approx. 5 mL) and dodecane (227 μL, GC standard) were added. The aliquot was analyzed GC. The reaction mixture was then filtered and concentrated. The crude product was purified by column chromatography on silica gel using hexane/ethyl acetate=40/1 as eluent to afford white solid as the titled product (241 mg, 94% yield). $R_f$=0.6 (hexane/ethyl acetate=20/1). Melting point; 63–65° C. $^1$H NMR (CDCl$_3$, 300 MHz) δ 7.32 (dt, 2 H, J=2.1 Hz, 8.7 Hz), 7.25–7.28 (m, 1 H), 7.19 (dt, 1 H, J=2.1 Hz, 8.1 Hz), 7.03–7.06 (m, 2 H), 6.88 (dt, 1 H, J=2.4 Hz, 9.0 Hz), 3.82 (s, 3 H), 3.53 (hept, 1 H, J=6.9 Hz), 1.27 (s, 3 H), 1.25 (s, 3 H). $^{13}$C NMR (CDCl$_3$, 75 MHz) δ 159.5, 147.8, 135.9, 134.5, 130.2, 126.9, 126.5, 125.7, 125.6, 115.2, 55.7, 30.7, 23.7. IR (neat, cm$^{-1}$) 3071, 3068, 3011, 2952, 2857. MS (EI) m/z (relative intensity) 258 (100), 241 (20), 149 (30). Anal. Cald. for $C_{16}H_{18}OS$, Cald. C, 74.38; H, 7.02. Found C, 74.57; H, 7.04.

EXAMPLE 60

Di(2-isopropylphenyl) sulfide

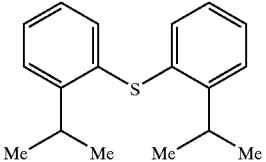

Cu(I) iodide (38 mg, 0.2 mmol) and potassium carbonate (276 mg, 2.0 mmol) were charged into a screw-capped test tube with Teflon-lined septum. The tube was evacuated and backfilled with argon (3 cycles). tert-Amyl alcohol (2-methyl-2-butanol) (1.0 mL, bench grade solvent without degassing and pre-drying), ethylene glycol (111 μL, 2.0 mmol, bench grade solvent), 2-isopropyliodobenzene (246 mg, 1.0 mmol) and 2-isopropylbenzenethiol (90% purity, 202 μL, 1.2 mmol) were added by syringes at room temperature. The tube was heated to 100° C. and stirred for 24 hours. The reaction mixture was then allowed to reach room temperature. Ethyl acetate (approx. 5 mL) and dodecane (227 μL, GC standard) were added. The aliquot was analyzed GC. The reaction mixture was then filtered and concentrated. The crude product was purified by column chromatography on silica gel using hexane as eluent to afford colorless oil as the titled product (245 mg, 91% yield). $R_f$=0.5 (hexane). $^1$H NMR (CDCl$_3$, 300 MHz) δ 7.30 (d, 2 H, J=7.2 Hz), 7.18–7.24 (m, 2 H), 7.03–7.05 (m, 4 H), 3.50 (hept, 2 H, J=6.9 Hz), 1.25 (s, 3 H), 1.23 (s, 3 H). $^{13}$C NMR (CDCl$_3$, 75 MHz) δ 149.2, 134.2, 132.1, 127.6, 126.7, 125.9, 30.9, 23.8. IR (neat, cm$^{-1}$) 3058, 2962, 2929, 2867. MS (EI) m/z (relative intensity) 270 (100), 211 (90). HRMS (EI), Cald. for $C_{18}H_{22}S$ 270.1442. Found 270.1445.

EXAMPLE 61

3-(4-Acetamidophenyl)sulfanylpyridine

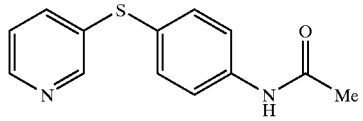

The general procedure in example 39 was followed. 3-Iodopyridine (205 mg, 1.0 mmol), 4-acetamidothiophenol (167 mg, 1.0 mmol), CuI (10 mg, 0.05 mmol), $K_2CO_3$ (276 mg, 2.0 mmol), ethylene glycol (111 μL, 2.0 mmol) and 2-propanol (1.0 mL) were used to obtain the 3-(4-acetamidophenyl)sulfanylpyridine (202 mg, 83% yield) as white solid. Column chromatographic solvent (ethyl acetate). $R_f$=0.4 (ethyl acetate). Melting point; 138–140° C. $^1$H NMR (CDCl$_3$, 300 MHz) δ 8.42 (d, 1 H, J=1.8 Hz), 8.38 (dd, 1 H, J=0.9 Hz, 4.5 Hz), 8.29 (s, 1 H), 7.52 (d, 2 H, J=8.7 Hz), 7.35 (d, 2 H, J=8.4 Hz), 7.18 (dd, 1 H, J=3.0 Hz, 7.8 Hz), 2.17 (s, 3 H). $^{13}$C NMR (CDCl$_3$, 75 MHz) δ 169.0, 149.5, 147.1, 138.9, 136.8, 135.3, 134.0, 127.3, 124.2, 120.9, 24.9. IR (neat, cm$^{-1}$) 3286, 3245, 3176, 3105, 2360, 2342, 1650. MS (EI) m/z (relative intensity) 244 (100), 202 (100). Anal. Cald. for $C_{13}H_{12}N_2OS$, Cald. C, 63.91; H, 4.95. Found C, 63.80; H, 4.93.

EXAMPLE 62

5-(4-Methoxyphenyl)sulfanylindole

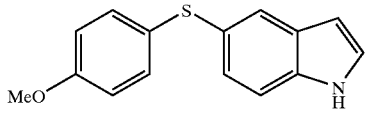

The general procedure in example 39 was followed. 5-Iodoindole (243 mg, 1.0 mmol), 4-methoxythiophenol (123 µL, 1.0 mmol), CuI (10 mg, 0.05 mmol), K$_2$CO$_3$ (276 mg, 2.0 mmol), ethylene glycol (111 µL, 2.0 mmol) and 2-propanol (1.0 mL) were used to obtain the 5-(4-methoxyphenyl)sulfanylindole (228 mg, 90% yield) as white solid. Column chromatographic solvent (hexane/ethyl acetate=5/1). R$_f$=0.3 (hexane/ethyl acetate=5/1). $^1$H NMR (CDCl$_3$, 300 MHz) δ 8.14 (brs, 1 H), 7.69 (s, 1 H), 7.30 (d, 1 H, J=8.4 Hz), 7.12–7.28 (m, 4 H), 6.79 (dt, 2 H, J=2.1 Hz, 9.0 Hz), 6.47–6.49 (m, 1 H), 3.76 (s, 3 H). $^{13}$C NMR (CDCl$_3$, 75 MHz) δ 158.7, 135.2, 132.1, 128.9, 128.8, 126.5, 126.2, 125.2, 124.9, 114.8, 112.1, 102.9, 55.7. IR (neat, cm$^{-1}$) 3417 (broad), 2958, 2939, 2834. MS (EI) m/z (relative intensity) 255 (100), 223 (15). HRMS (EI), Cald. for C$_{15}$H$_{13}$NOS 255.0712. Found 255.0702. Anal. Cald. for C$_{15}$H$_{13}$NOS, Cald. C, 70.56; H, 5.13. Found C, 70.37; H, 5.09.

EXAMPLE 63

Cyclohexyl 3,5-dimethylphenyl sulfide

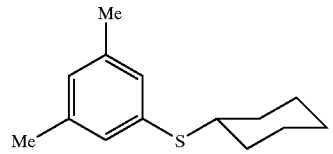

The general procedure in example 39 was followed. 5-Iodo-m-xylene (144 µL, 1.0 mmol), cyclohexylmercaptan (122 µL, 1.0 mmol), CuI (10 mg, 0.05 mmol), K$_2$CO$_3$ (276 mg, 2.0 mmol), ethylene glycol (111 µL, 2.0 mmol) and 2-propanol (1.0 mL) were used to obtain the cyclohexyl 3,5-dimethylphenyl sulfide (156 mg, 71% yield) as colorless oil. Column chromatographic solvent (hexane). R$_f$=0.4 (hexane). $^1$H NMR (CDCl$_3$, 300 MHz) δ 6.99 (s, 2 H), 6.82 (s, 1 H), 3.02–3.10 (m, 1 H), 2.28 (s, 6 H), 1.96–2.00 (m, 2 H), 1.74–1.77 (m, 2 H), 1.56–1.63 (m, 1 H), 1.21–1.42 (m, 4 H). $^{13}$C NMR (CDCl$_3$, 75 MHz) δ 138.4, 134.7, 129.7, 128.7, 46.8, 33.8, 26.5, 26.2, 21.6. IR (neat, cm$^{-1}$) 3088, 3060, 3012, 2962, 2867. MS (EI) m/z (relative intensity) 220 (40), 138 (100), 105 (30). Anal Cald for C$_{14}$H$_{20}$S, Cald. C, 76.30; H, 9.15. Found C, 76.30; H, 9.17.

EXAMPLE 64 n-Butyl 3,5-dimethylphenyl sulfide

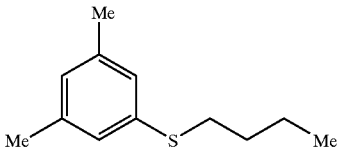

The general procedure in example 39 was followed. 5-Iodo-m-xylene (144 µL, 1.0 mmol), 1-butanethiol (107 µL, 1.0 mmol), CuI (10 mg, 0.05 mmol), K$_2$CO$_3$ (276 mg, 2.0 mmol), ethylene glycol (111 µL, 2.0 mmol) and 2-propanol (1.0 mL) were used to obtain the n-butyl 3,5-dimethylphenyl sulfide (184 mg, 95% yield) as colorless oil. Column chromatographic solvent (hexane). R$_f$=0.5 (hexane). $^1$H NMR (CDCl$_3$, 300 MHz) δ 6.92 (s, 2 H), 6.77 (s, 1 H), 2.89 (t, 2 H, J=7.2 Hz), 2.27 (s, 6 H), 1.41–1.65 (m, 4 H), 0.92 (t, 3 H, J=7.5 Hz). $^{13}$C NMR (CDCl$_3$, 75 MHz) δ 138.5, 136.7, 127.7, 126.6, 33.5, 31.6, 22.4, 21.7, 14.1. IR (neat, cm$^{-1}$) 3083, 3050, 3011, 2965, 2867. MS (EI) m/z (relative intensity) 194 (70), 138 (100). Anal Cald for C$_{12}$H$_{18}$S, Cald. C, 74.16; H, 9.34. Found C, 73.89; H, 9.32.

EXAMPLE 65

4-Benzylsulfanylanisole

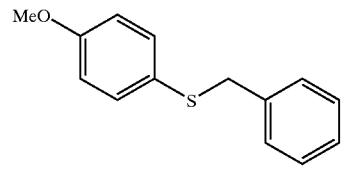

The general procedure in example 39 was followed. 4-Iodoanisole (234 mg, 1.0 mmol), benzylmercaptan (117 µL, 1.0 mmol), CuI (10 mg, 0.05 mmol), K$_2$CO$_3$ (276 mg, 2.0 mmol), ethylene glycol (111 µL, 2.0 mmol) and 2-propanol (1.0 mL) were used to obtain the 4-benzylsulfanylanisole (206 mg, 90% yield) as colorless solid. Column chromatographic solvent (hexane/ethyl acetate=50/1). Melting point; 48–50° C. R$_f$=0.3 (hexane/ethyl acetate=40/1). $^1$H NMR (CDCl$_3$, 300 MHz) δ 7.14–7.24 (m, 7 H), 6.76 (dt, 2 H, J=8.7 Hz, 2.1 Hz), 3.97 (s, 2 H), 3.76 (s, 3 H). $^{13}$C NMR (CDCl$_3$, 75 MHz) δ 159.3, 138.3, 134.3, 129.1, 128.5, 127.2, 126.2, 114.6, 55.6, 41.6. IR (neat, cm$^{-1}$) 3043, 3012, 2982, 2861. MS (EI) m/z (relative intensity) 230 (30), 91 (100). Anal Cald for C$_{14}$H$_{14}$OS, Cald. C, 73.01; H, 6.13. Found C, 72.86; H, 5.93.

EXAMPLE 66

6-(3,5-Dimethylphenyl)mercaptohexanol

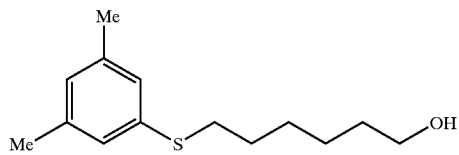

The general procedure in example 39 was followed. 5-Iodo-m-xylene (144 µL, 1.0 mmol), 6-mercaptohexanol (137 μL, 1.0 mmol), CuI (10 mg, 0.05 mmol), K$_2$CO$_3$ (276 mg, 2.0 mmol), ethylene glycol (111 μL, 2.0 mmol) and 2-propanol (1.0 mL) were used to obtain the 6-(3,5-dimethylphenyl)mercaptohexanol (212 mg, 92% yield) as colorless oil. Column chromatographic solvent (hexane/ ethyl acetate=3/1). R$_f$=0.4 (hexane/ethyl acetate=2/1). $^1$H NMR (CDCl$_3$, 300 MHz) δ 6.92 (s, 2 H), 6.78 (s, 1 H), 3.62 (q, 2 H, J=4.8 Hz), 2.90 (t, 2 H, J=7.2 Hz), 2.27 (s, 6 H), 1.30–1.68 (m, 9 H). $^{13}$C NMR (CDCl$_3$, 75 MHz) δ 138.6, 136.5, 127.8, 126.7, 63.2, 33.8, 33.0, 29.5, 28.9, 25.7, 21.7. IR (neat, cm$^{-1}$) 3320 (broad), 3060, 3022, 2972, 2847. MS (EI) m/z (relative intensity) 238 (40), 138 (100). Anal Cald for C$_{14}$H$_{22}$OS, Cald. C, 70.54; H, 9.30. Found C, 70.29; H, 9.33.

EXAMPLE 67

General Considerations for Copper-Catalyzed Conversion of Aryl Bromides into Aryl Iodides The following technique was used for the reactions that were performed in Schlenk tubes. After a 15 mL Schlenk tube with a screw thread (Kontes) was dried in an oven at 100° C. overnight, it was equipped with a 10×3 mm Teflon-coated stirring bar and a Teflon valve, evacuated, and backfilled with argon. The solid reagents were weighed out in the air by adding them directly to the Schlenk tube with the Teflon valve removed. The Schlenk tube was again fitted with the Teflon valve, evacuated and backfilled with argon. Under positive pressure of argon, the Teflon valve was replaced with a rubber septum, and the liquid reagents were added to the Schlenk tube using Hamilton mycrosyringes (if <500 μL) or all polypropylene/polyethylene disposable syringes (if >500 μL). The rubber septum was replaced with a Teflon valve under positive pressure of argon. The Schlenk tube was sealed and heated in an oil bath for the specified time while stirring at the maximum rate achievable on a magnetic stirrer (sometimes the stirring rate had to be slightly reduced to minimize excessive depositing of the solids on the walls of the Schlenk tube). IR spectra were recorded on a Perkin-Elmer FT-IR 2000 instrument for all previously unknown compounds. Elemental analyses were performed by Atlantic Microlabs, Inc., Norcross, Ga. $^1$H NMR and $^{13}$C NMR spectra were recorded on a Bruker 400 MHz instrument with chemical shifts reported relative to residual deuterated solvent peaks or tetramethylsilane internal standard. Gas chromatographic analysis was performed on an Agilent 6890 instrument with an FID detector and an Agilent 10 m×0.10 gin i.d. HP-1 capillary column. Mass spectra (GC/MS) were recorded on a Hewlett Packard model GCD. In most cases, the aryl iodide product also contained traces (0.5–1.0%) of the aryl bromide starting material due to the separation difficulties.

General Procedure for Copper-Catalyzed Conversion of Aryl Bromides into Aryl Iodides A Schlenk tube was charged with CuI (9.6 mg, 0.050 mmol, 5.0 mol %), aryl bromide (if it is a solid at room temperature; 1.00 mmol), NaI (300 mg, 2.00 mmol), briefly evacuated and backfilled with argon. Racemic trans-N,N'-dimethyl-1,2-cyclohexanediamine (16 μL, 0.10 mmol, 10 mol %), aryl bromide (if it is a liquid at room temperature; 1.00 mmol), and dioxane (1.0 mL) were added under argon. The Schlenk tube was sealed with a Teflon valve and the reaction mixture was stirred at 110° C. for 22–24 h. The resulting suspension was allowed to reach room temperature, diluted with 30% aq ammonia (5 mL), poured into water (20 mL), and extracted with dichloromethane (3×15 mL). The combined organic phases were dried (MgSO$_4$ or Na$_2$SO$_4$), concentrated, and the residue was purified by flash chromatography on silica gel to provide the desired product.

EXAMPLE 68

Procedure for Ligand Screening for the Halogen Exchange Reaction

Nine Schlenk tubes were charged with CuI (9.6 mg, 0.050 mmol, 5.0 mol %), ligand (if solid at room temperature; 0.10 mmol, 10 mol %), sodium iodide (300 mg, 2.00 mmol), evacuated and backfilled with argon. Ligand (if liquid at room temperature, 0.10 mmol, 10 mol %), 5-bromo-m-xylene (136 μL, 1.00 mmol) and dioxane (1.0 mL) were added to each Schlenk tube. The reaction mixtures were stirred at 110° C. for 22 h. The resulting suspensions were allowed to reach room temperature. Ethyl acetate (2 mL), water (2 mL), and dodecane (230 μL, internal GC standard) were added to each reaction mixture. A 50 μL sample of the supernatant solution was diluted with ethyl acetate (1 mL) and analyzed by GC. The results are compiled below, and represent averaged data from two runs.

Ligand Screening for the Halogen Exchange Reaction

| Ligand | Amount of ligand | Conversion of aryl bromide, % | GC yield of aryl iodide, % |
|---|---|---|---|
| No ligand | None | 0.1 | <0.1 |
| rac-trans- 1,2-cyclohexanediamine (H$_2$N, NH$_2$) | 12 μL (0.10 mmol) | 77 | 73 |
| rac-trans- N,N'-dimethyl-1,2-cyclohexanediamine (Me(H)N, N(H)Me) | 16 μL (0.10 mmol) | 99.3 | 98 |
| rac-trans- N,N'-diethyl-1,2-cyclohexanediamine (Et(H)N, N(H)Et) | 19.5 μL (0.101 mmol) | 23 | 22 |
| H$_2$N⁀NH$_2$ | 6.8 μL (0.10 mmol) | 73 | 69 |
| Me(H)N⁀N(H)Me | 11 μL (0.10 mmol) | 98 | 96 |
| H$_2$N⁀⁀NH$_2$ | 8.5 μL (0.10 mmol) | 72 | 69 |
| phenanthroline | 18.5 mg (0.103 mmol) | 6 | 4 |
| Ph$_3$P | 26.5 mg (0.101 mmol) | <0.1 | <0.1 |

EXAMPLE 69

2-(3-Iodophenyl)-5-(2-naphthyl)-1,3,4-oxadiazole

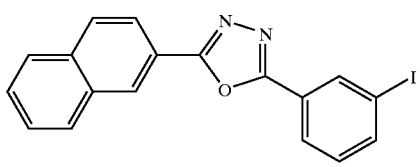

A Schlenk tube was charged with CuI (9.6 mg, 0.050 mmol, 5.0 mol %), 2-(3-bromophenyl)-5-(2-naphthyl)-1,3,4-oxadiazole (352 mg, 1.00 mmol), NaI (300 mg, 2.00 mmol), briefly evacuated and backfilled with argon. Racemic trans-N,N'-dimethyl-1,2-cyclohexanediamine (16 µL, 0.10 mmol, 10 mol %) and dioxane (1.0 mL) were added under argon. The Schlenk tube was sealed with a Teflon valve and the reaction mixture was stirred at 110° C. for 24 h. The resulting light green-gray suspension was allowed to reach room temperature, diluted with 30% aq ammonia (5 mL), poured into water (20 mL), and extracted with dichloromethane (3×15 mL). The combined organic phases were dried ($Na_2SO_4$), concentrated to ca. 2 mL volume. The product was allowed to crystallize at room temperature. After 15 min, hexane (20 mL) was added, the mixture was kept at room temperature for 15 h, and finally filtered to provide 382 mg (96% yield) of 2-(3-iodophenyl)-5-(2-naphthyl)-1,3,4-oxadiazole as white, fine needles. Mp: 156–158° C. $^1$H NMR (400 MHz, $CDCl_3$): δ 8.64 (s, 1H), 8.53 (t, J=1.8 Hz, 1H), 8.22 (dd, J=8.6, 1.8 Hz, 1H), 8.18 (dt, J=7.9, 1.2 Hz, 1H), 8.03–7.93 (m, 2H), 7.95–7.88 (m, 2H), 7.65–7.53 (m, 2H), 7.30 (t, J=7.9 Hz, 1H). $^{13}$C NMR (100 MHz, $CDCl_3$): δ 165.1, 163.2, 140.6, 135.5, 134.8, 132.8, 130.7, 129.1, 128.9, 128.1, 128.0, 127.5, 127.2, 126.1, 125.8, 123.2, 120.8, 94.4. IR (neat, $cm^{-1}$): 1558, 1540, 753, 731. Anal. Calcd. for $C_{18}H_{11}IN_2O$: C, 54.29; H, 2.78. Found: C, 54.29; H, 2.74.

EXAMPLE 70

4-Iodo-2-nitrotoluene

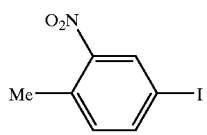

Following the general procedure in example 67, 4-bromo-2-nitrotoluene (216 mg, 1.00 mmol) was converted into 4-iodo-2-nitrotoluene. Purification of the crude product by column chromatography on silica gel (hexane-ethyl acetate 10:1) provided the desired product as pale yellow fine needles (249 mg, 95% yield). Mp: 57–58° C. (lit. 59° C. See Arotsky, J.; Darby, A. C.; Hamilton, J. B. A. *J Chem. Soc., Perkin Trans.* 2 1973, 595). The $^1$H spectrum matched the one reported by Arotsky, et al.[2] $^{13}$C NMR (100 MHz, $CDCl_3$): δ 142.2, 134.7, 133.6, 90.2, 20.6.

EXAMPLE 71

3-Iodopropiophenone

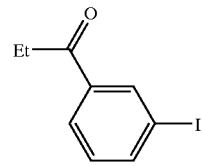

Following the general procedure in example 67, 3-bromopropiophenone (214 mg, 1.00 mmol) was converted into 3-iodopropiophenone. Purification of the crude product by column chromatography on silica gel (hexane-ethyl acetate 10:1) provided the desired product as a colorless oil (256 mg, 98% yield). The $^1$H spectrum matched the one reported by Fukuyama, et al. Fukuyama, N.; Nishino, H.; Kurosawa, K. *Bull Chem. Soc. Jpn.* 1987, 60, 4363. $^{13}$C NMR (100 MHz, $CDCl_3$): δ 199.3, 141.6, 138.6, 136.9, 130.2, 127.0, 94.4, 31.8, 8.0.

EXAMPLE 72

4-Iodophenylacetonitrile

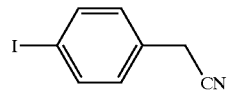

Following the general procedure in example 67, 4-bromophenylacetonitrile (197 mg, 1.00 mmol) was converted into 4-iodophenylacetonitrile. Purification of the crude product by column chromatography on silica gel (hexane-ethyl acetate 5:1) provided the desired product as a tan solid (236 mg, 97% yield). Mp: 53–54° C. (lit. 56–57° C. See Maggioni & C. S. p. A. Fr. Patent M1687, Mar. 11, 1963; *Chem. Abstr.* 1963, 59, 8764b). $^1$H NMR (400 MHz, $CDCl_3$): δ7.73–7.68 (m, 2H), 7.10–7.05 (m, 2H), 3.70 (s, 2H). $^{13}$C NMR (100 MHz, $CDCl_3$): δ 138.2, 129.7, 129.5, 117.2, 93.5, 23.2.

EXAMPLE 73

Ethyl 4-iodophenylacetate

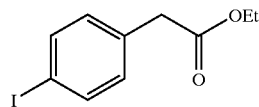

Following the general procedure in example 67, ethyl 4-bromophenylacetate (244 mg, 1.00 mmol) was converted into ethyl 4-iodophenylacetate. The reaction mixture was allowed to reach room temperature and filtered through a silica gel plug (1×1 cm) eluting with ethyl acetate (50 mL). The filtrate was concentrated and the residue was purified by column chromatography on silica gel (hexane-ethyl acetate 10:1) to provide the desired product as a pale tan, low melting solid (283 mg, 98% yield). Mp: 26–27° C. (lit. 28° C. See Watkinson, J. G.; Watson, W.; Yates, B. L. *J. Chem. Soc.* 1963, 5437). $^1$H NMR (400 MHz, $CDCl_3$): δ 7.67–7.60 (m, 2H), 7.06–7.00 (m, 2H), 4.14 (q, J=7.1 Hz, 2H), 3.54 (s, 2H), 1.24 (t, J=7.1 Hz). $^{13}$C NMR (100 MHz, $CDCl_3$): δ 171.0, 137.5, 133.7, 131.2, 92.5, 61.0, 40.8, 14.1.

EXAMPLE 74

Preparation of 3-iodocinnamic Acid through an In Situ Generated Trimethylsilyl Ester

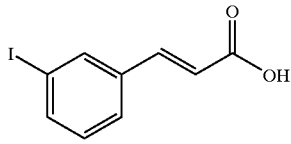

A Schlenk tube was charged with CuI (9.6 mg, 0.050 mmol, 5.0 mol %), 3-bromocinnamic acid (228 mg, 1.00 mmol), NaI (300 mg, 2.00 mmol), evacuated and backfilled with argon. Racemic trans-N,N'-dimethyl-1,2-cyclohexanediamine (16 μL, 0.10 mmol, 10 mol %), 1,1,1,3,3,3-hexamethyldisilazane (211 μL, 1.00 mmol), and dioxane (1.0 mL) were added under argon. The Schlenk tube was sealed with a Teflon valve and the reaction mixture was stirred at 110° C. for 22 h. The resulting suspension was allowed to reach room temperature, poured into ether (20 mL), and washed with a solution of $Na_2S_2O_5$ (100 mg) in 10% aq HCl (3×20 mL). The organic phase was dried ($Na_2SO_4$) and concentrated. The residue was dissolved in hot ethanol (5 mL), and hot water (5 mL) was added to the solution. The product was allowed to crystallize at 0° C. for 15 h to provide 256 mg (93% yield) of 3-iodocinnamic as pale yellow needles. Mp: 186–188° C. (lit. 180–182° C. See Yuzikhin, O. S.; Vasil'ev, A. V.; Rudenko, A. P. Russ. *J. Org. Chem.* 2000, 36, 1743). $^1$H NMR (400 MHz, DMSO-$d_6$): δ 12.47 (s, 1H), 8.08 (s, 1H), 7.77 (d, J=7.8 Hz, 1 H), 7.72 (d, J=7.8 Hz, 1H), 7.52 (d, J=16.0 Hz, 1 H), 7.22 (t, J=7.8 Hz, 1H), 6.58 (d, J=16.0 Hz, 1H). $^{13}$C NMR (100 MHz, DMSO-$d_6$): δ 167.3, 142.3, 138.6, 136.6, 136.5, 130.9, 127.4, 120.6, 95.4.

EXAMPLE 75

N-Allyl-4-bromobenzenesulfonamide

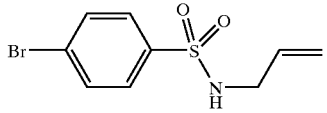

To a solution of 4-bromobenzenesulfonamide (6.80 g 26.6 mmol) in dichloromethane (50 mL) was added allylamine (5.0 mL, 66.5 mmol) at 0° C. The clear, colorless solution was stirred at room temperature for 1 h. The reaction mixture was poured into ether (100 mL) and washed with 10% aq HCl (50 mL), water (2×50 mL), and saturated aq $NaHCO_3$ (50 mL). The organic phase was dried ($MgSO_4$) and concentrated. The residue crystallized upon treatment with hexane to provide 7.03 g (96% yield) of the desired product as fine, white crystals. Mp: 63–65° C. (lit. 64–65° C. See Keasling, H. H.; Schumann, E. L.; Veldkamp, W. *J. Med. Chem.* 1965, 8, 548). $^1$H NMR (400 MHz, $CDCl_3$): δ 7.77–7.72 (m, 2H), 7.69–7.64 (m, 2H), 5.71 (ddt, J=17.1, 10.2, 6.0 Hz, 1H), 5.18 (dq, J=17.1, 1.5 Hz, 1H), 5.12 (dq, J=10.2, 1.5 Hz, 1H), 4.67 (t, J=6.0 Hz, 1H), 3.61 (tt, J=6.0, 1.5 Hz, 2H). $^{13}$C NMR (100 MHz, $CDCl_3$): δ 139.0, 132.6, 132.4, 128.6, 127.6, 118.0, 45.7.

EXAMPLE 76

N-Allyl-4-iodobenzenesulfonamide

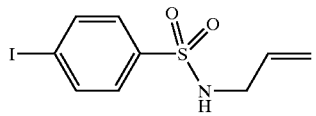

Following the general procedure in example 67, N-allyl-4-bromo-benzenesulfonamide (277 mg, 1.00 mmol) was converted into N-allyl-4-iodobenzenesulfonamide. Purification of the crude product by column chromatography on silica gel (hexane-ethyl acetate 4:1) provided the desired product as white crystals (309 mg, 96% yield). Mp: 76–77° C. $^1$H NMR (400 MHz, $CDCl_3$): δ 7.91–7.85 (m, 2H), 7.61–7.56 (m, 2H), 5.71 (ddt, J=17.1, 10.2, 6.0 Hz, 1H), 5.18 (dq, J=17.1, 1.5 Hz, 1H), 5.12 (dq, J=10.2, 1.5 Hz, 1H), 4.67 (t, J=6.0 Hz, 1H), 3.61 (tt, J=6.0, 1.5 Hz, 2H). $^{13}$C NMR (100 MHz, $CDCl_3$): δ 139.6, 138.3, 132.6, 128.5, 118.0, 100.1, 45.7. IR (neat, cm$^{-1}$): 3264, 1571, 1329, 1162, 738. Anal. Calcd. for $C_9H_{10}INO_2S$: C, 33.45; H, 3.12. Found: C, 33.70; H, 3.08.

EXAMPLE 77

2-Fluoro-4-iodoacetanilide

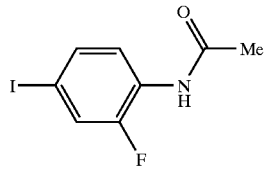

Following the general procedure in example 67, 2-fluoro-4-bromoacetanilide (233 mg, 1.00 mmol) was converted into 2-fluoro-4-iodoacetanilide. The reaction mixture was allowed to reach room temperature and filtered through a silica gel plug (1×0.5 cm) eluting with ethyl acetate (50 mL). The filtrate was concentrated and the residue was purified by column chromatography on silica gel (hexane-ethyl acetate 3:2) to provide the desired product as a white solid (265 mg, 95% yield). Mp: 153–154° C. (lit. 152–154° C. See Krueger, G.; Keck, J.; Noll, K.; Pieper, H. *Arzneim.-Forsch.* 1984, 34, 1612). $^1$H NMR (400 MHz, DMSO-$d_6$): δ 9.81 (s, 1H), 7.74 (t, J=8.4 Hz, 1H), 7.65 (dd, J=10.4, 1.9 Hz, 1H), 7.50 (d, J=8.4 Hz, 1H), 2.08 (s, 3H). $^{13}$C NMR (100 MHz, $CDCl_3$): δ 168.8 (s), 153.0 (d, J=250 Hz), 133.2 (d, J=3.5 Hz), 126.4 (d, J=11 Hz), 125.4 (s), 124.1 (d, J=22 Hz), 87.0 (d, J=7.1 Hz), 23.6 (s).

EXAMPLE 78

5-Iodoindole

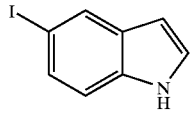

Following the general procedure in example 67, 5-bromoindole (197 mg, 1.00 mmol) was converted into 5-iodoindole. Purification of the crude product by column chromatography on silica gel (hexane-ethyl acetate 10:1 followed by hexane-ethyl acetate 3:1) provided the desired product as a white solid (238 mg, 98% yield). Mp: 99–100° C. (lit. 99–102° C.). The $^1$H spectrum matched the one reported by Somei, et al. Somei, M.; Saida, Y.; Funamoto, T.; Ohta, T. Chem. Pharm. Bull. 1987, 35, 3146. $^{13}$C NMR (100 MHz, CDCl$_3$): δ 134.7, 130.4, 130.2, 129.5, 124.9, 112.9, 101.9, 83.2.

EXAMPLE 79

2-Amino-5-iodopyridine

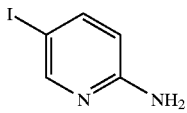

Following the general procedure in example 67, 2-amino-5-bromopyridine (173 mg, 1.00 mmol) was converted into 2-amino-5-iodopyridine. Purification of the crude product by column chromatography on silica gel (hexane-ethyl acetate 2:3) provided the desired product as a pale tan solid (209 mg, 95% yield). Mp: 128–129° C. (lit. 126–128° C. See Bochis, R. J.; Dybas, R. A.; Eskola, P.; Kulsa, P.; Linn, B. O.; Lusi, A.; Meitzner, E. P.; Milkowski, J.; Mrozik, H.; Olen, L. E.; Peterson, L. H.; Tolman, R. L.; Wagner, A. F.; Waksmunski, F. S.; Egerton, J. R.; Ostlind, D. A. J. Med. Chem. 1978, 21, 235). The $^1$H spectrum, matched the one reported by Trapani, et al. Trapani, G.; Franco, M.; Ricciardi, L.; Latrofa, A.; Genchi, G.; Sanna, E.; Tuveri, F.; Cagetti, E.; Biggio, G.; Liso, G. J. Med. Chem. 1997, 40, 3109. $^{13}$C NMR (100 MHz, CDCl$_3$): δ 157.2, 153.8, 145.3, 110.8, 77.9.

EXAMPLE 80

3-Iodoquinoline

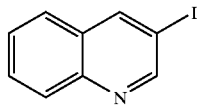

Following the general procedure in example 67, 3-bromoquinoline (136 4L, 1.00 mmol) was converted into 3-iodoquinoline. Purification of the crude product by column chromatography on silica gel (hexane-ethyl acetate 8:1) provided the desired product as a pale yellow solid (248 mg, 97% yield). Mp: 58–59° C. (lit. 61–62° C. See Leonard, N. J.; Foster, R. L. J. Am. Chem. Soc. 1952, 74, 3671). $^1$H NMR (400 MHz, CDCl$_3$): δ 9.03 (d, J=2.1 Hz, 1 H), 8.52 (d, J=2.1 Hz, 1 H), 8.06 (d, J=8.9 Hz, 1 H), 7.75–7.66 (m, 2H), 7.58–7.52 (m, I H). $^{13}$C NMR (100 MHz, CDCl$_3$): δ 155.5, 146.2, 143.6, 130.0, 129.8, 129.4, 127.3, 126.7, 89.8.

EXAMPLE 81

(±)-1-(4-Iodophenyl)-1-(2-pyridyl)-3-dimethylaminopropane

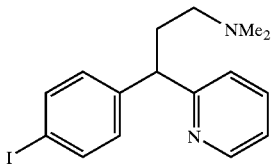

Following the general procedure in example 67, (±)-1-(4-bromophenyl)-1-(2-pyridyl)-3-dimethylaminopropane (256 μL, 1.00 mmol) was converted into (±)-1-(4-iodophenyl)-1-(2-pyridyl)-3-dimethylaminopropane. Purification of the crude product by column chromatography on silica gel (dichloromethane-dichloromethane (saturated with 30% aq ammonia)-methanol 30:20:2) provided the desired product as a pale tan oil (365 mg, 100% yield). $^1$H NMR (400 MHz, CDCl$_3$): δ 8.56 (ddd, J=4.8, 1.8, 0.9 Hz, 1H), 7.63–7.57 (m, 2H), 7.55 (td, J=7.7, 1.8 Hz, 1H), 7.16–7.06 (m, 4H), 2.46–2.32 (m, 1H), 2.24–2.10 (m, 9H). $^{13}$C NMR (100 MHz, CDCl$_3$): δ 162.9, 149.4, 143.4, 137.4, 136.4, 130.1, 122.7, 121.4, 91.8, 57.6, 50.7, 45.5, 32.8. IR (neat, cm$^{-1}$): 1590, 1569, 1482, 1471, 1432, 1006, 749. HRMS-El calcd for C$_{16}$H$_{20}$IN$_2$ (M+H$^+$), 367.0665; found, 367.0679.

EXAMPLE 82

Preparation of 3-iodobenzo[b]thiophene using m-xylene-diglyme Solvent Mixture

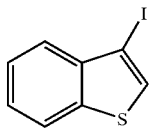

A Schlenk tube was charged with CuI (9.6 mg, 0.050 mmol, 5.0 mol %), NaI (300 mg, 2.00 mmol), evacuated and backfilled with argon. Racemic trans-N,N'-dimethyl-1,2-cyclohexanediamine (16 μL, 0.10 mmol, 10 mol %), 3-bromobenzo[b]thiophene (131 μL, 1.00 mmol), m-xylene (0.80 mL), and diglyme (0.20 mL) were added under argon. The Schlenk tube was sealed with a Teflon valve and the reaction mixture was stirred at 130° C. for 22 h. The resulting suspension was allowed to reach room temperature, diluted with hexane (10 mL), and filtered through silica gel (2×2 cm) eluting with hexane (50 mL). The filtrate was concentrated, and the residue was purified by flash chromatography on silica gel (hexane) to provide 3-iodobenzo[b]thiophene (243 mg, 93% yield) as a pale yellow liquid. $^1$H NMR (400 MHz, CDCl$_3$): δ 7.88 (d, J=8.0 Hz, 1H), 7.80 (d, J=7.9 Hz, 1H), 7.64 (s, 1H), 7.53–7.40 (m, 2H). $^{13}$C NMR (100 MHz, CDCl$_3$): δ 140.2, 138.3, 129.1, 125.22, 125.16, 122.4, 78.2. IR (neat, cm$^{-1}$): 1416, 1305, 1251, 749, 723. Anal. Calcd. for C$_8$H$_5$IS: C, 36.94; H, 1.94. Found: C, 37.14; H, 1.98.

EXAMPLE 83

Preparation of 1-iodo-2-cyclohexylbenzene using N-pentanol as the Solvent

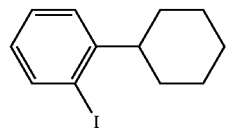

A Schlenk tube was charged with CuI (9.6 mg, 0.050 mmol, 5.0 mol %), NaI (300 mg, 2.00 mmol), evacuated and backfilled with argon. Racemic trans-N,N'-dimethyl-1,2-cyclohexanediamine (16 µL, 0.10 mmol, 10 mol %), 1-bromo-2-cyclohexylbenzene (97% pure; Lancaster; 186 µL, 1.00 mmol), n-pentanol (1 mL) were added under argon. The Schlenk tube was sealed with a Teflon valve and the reaction mixture was stirred at 130° C. for 40 h. The resulting suspension was allowed to reach room temperature and filtered through silica gel (1×0.5 cm) eluting with hexane (50 mL). The filtrate was concentrated, and the residue was purified by flash chromatography on silica gel (hexane) to provide the known 1-iodo-2-cyclohexylbenzene (283 mg, 99% yield; ca. 97% pure) as a colorless liquid. See McGuine, T. H.; Dull, M. F. *J. Am. Chem. Soc.* 1947, 69, 1469. $^1$H NMR (400 MHz, CDCl$_3$): δ 7.85 (dd, J=7.5, 1.2 Hz, 1H), 7.32 (td, J=7.5, 1.2 Hz, 1H), 7.23 (dd, J=7.5, 1.7 Hz, 1H), 6.90 (td, J=7.5, 1.7 Hz, 1H), 2.81 (tt, J=11.7, 3.0 Hz, 1H), 1.97–1.74 (m, 5H), 1.55–1.23 (m, 5H). $^{13}$C NMR (100 MHz, CDCl$_3$): δ 149.3, 139.5, 128.4, 127.6, 126.6, 101.5, 48.5, 33.4, 26.8, 26.1.

EXAMPLE 84

Preparation of 4-iodobiphenyl Using 1,3-propanediamine as the Ligand

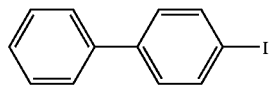

A Schlenk tube was charged with CuI (9.6 mg, 0.050 mmol, 5.0 mol %), 4-bromobiphenyl (234 mg, 1.00 mmol), NaI (300 mg, 2.00 mmol), evacuated and backfilled with argon. 1,3-Propanediamine (8.4 µL, 0.10 mmol, 10 mol %) and n-pentanol (1.0 mL) were added under argon. The Schlenk tube was sealed with a Teflon valve and the reaction mixture was stirred at 130° C. for 22 h. The resulting suspension was allowed to reach room temperature, diluted with 30% aq ammonia (2 mL), poured into water (20 mL), and extracted with dichloromethane (3×15 mL). The combined organic phases were dried (MgSO$_4$), concentrated, and the residue was purified by flash chromatography on silica gel (hexane) to provide 269 mg (96% yield) of 4-iodobiphenyl as a white solid. Mp: 113–114° C. (lit. 112.5–113.5° C. See lbuki, E.; Ozasa, S.; Murai, K. *Bull. Chem. Soc. Jpn.* 1975, 48, 1868). The $^1$H and $^{13}$C spectra matched those reported in Dektar, J. L.; Hacker, N. P. *J. Org. Chem.* 1990, 55, 639.

EXAMPLE 85

2-Iodo-3-methyl-2-butene

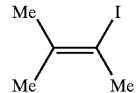

A 50 mL Schlenk tube was charged with CuI (382 mg, 2.01 mmol, 5.0 mol %), NaI (9.00 g, 60.0 mmol), evacuated and backfilled with argon. N,N'-Dimethylethylenediamine (426 µL, 4.00 mmol, 10 mol %), 2-bromo-3-methyl-2-butene (4.65 µL, 40.1 mmol), and n-butanol (20 mL) were added under argon. The Schlenk tube was sealed with a Teflon valve and the reaction mixture was stirred at 120° C. for 24 h. The resulting tan suspension was allowed to reach room temperature, poured into pentane (200 mL) and washed with a solution of 30% aq ammonia (10 mL) in water (200 mL), followed by water (3×200 mL). The organic phase was dried (MgSO$_4$) and concentrated to ~10 mL volume. The residue was distilled collecting the fraction boiling at 120–140° C. to give 6.08 g (77% yield) of 2-iodo-3-methyl-2-butene as a colorless liquid (>95% pure). The $^1$H spectrum matched the one reported by Sherrod, et al. $^{13}$C NMR (100 MHz, CDCl$_3$): δ 135.9, 93.2, 31.4, 30.3, 18.9. Sherrod, S. A.; Bergman, R. G. *J. Am. Chem. Soc.* 1971, 93, 1925.

EXAMPLE 86

Partial Conversion of 4-chlorotoluene into 4-iodotoluene

A Schlenk tube was charged with CuI (19.5 mg, 0.102 mmol, 5.0 mol %), NaI (450 mg, 3.00 mmol), evacuated and backfilled with argon. Racemic trans-N,N'-dimethyl-1,2-cyclohexanediamine (31.5 µL, 0.200 mmol, 10 mol %), 4-chlorotoluene (237 µL, 2.00 mmol), and n-pentanol (0.50 mL) were added under argon. The Schlenk tube was sealed with a Teflon valve and the reaction mixture was stirred at 130° C. for 24 h. The resulting dark green-gray suspension was allowed to reach room temperature. Ethyl acetate (3 mL) and dodecane (internal GC standard, 460 µL) were added to the reaction mixture. A 50 µL sample of the supernatant solution was diluted with ethyl acetate (1 mL) and analyzed by GC to provide 35% conversion of 4-chlorotoluene and 33% yield of 4-iodotoluene.

EXAMPLE 87

Conversion of 5-Bromo-m-xylene into 5-Iodo-m-xylene Using NaI or KI in n-BuOH or DMF (FIG. 11)

Four Schlenk tubes were charged with CuI (19.5 mg, 0.102 mmol, 5.0 mol %) and sodium iodide (600 mg, 4.00 mmol) or potassium iodide (665 mg, 4.01 mmol). The Schlenk tubes were evacuated and backfilled with argon. Racemic trans-N,N'-dimethyl-1,2-cyclohexanediamine (31.5 µL, 0.200 mmol, 10 mol %), 5-bromo-m-xylene (272 µL, 2.00 mmol), sec-butylbenzene (62 µL, internal GC standard), and n-butanol (2.0 mL) or DMF (2.0 mL) were added to each Schlenk tube. The reaction mixtures were stirred at 110° C. in an oil bath. After certain time intervals, the Schlenk tubes were briefly (ca. 1–2 min) removed from the oil bath, the Teflon valve was removed under a positive pressure of argon, and a sample (ca. 10–50 µL) was taken with a Pasteur pipette under a positive pressure of argon (the sample was drawn into the pipette by the capillary forces). The Teflon valve was then quickly replaced, and heating of the reaction mixture was continued. The sample taken with the Pasteur pipette was diluted with ethyl acetate (1 mL) and analyzed by GC. The results are compiled in FIG. 11, and represent averaged data from two runs.

EXAMPLE 88

Figure 12:
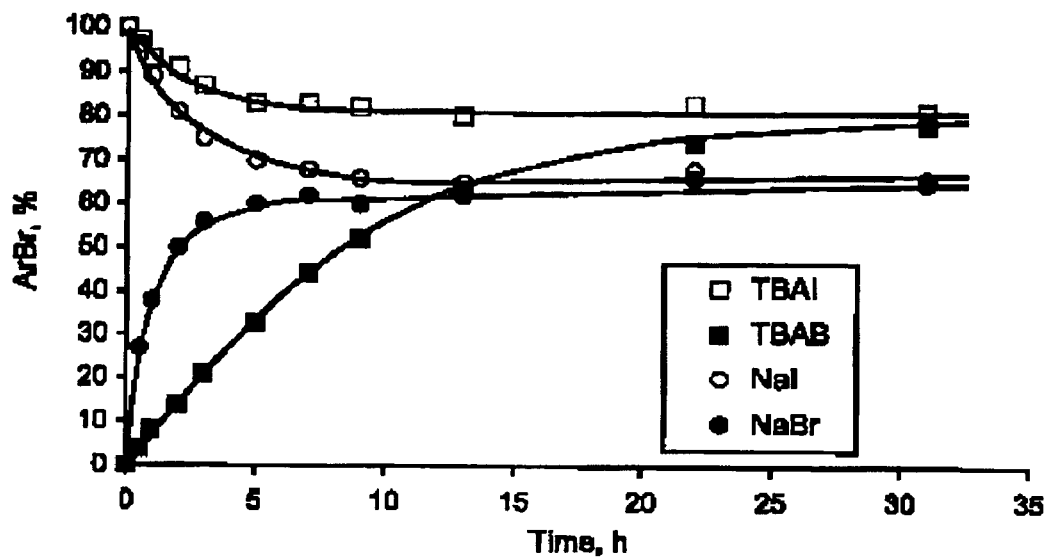
FIG. 12 depicts conversion of 5-bromo-m-xylene into 5-iodo-m-xylene using NaI or TBAI (tetrabutylammonium iodide).
Figure 13:
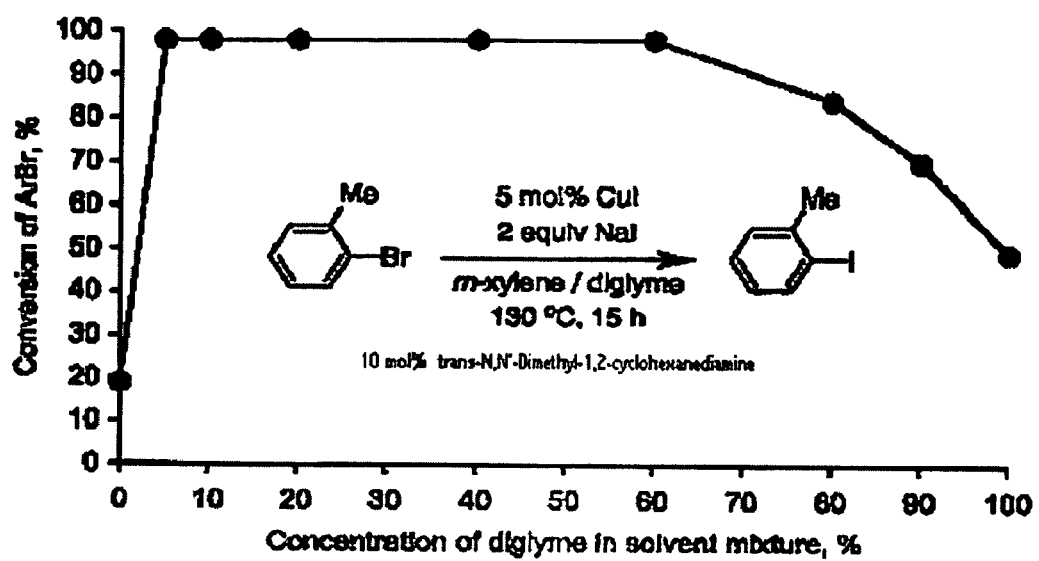
FIG. 13 depicts a halogen exchange reaction performed in a m-xylene/diglyme solvent mixture of variable composition.

Halogen Exchange in 5-Bromo-m-xylene or 5-Iodo-m-xylene Using Different Halide Sources (FIG. 12)

Conversion of 5-bromo-m-xylene into 5-iodo-m-xylene

Two Schlenk tubes were charged with CuI (19.5 mg, 0.102 mmol, 5.0 mol %) and sodium iodide (300 mg, 2.00 mmol) or tetrabutylammonium iodide (740 mg, 2.00 mmol). The Schlenk tubes were evacuated and backfilled with argon. Racemic trans-N,N'-dimethyl-1,2-cyclohexanediamine (31.5 µL, 0.200 mmol, 10 mol %), 5-bromo-m-xylene (272 µL, 2.00 mmol), sec-butylbenzene (62 µL, internal GC standard), and DMF (2.0 mL) were added to each Schlenk tube. The reaction mixtures were stirred at 110° C. in an oil bath. After certain time intervals, the Schlenk tubes were briefly (ca. 1–2 min) removed from the oil bath, the Teflon valve was removed under a positive pressure of argon, and a sample (ca. 10–50 µL) was taken with a Pasteur pipette under a positive pressure of argon (the sample was drawn into the pipette by the capillary forces). The Teflon valve was then quickly replaced, and heating of the reaction mixture was continued. The sample taken with the Pasteur pipette was diluted with ethyl acetate (1 mL) and analyzed by GC. The results are compiled in FIG. 12, and represent averaged data from two runs.

EXAMPLE 89

Conversion of 5-iodo-m-xylene into 5-bromo-m-xylene

Two Schlenk tubes were charged with CuI (19.5 mg, 0.102 mmol, 5.0 mol %) and sodium bromide (206 mg, 2.00 mmol) or tetrabutylammonium bromide (645 mg, 2.00 mmol). The Schlenk tubes were evacuated and backfilled with argon. Racemic trans-N,N'-dimethyl-1,2-cyclohexanediamine (31.5 µL, 0.200 mmol, 10 mol %), 5-iodo-m-xylene (290 µL, 2.01 mmol), sec-butylbenzene (62 µL, internal GC standard), and DMF (2.0 mL) were added to each Schlenk tube. The reaction mixtures were stirred at 110° C. in an oil bath. After certain time intervals, the Schlenk tubes were briefly (ca. 1–2 min) removed from the oil bath, the Teflon valve was removed under a positive pressure of argon, and a sample (ca. 10–50 µL) was taken with a Pasteur pipette under a positive pressure of argon (the sample was drawn into the pipette by the capillary forces). The Teflon valve was then quickly replaced, and heating of the reaction mixture was continued. The sample taken with the Pasteur pipette was diluted with ethyl acetate (1 mL) and analyzed by GC. The results are compiled in FIG. 12, and represent averaged data from two runs.

EXAMPLE 90

Halogen Exchange Reaction Performed in a m-Xylene/Diglyme Solvent Mixture of Variable Composition (FIG. 13)

Nine Schlenk tubes were charged with CuI (9.6 mg, 0.050 mmol, 5.0 mol %), sodium iodide (300 mg, 2.00 mmol), evacuated and backfilled with argon. Racemic trans-N,N'-dimethyl-1,2-cyclohexanediamine (16 µL, 0.10 mmol, 10 mol %), 2-bromotoluene (121 µL, 1.01 mmol), m-xylene (0–1.0 mL), and diglyme (0–1.0 mL) were added to each Schlenk tube. The reaction mixtures were stirred at 130° C. for 15 h. The resulting suspensions were allowed to reach room temperature. Ethyl acetate (2 mL) and dodecane (230 µL, internal GC standard) were added to each reaction mixture. A 50 µL sample of the supernatant solution was diluted with ethyl acetate (1 mL) and analyzed by GC. The results are compiled in FIG. 13, and represent averaged data from two runs.

EXAMPLE 91

General Considerations for Copper-Catalyzed Conversion of Aryl Bromides into the Corresponding Cyanides Sodium cyanide (CAUTION: HIGHLY TOXIC) was purchased from Aldrich (97% pure). Copper(I) iodide (fine powder) was purchased from Strem (98% pure). If granulated CuI, available from other sources, is used instead, it may be necessary to grind it. CuI is air-stable and does not require any special precautions other than storage in an amber vial. N,N'-Dimethylethylenediamine was purchased from Aldrich. It forms a carbonate salt if exposed to air although we did not encounter any reproducibility problems even when using old samples of the diamine that had turned light brown and contained some precipitate. Potassium iodide (99.9% pure, powder) was purchased from Alfa Aesar and stored in a dessicator. Although KI and NaCN were weighed out in the air, care was taken to minimize exposure to air due to the hygroscopicity of the salts, particularly during very humid periods of the year. Toluene was purchased from J. T. Baker in CYCLE-TAINER solvent delivery kegs, which were purged with argon for 2 h and purified by passing the toluene through two packed columns of neutral alumina and copper (II) oxide under argon pressure. See Pangborn, A. B.; Giardello, M. A.; Grubbs, R. H.; Rosen, R. K.; Timmers, F. J. *Organometallics* 1996, 15, 1518–1520 and Alaimo, P. J.; Peters, D. W.; Arnold, J.; Bergman, R. G. *J. Chem. Ed.* 2001, 78, 64. All other reagents were commercially available and used without further purification. Flash column chromatography was performed with J. T. Baker silica gel 60 (230–400 mesh).

The copper-catalyzed cyanation reactions are sensitive to oxygen and moisture. Nevertheless, neither glovebox techniques nor purification of the commercially available reagents are required. The following procedure was used for the reactions that were performed in Schlenk tubes. After a 15 mL Schlenk tube with a screw thread (Kontes) was dried in an oven at 120° C. overnight, it was equipped with a 10×3 mm Teflon-coated stirring bar and a Teflon valve, evacuated, then backfilled with argon. The solid reagents were weighed out in the air by adding them directly to the Schlenk tube with the Teflon valve removed. The Schlenk tube was again fitted with the Teflon valve, evacuated and backfilled with argon. Under a positive pressure of argon, the Teflon valve was replaced with a rubber septum, and the liquid reagents were added to the Schlenk tube using Hamilton mycrosyringes (if <500 µL) or all polypropylene/polyethylene disposable syringes (if >500 µL). The rubber septum was replaced with a Teflon valve under positive pressure of argon. The Schlenk tube was sealed and heated in an oil bath for the specified time while stirring at the appropriate stirring rate. The stirring rate must be set carefully to avoid deposition of the solid on the walls of the Schlenk tube and to ensure at the same time an effective mixing. IR spectra were recorded on a Perkin-Elmer FT-IR 2000. Elemental analyses were performed by Atlantic Microlabs, Inc., Norcross, Ga. $^1$H NMR and $^{13}$C NMR spectra were recorded on a Bruker 400 MHz instrument with chemical shifts reported relative to residual deuterated solvent peaks or tetramethylsilane internal standard. Gas chromatographic analysis was performed on an Agilent 6890 instrument with an FID detector and an Agilent 10 m×0.10 μm i.d. HP-1 capillary column. Mass spectra (GC/MS) were recorded on a Hewlett Packard model GCD.

General Procedure for Copper-Catalyzed Conversion of Aryl Bromides into the Corresponding Cyanides A Schlenk tube was charged with NaCN (102 mg, 2.08 mmol), CuI (33 mg, 0.17 mmol, 10 mol %), aryl bromide (if it is a solid at room temperature; 1.74 mmol), and KI (57 mg, 0.34 mmol, 20 mol %). The tube was then briefly evacuated and backfilled with argon three times. Anhydrous toluene (1.2 mL), N,N'-dimethylethylenediamine (185 μL, 1.74 mmol), and aryl bromide (if it is a liquid at room temperature; 1.74 mmol) were added under argon. The Schlenk tube was sealed with a Teflon valve and the reaction mixture was stirred at 110° C. for 22–24 h. The resulting suspension was allowed to reach room temperature, diluted with 30% aq ammonia (3 mL), and extracted with ethyl acetate (4×2 mL). The combined organic phases were dried (MgSO$_4$ or Na$_2$SO$_4$), concentrated, and the residue was purified by flash chromatography on silica gel to provide the desired product.

EXAMPLE 92

3,5-Dimethylbenzonitrile

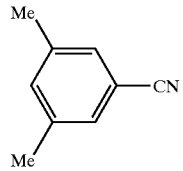

An oven dried 100 mL three necked round bottom flask was charged, under positive pressure of argon, with NaCN (2.04 g, 41.6 mmol) CuI (660 mg, 3.47 mmol, 10 mol %), KI (1.14 g, 6.87 mmol, 20 mol %), and anhydrous toluene (25 mL). N,N'-Dimethylethylenediamine (3.7 μL, 35 mmol) and 5-bromo-m-xylene (4.7 mL, 35 mmol) were added dropwise under mechanical stirring. The reaction mixture was stirred at 110° C. for 24 h. The resulting suspension was allowed to reach room temperature, diluted with 30% aq ammonia (20 mL) and extracted with toluene (2×10 mL). The combined organic phases were dried over MgSO$_4$, concentrated, and the residue was purified by distillation under reduced pressure (bp 100° C. @ 10 Torr) to provide the desired product as a white crystalline solid (4.08 g, 90% yield). Mp 42–43° C. (lit. 42.9° C., See Birch, S. F.; Dean, R. A.; Fidler, F. A.; Lowry, R. A. *J. Am. Chem. Soc.* 1949, 71, 1362). $^1$H NMR (400 MHz, CDCl$_3$; lit. See Nomura, Y.; Takeuchi, Y. *Tetrahedron* 1969, 25, 3825): δ 7.27 (s, 2H), 7.23 (s, 1H), 2.36 (s, 6H); $^{13}$C NMR (100 MHz, CDCl$_3$): 139.4, 135.0, 130.1, 119.7, 112.4, 21.5; IR (neat, cm$^{-1}$): 2230, 1605, 1378, 907, 854, 682. Anal. Calcd. for C$_9$H$_9$N: C, 82.41; H, 6.92; N, 10.68. Found: C, 82.1 1; H, 6.88; N, 10.52.

EXAMPLE 93

3,4-Dimethoxy-benzonitrile

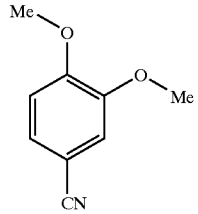

A Schlenk tube was charged with NaCN (204 mg, 4.16 mmol), CuI (66 mg, 0.35 mmol, 10 mol %), and KI (114 mg, 0.687 mmol, 20 mol %), briefly evacuated and backfilled with argon three times. Anhydrous toluene (2.4 mL), N,N'-dimethylethylenediamine (370 μL, 3.48 mmol), and 4-bromoveratrole (500 μL, 3.46 mmol) were added under argon. The Schlenk tube was sealed with a Teflon valve and the reaction mixture was stirred at 110° C. for 24 h. The resulting suspension was allowed to reach room temperature, diluted with 30% aq ammonia (2 mL), and extracted with ethyl acetate (4×4 mL). The combined organic phases were dried over MgSO$_4$, concentrated, and the residue was purified by distillation at reduced pressure (bp 160° C. @ 1 Torr) to provide the desired product as pale yellow solid (500 mg, 91% yield). Mp 60–62° C. (lit. 63.0–63.5° C., See Murahashi, S.-I.; Naota, T.; Nakajima, N. *J. Org. Chem.* 1986, 51, 898). $^1$H NMR (400 MHz, CDCl$_3$, J values are reported in Hz, lit. See Murahashi, S.-I.; Naota, T.; Nakajima, N. *J. Org. Chem.* 1986, 51, 898): δ 7.29 (dd, J=8.3, J=2.0, 1H), 7.08 (d, J=2.0, 1H), 6.91 (d, J=8.3, 1H), 3.94 (s, 3H), 3.91 (s, 3H); $^{13}$C NMR (100 MHz, CDCl$_3$): δ 153.2, 149.6, 126.9, 119.7, 114.3, 111.6, 104.3, 56.54, 56.51; IR (neat, cm$^{-1}$): 2225, 1598, 1583, 1519, 1245, 1158, 1139, 1018, 876, 811, 617. Anal. Calcd. for C$_9$H$_9$NO$_2$: C, 66.25; H, 5.56; N, 8.58. Found: C, 66.02; H, 5.72; N, 8.69.

EXAMPLE 94

Naphthalene-1-carbonitrile

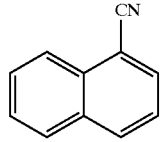

A Schlenk tube was charged with NaCN (95 mg, 1.94 mmol), CuI (31 mg, 0.16 mmol, 10 mol %), and KI (54 mg, 0.33 mmol, 20 mol %), briefly evacuated and backfilled with argon three times. Anhydrous toluene (1.2 mL), N,N'-dimethylethylenediamine (175 μL, 1.64 mmol), and 1-bromonaphthalene (225 μL, 1.62 mmol) were added under argon. The Schlenk tube was sealed with a Teflon valve and the reaction mixture was stirred at 130° C. for 24 h. The resulting suspension was allowed to reach room temperature, diluted with 30% aqueous ammonia (2 mL) and extracted with ethyl acetate (4×2 mL). The combined organic phases were dried over MgSO$_4$, concentrated, and the residue was purified by flash chromatography on silica gel (hexane/ethyl acetate 20:1) to provide the desired product as a pale yellow solid (234 mg, 94% yield). Mp 35–36° C. (lit. 37° C., See Blum, J.; Oppenheimer, E.; Bergmann, E.

J. Am. Chem. Soc. 1967, 89, 2338). $^1$H NMR (400 MHz, CDCl$_3$, J values are reported in Hz, lit. See Abraham, R. J.; Reid, M. Magn. Reson. Chem. 2000, 38, 570): δ 8.27 (d, J=8.4, 1H), 8.11 (d, J=8.3, 1H), 7.96 (d, J=8.1, 1H), 7.94 (dd, J=7.2, J=1.1, 1H), 7.73 (ddd, J=8.3, J=6.9, J=1.34, 1H), 7.65 (ddd, J=8.3, J=7.1, J=1.2, 1H), 7.55 (dd, J=8.3, J=7.1, 1H); $^{13}$C NMR (100 MHz, CDCl$_3$): 133.7, 133.2, 133.1, 132.8, 129.1, 129.0, 128.0, 125.6, 125.4, 118.3, 110.6; IR (neat, cm$^{-1}$): 2222, 1604, 1513, 1376, 855, 802, 772, 684, 451. Anal. Calcd. for C$_{11}$H$_7$N: C, 86.25; H, 4.61; N, 9.14. Found: C, 86.04; H, 4.61; N, 9.05.

EXAMPLE 95

Biphenyl-2-carbonitrile

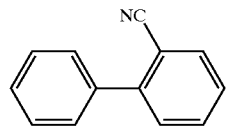

A Schlenk tube was charged with NaCN (98 mg, 2.0 mmol), CuI (31 mg, 0.16 mmol, 10 mol %), and KI (55 mg, 0.33 mmol, 20 mol %), briefly evacuated and backfilled with argon three times. Anhydrous toluene (1.2 mL), N,N'-dimethylethylenediamine (175 μL, 1.64 mmol), and 2-bromobiphenyl (285 μL, 1.65 mmol) were added under argon. The Schlenk tube was sealed with a Teflon valve and the reaction mixture was stirred at 130° C. for 24 h. The resulting suspension was allowed to reach room temperature, diluted with 30% aq ammonia (2 mL), and extracted with ethyl acetate (4×2 mL). The combined organic phases were dried over MgSO$_4$, concentrated, and the residue was purified by flash chromatography on silica gel (hexane-ethyl acetate 20:1) to provide the desired product as a light yellow oil which crystallized upon storing in a refrigerator (289 mg, 98% yield). Mp 34–37° C. (lit., 35–37° C. See Sain, B.; Sandhu, J. S. J. Org. Chem. 1990, 55, 2545). $^1$H NMR (400 MHz, CDCl$_3$, J values are reported in Hz, lit. See Hassan, J.; Hathroubi, C.; Gozzi, C.; Lemaire, M. Tetrahedron 2001, 57, 7845): δ 7.80 (ddd, J=7.8, J=1.5, J=0.5, 1H), 7.68 (td, J=7.8, J=1.3, 1H), 7.61–7.44 (m, 7H); $^{13}$C NMR (100 MHz, CDCl$_3$): 145.9, 138.6, 138.5, 134.2, 133.3, 130.5, 129.2, 129.1, 128.0, 119.2, 111.7; IR (neat, cm$^{-1}$): 2224, 1597, 1500, 1477, 1451, 1433, 759, 735, 700. Anal. Calcd. for C$_{13}$H$_9$N: C, 87.12; H, 5.06; N, 7.82. Found: C, 86.84; H, 5.22; N, 7.94.

EXAMPLE 96

4-Hydroxymethylbenzonitrile

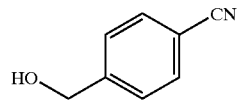

Following the general procedure in example 91, 4-bromophenylmethanol (325 mg, 1.74 mmol) was converted into 4-hydroxymethylbenzonitrile in 20 h at 110° C. Purification of the crude product by column chromatography on silica gel (hexane/ethyl acetate 2:1) provided the desired product as a white crystalline solid (190 mg, 83% yield). Mp 39–40° C. (lit. 39–41° C., See Yoon, N. M.; Pak, C. S.; Brown, H. C.; Krishnamurthy, S.; Stocky, T. P. J. Org. Chem. 1973, 38, 2786). $^1$H NMR (400 MHz, CDCl$_3$, J values are reported in Hz, lit. See Yoon, N. M.; Pak, C. S.; Brown, H. C.; Krishnamurthy, S.; Stocky, T. P. J. Org. Chem. 1973, 38, 2786): δ 7.66 (dt, J=8.1, J=1.8, 2H), 7.49 (d, J=8.1, 2H), 4.80 (s, 2H), 2.15 (bs, 1H); $^{13}$C NMR (100 MHz, CDCl$_3$): 146.6, 132.7, 127.4, 119.3, 111.5, 64.6; IR (neat, cm$^{-1}$): 3484, 2233, 1609, 1428, 1208, 1030, 847, 820, 566. Anal. Calcd. for C$_8$H$_7$NO: C, 72.16; H, 5.30; N, 10.52. Found: C, 72.15; H, 5.33; N, 10.44.

EXAMPLE 97

Ethyl 4-Cyanophenylacetate

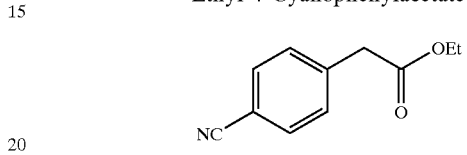

Following the general procedure in example 91, ethyl 4-bromophenylacetate (417 mg, 1.72 mmol) was converted into ethyl 4-cyanophenylacetate in 24 h at 130° C. Purification of the crude product by column chromatography on silica gel (hexane/ethyl acetate 10:1) provided the desired product as a fine white powder (230 mg, 70% yield). Mp 86–87° C. (lit. 87–88° C., See Norman, R. O. C.; Ralph, P. D. J. Chem. Soc. 1963, 5431). $^1$H NMR (400 MHz, CDCl$_3$, J values are reported in Hz, lit. See Beugelmans, R.; Bois-Choussy, M.; Boudet, B. Tetrahedron, 1982, 38, 3479): δ 7.63 (dt, J=8.2, J=1.8, 2H), 7.42 (d, J=8.2, 2H), 4.18 (q, J=7.0, 2H), 3.69 (s, 2H), 1.27 (t, J=7.0, 3H); $^{13}$C NMR (100 MHz, CDCl$_3$): δ 170.8, 139.9, 132.7, 130.6, 119.2, 111.5, 61.7, 41.7, 14.6; IR (neat, cm$^{-1}$): 2231, 1734, 1421, 1222, 1176, 1028. Anal. Calcd. for C$_{11}$H$_{11}$NO$_2$: C, 69.83; H, 5.86; N, 7.40. Found: C, 69.69; H, 5.93; N, 7.24.

EXAMPLE 98

2-Dimethylaminobenzonitrile

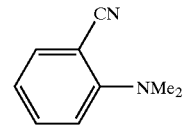

Following the general procedure in example 91, N,N-dimethyl-2-bromoaniline (250 μL, 1.75 mmol) was converted into 2-dimethylaminobenzonitrile in 24 h at 130° C. Purification of the crude product by column chromatography on silica gel (hexane/ethyl acetate 10:1) provided the desired product as a pale yellow oil (225 mg, 88% yield). $^1$H NMR (400 MHz, CDCl$_3$, J values are reported in Hz, lit. See Gupton, J. T.; Idoux, J. P.; Baker, G.; Colon, C.; Crews, A. D.; Jurss, C. D.; Rampi, R. C. J. Org. Chem. 1983, 48, 2933): δ 7.54 (ddd, J=7.7, J=1.7, J=1.0, 1H), 7.44 (ddd, J=9.00, J=7.3, J=1.7, 1H), 6.93 (bd, J=8.5, 1H), 6.87 (td, J=7.3, J=1.0, 1H); $^{13}$C NMR (100 MHz, CDCl$_3$): δ 155.7, 135.4, 133.9, 120.1, 119.6, 117.2, 101.7, 43.5; IR (neat, cm$^{-1}$): 2215, 1599, 1499, 1433, 948, 756.

EXAMPLE 99

N-(4-Cyano-2-fluorophenyl)acetamide

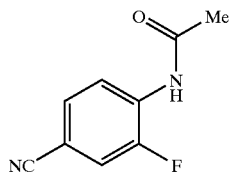

A Schlenk tube was charged with NaCN (137 mg, 2.80 mmol), CuI (44 mg, 0.23 mmol, 10 mol %), KI (77 mg, 0.46 mmol, 20 mol %), and N-(4-bromo-2-fluorophenyl)acetamide (540 mg, 2.33 mmol), briefly evacuated and backfilled with argon three times. Anhydrous toluene (1.2 mL) and N,N'-dimethylethylenediamine (250 μL, 2.35 mmol) were added under argon. The Schlenk tube was sealed with a Teflon valve and the reaction mixture was stirred at 110° C. for 24 h. The resulting suspension was allowed to reach room temperature, diluted with 30% aq ammonia (2 mL), and extracted with ethyl acetate (4×2 mL). The combined organic phases were dried over $MgSO_4$, concentrated, and the residue was purified by flash chromatography on silica gel (hexane/ethyl acetate 1:1) to provide the desired product as a fine white powder (337 mg, 87% yield). Mp 169.5–171.5° C.; $^1$H NMR (400 MHz, $CDCl_3$, J values are reported in Hz): δ 8.59 (t, J=8.4, 1H), 7.63 (bs, 1H), 7.48 (d, J=8.4, 1H), 7.41 (dd, J=10.6, J=1.8, 1H), 2.30 (s, 3H); $^{13}$C NMR (100 MHz, $CDCl_3$): 169.0, 151.3 (d, J=244 Hz), 131.6 (d, J=9.6 Hz), 129.9 (d, J=3.5 Hz), 121.9, 118.7 (d, J=22.8 Hz), 118.1 (d, J=2.9 Hz), 107.1 (d, J=9.3 Hz), 25.3; IR (neat, $cm^{-1}$): 3317, 2235, 1699, 1593, 1515, 834, 707. Anal. Calcd. for $C_9H_7FN_2O$: C, 60.67; H, 3.96; N, 15.72. Found: C, 60.42; H, 3.94; N, 15.63.

EXAMPLE 100

N-(2-Cyano-4-methylphenyl)acetamide

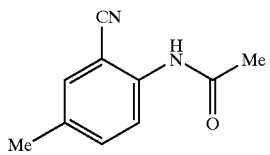

Following the general procedure in example 91, 2-bromo-4-methylacetanilide (395 mg, 1.74 mmol) was converted into N-(2-cyano-4-methylphenyl)acetamide in 24 h at 130° C. Purification of the crude product by column chromatography on silica gel (hexane/ethyl acetate 1:1) provided the desired product as a pale yellow crystalline powder (200 mg, 70% yield). Mp 133–135° C. $^1$H NMR (400 MHz, $CDCl_3$, J values are reported in Hz): δ 8.24 (d, J=8.3, 1H), 7.65 (bs, 1H), 7.40 (d, J=8.3, 1H), 7.39 (s, 1H), 2.34 (s, 3H), 2.26 (s, 3H); $^{13}$C NMR (100 MHz, $CDCl_3$): 169.0, 138.5, 135.4, 134.7, 132.6, 122.0, 117.0, 102.4, 25.1, 20.9; IR (neat, $cm^{-1}$): 3253, 2225, 1665, 1589, 1535, 1304, 1275, 1157, 828, 678, 497. Anal. Calcd. for $C_{10}H_{10}N_2O$: C, 68.95; H, 5.79; N, 16.08. Found: C, 69.10; H, 5.90; N, 15.97.

EXAMPLE 101

1H-Indole-5-carbonitrile

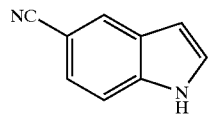

Following the general procedure in example 91, 5-bromoindole (340 mg, 1.74 mmol) was converted into 1H-indole-5-carbonitrile in 24 h at 110° C. Purification of the crude product by column chromatography on silica gel (hexane/ethyl acetate 6:1) provided the desired product as a light brown solid (190 mg, 80% yield). Mp 104–105° C. (lit. 104–106° C., See Lindwall, H. G.; Mantell, G. J. *J. Org. Chem.* 1953, 18, 345). $^1$H NMR (400 MHz, $CDCl_3$, J values are reported in Hz, lit. See Morales-Rios, M. S.; del Rio, R. E.; Joseph-Nathan, P. *Magn. Reson. Chem.* 1989, 27, 1039): δ 8.72 (bs, 1H), 8.03 (s, 1H), 7.50 (d, J=8.4, 1H), 7.45 (dd, J=8.4, J=1.5, 1H), 7.38 (t, J=2.8, 1H), 6.68–6.64 (m, 1H); $^{13}$C NMR (100 MHz, $CDCl_3$): δ 137.9, 128.1, 126.9, 126.8, 125.3, 121.3, 112.4, 103.9, 103.2; IR (neat, $cm^{-1}$): 3399, 2226, 1612, 1470, 1418, 1347, 1089, 894. Anal. Calcd. for $C_9H_6N_2$: C, 76.04; H, 4.25; N, 19.71. Found: C, 76.21; H, 4.28; N, 19.52.

EXAMPLE 102

Benzo[b]thiophene-3-carbonitrile

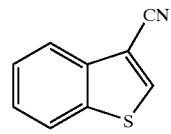

Following the general procedure in example 91, 3-bromothianaphthene (225 μL, 1.72 mmol) was converted into benzo[b]thiophene-3-carbonitrile in 24 h at 110° C. Purification of the crude product by column chromatography on silica gel (hexane/ethyl acetate 8:1) provided the desired product as a pale yellow solid (200 mg, 73% yield). Mp 67–69° C. (lit. 70–71° C., See Yoshida, K.; Miyoshi, K. *J. Chem. Soc., Perkin Trans.* 1 1992, 333). $^1$H NMR (400 MHz, $CDCl_3$, J values are reported in Hz, lit. See Yoshida, K.; Miyoshi, K. *J. Chem. Soc., Perkin Trans.* 1 1992, 333): δ 8.15 (s, 1H), 8.03 (d, J=7.8, 1H), 7.94 (d, J=7.8, 1H), 7.58 (td, J=8.1, J=1.0, 1H), 7.52 (dt, J=7.1, J=1.0, 1H); $^{13}$C NMR (100 MHz, $CDCl_3$): δ 138.9, 138.0, 137.7, 126.6, 126.4, 123.3, 122.9, 114.8, 107.5; IR (neat, $cm^{-1}$): 3108, 2224, 1462, 1426, 1256, 857, 814, 755, 729, 445. Anal. Calcd. for $C_9H_5NS$: C, 67.90; H, 3.17; N, 8.80. Found: C, 67.69; H, 3.11; N, 8.62.

EXAMPLE 103

Quinoline-3-carbonitrile

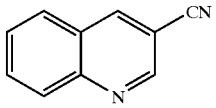

Following the general procedure in example 91, 3-bromoquinoline (235 μL, 1.73 mmol) was converted into quinoline-3-carbonitrile in 24 h at 110° C. Purification of the crude product by column chromatography on silica gel (hexane/ethyl acetate 6:1) provided the desired product as a white crystalline powder (205 mg, 75% yield). Mp 105–107° C. (lit. 105–107° C., lit. See Sakamoto, T.; Ohsawa, K. *J. Chem. Soc., Perkin Trans.* 1, 1999, 2323). $^1$H NMR (400 MHz, CDCl$_3$, J values are reported in Hz, lit. See Sakamoto, T.; Ohsawa, K. *J. Chem. Soc., Perkin Trans.* 1, 1999, 2323): δ 9.07 (d, J=2.0, 1H), 8.57 (dd, J=2.0, J=0.5, 1H), 8.20 (d, J=9.1, 1H), 7.95–7.90 (m, 2H), 7.73 (t, J=7.6, 1 H); $^{13}$C NMR (100 MHz, CDCl$_3$): δ 150.1, 149.2, 141.9, 133.2, 130.3, 128.9, 128.7, 126.6, 117.5, 107.0; IR (neat, cm$^{-1}$): 2229, 1619, 1597, 1489, 1370, 1130, 982, 961, 923, 739, 747, 638, 474. Anal. Calcd. for C$_{10}$H$_6$N$_2$: C, 77.91; H, 3.92; N, 18.17. Found: C, 77.96; H, 3.97; N, 18.32.

EXAMPLE 104

6-Aminonicotinonitrile

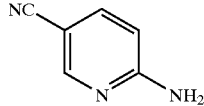

Following the general procedure in example 91, 2-amino-5-bromopyridine (294 mg, 1.70 mmol) was converted into 6-aminonicotinonitrile in 20 h at 110° C. Purification of the crude product by column chromatography on silica gel (hexane/ethyl acetate 2:5) provided the desired product as a white crystalline powder (180 mg, 90% yield). Mp 160–162° C. (lit. 161–162° C., lit. See Caldwell, W. T.; Tyson, F., T.; Lauer, L. *J. Am. Chem. Soc.* 1944, 66, 1479). $^1$H NMR (400 MHz, CDCl$_3$, J values are reported in Hz, lit. See Sundberg, R. J.; Biswas, S.; Murthi, K. K.; Rowe, D. *J. Med. Chem.* 1998, 41, 4317): δ 8.41–8.36 (m, 1H), 7.64 (dd, J=8.6, J=2.2, 1H), 6.53 (dd, J=8.6, J=0.9, 1H), 5.08 (bs, 2H); $^{13}$C NMR (100 MHz, CDCl$_3$): 160.5, 153.6, 140.7, 118.6, 108.4, 98.8; IR (neat, cm$^{-1}$): 3414, 3136, 2211, 1654, 1601, 1509, 1410, 832, 546. Anal. Calcd. for C$_6$H$_5$N$_3$: C, 60.50; H, 4.23; N, 35.27. Found: C, 60.37; H, 4.28; N, 35.31.

EXAMPLE 105

5-Bromo-1-(p-toluenesulfonyl)-1H-indole

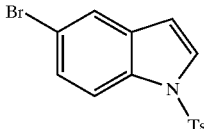

A 100 mL round bottom flask was sequentially charged with 5-bromoindole (1.96 g, 10 mmol), p-toluenesulfonyl chloride (2.30 g, 12 mmol), tetrabutylammonium hydrogen sulfate (240 mg, 0.70 mmol) and toluene (40 mL). An aqueous solution of potassium hydroxide (13 mL, 50%) was added dropwise and the mixture was stirred at room temperature overnight. At this point the organic layer was separated, diluted with ethyl ether (40 mL), washed with two portions of dilute potassium hydroxide solution (2×20 mL, 2M) and dried over MgSO$_4$. The solvent was removed at reduced pressure and the product was purified by flash chromatography on silica gel (hexane/ethyl acetate 1:1) to provide the desired product as a light yellow solid (3.50 g, 99% yield). M p 135° C. (lit. 139–140° C., See Fresneda, M. P.; Molina, P.; Bleda, A. J. *Tetrahedron* 2001, 57, 2355). $^1$H NMR (400 MHz, CDCl$_3$, J values are reported in Hz, lit. See Fresneda, M. P.; Molina, P.; Bleda, A. J. *Tetrahedron* 2001, 57, 2355): δ 7.88 (d, J=8.8, 1H), 7.76 (d, J=8.6, 2H), 7.68 (d, J=1.8, 1H), 7.59 (d, J=3.5, 1H), 7.42 (dd, J=8.8, J=2.0, 1H), 7.25 (d, J=8.6, 2H), 2.37 (s, 3H); $^{13}$C NMR (100 MHz, CDCl$_3$): δ 145.7, 135.3, 133.9, 132.9, 130.4, 128.0, 127.9, 127.2, 124.5, 117.2, 115.4, 108.7, 22.0.

EXAMPLE 106

1-(p-Toluenesulfonyl)-1H-indole-5-carbonitrile

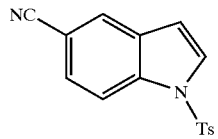

Following the general procedure in example 91, 5-bromo-1-(p-toluenesulfonyl)-1H-indole (607 mg, 1.73 mmol) was converted into 1-(p-toluenesulfonyl)-1H-indole-5-carbonitrile in 24 h at 110° C. Purification of the crude product by column chromatography on silica gel (hexane/ethyl acetate 6:1) provided the desired product as a white crystalline powder (475 mg, 93% yield). Mp 130–131° C. $^1$H NMR (400 MHz, CDCl$_3$, J values are reported in Hz): δ 8.09 (dt, J=8.7, J=0.8, 1H), 7.90 (d, J=1.6, 1H), 7.80 (dt, J=8.3, J=1.8, 2H), 7.72 (d, J=3.7, 1H), 7.58 (dd, J=8.7, J=1.7, 1H), 7.29 (d, J=8.3, 2H), 6.73 (dd, J=3.7, J=0.8, 1H), 2.39 (s, 3H); $^{13}$C NMR (100 MHz, CDCl$_3$): δ 146.2, 136.8, 135.1, 131.1, 130.6, 128.8, 128.0, 127.3, 126.8, 119.8, 114.7, 108.9, 107.3, 22.1; IR (neat, cm$^{-1}$): 2226, 1597, 1456, 1373, 1269, 1174, 1138, 672, 593, 540. Anal. Calcd. for C$_{16}$H$_{12}$N$_2$O$_2$S: C, 64.85; H, 4.08; N, 9.45. Found: C, 65.04; H, 4.11; N, 9.47.

EXAMPLE 107

1-Benzyl-4-bromo-1H-pyrazole

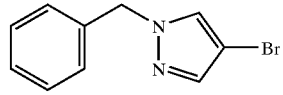

A 100 mL round bottom flask was charged with 4-bromopyrazole (4.41 g, 30 mmol), tetrabutylammonium bromide (484 mg, 1.5 mmol) and potassium hydroxide pellets (3.37 g, 60 mmol). After the mixture was sonicated for 15 min, benzyl chloride (5.2 mL, 45 mmol) was added dropwise and the resulting mixture was stirred overnight. Ethyl ether (20 mL), water (20 mL), and diluted hydrochloric acid (1 mL, 10%) were added under stirring. The organic layer was washed with water (2×20 mL) and dried over MgSO$_4$. The solvent was removed under reduced pressure and the product was purified by flash chromatography on silica gel (hexane/ethyl acetate 10:1) to provide the desired product as a white solid (6.74 g, 95% yield). Mp 51–52° C. (lit. 44–45° C., See Jones, R. G. *J. Am. Chem. Soc.* 1949, 71, 3994). $^1$H NMR (400 MHz, CDCl$_3$): δ 7.53 (s, 1H), 7.42–7.33 (m, 4H), 7.28–7.22 (m, 2H), 5.29 (s, 2H); $^{13}$C NMR (100 MHz, CDCl$_3$): δ 140.4, 136.2, 129.8, 129.4, 128.8, 128.3, 93.9, 57.1.

EXAMPLE 108

1-Benzyl-1H-pyrazole-4-carbonitrile

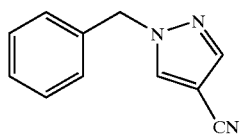

Following the general procedure in example 91, 1-benzyl-4-bromo-1H-pyrazole (308 mg, 1.74 mmol) was converted into 1-benzyl-1H-pyrazole-4-carbonitrile in 24 h at 110° C. Purification of the crude product by column chromatography on silica gel (hexane/ethyl acetate 5:1) provided the desired product as a light yellow solid (252 mg, 80% yield). Mp 61–63° C. $^1$H NMR (400 MHz, CDCl$_3$): δ 7.85 (s, 1H), 7.78 (s, 1H), 7.45–7.36 (m, 2H), 7.31–7.24 (m, 2H), 5.35 (s, 2H); $^{13}$C NMR (100 MHz, CDCl$_3$): 143.1, 134.8, 134.6, 129.6, 129.3, 128.5, 113.8, 93.1, 51.2; IR (neat, cm$^{-1}$): 3109, 2231, 1543, 1455, 1440, 1383, 1354, 1152, 1004, 991, 718, 693. Anal. Calcd. for C$_{11}$H$_9$N$_3$: C, 72.11; H, 4.95; N, 22.94. Found: C, 72.00; H, 4.92, N, 23.01.

EXAMPLE 109

Conversion of 5-Iodo-m-xylene into 3,5-Dimethylbenzonitrile Using Different Copper Precatalysts Three Schlenk tubes were charged with sodium cyanide (102 mg, 2.08 mmol) and either CuI (33 mg, 0.17 mmol, 10 mol %), CuBr (25 mg, 0.17 mmol, 10 mol %), or CuCN (15.5 mg, 0.173 mmol, 10 mol %). The Schlenk tubes were evacuated and backfilled with argon. Toluene (1.2 mL), N,N'-dimethylethylenediamine (185 µL, 1.74 mmol), and 5-iodo-m-xylene (250 µL, 1.73 mmol) were added to each Schlenk tube. The Schlenk tubes were sealed with Teflon valves, and the reaction mixtures were stirred at 90° C. in an oil bath for 24 h. The resulting suspensions were allowed to reach room temperature. Ethyl acetate (2 mL) and dodecane (internal GC standard, 200 µL) were added to the reaction mixtures. A 50 µL sample of the supernatant solution was diluted with ethyl acetate (1 mL) and analyzed by GC to provide the following results: CuI, 99.9% conversion of 5-iodo-m-xylene and 96% yield of 3,5-dimethylbenzonitrile; CuBr, 99.7% conversion of 5-iodo-m-xylene and 97% yield of 3,5-dimethylbenzonitrile; CuCN, >99.9% conversion of 5-iodo-m-xylene and 98% yield of 3,5-dimethylbenzonitrile.

EXAMPLE 110

Conversion of 5-Bromo-m-xylene into 3,5-Dimethylbenzonitrile Using Different Copper Precatalysts Three Schlenk tubes were charged with sodium cyanide (102 mg, 2.08 mmol) and either CuI (33 mg, 0.17 mmol, 10 mol %), CuBr (25 mg, 0.17 mmol, 10 mol %), or CuCN (15.5 mg, 0.173 mmol, 10 mol %). The Schlenk tubes were evacuated and backfilled with argon. Toluene (1.2 mL), N,N'-dimethylethylenediamine (185 µL, 1.74 mmol), and 5-bromo-m-xylene (235 µL, 1.73 mmol) were added to each Schlenk tube. The Schlenk tubes were sealed with Teflon valves, and the reaction mixtures were stirred at 110° C. in an oil bath for 24 h. The resulting suspensions were allowed to reach room temperature. Ethyl acetate (2 mL) and dodecane (internal GC standard, 200 µL) were added to the reaction mixtures. A 50 µL sample of the supernatant solution was diluted with ethyl acetate (1 mL) and analyzed by GC to provide the following results: CuI, 91% conversion of 5-bromo-m-xylene, 82% yield of 3,5-dimethylbenzonitrile, and 3% yield of 5-iodo-m-xylene; CuBr, 10% conversion of 5-bromo-m-xylene and 2% yield of 3,5-dimethylbenzonitrile; CuCN, 5% conversion of 5-bromo-m-xylene and 1% yield of 3,5-dimethylbenzonitrile.

Incorporation by Reference

All of the patents and publications cited in the Specification are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method represented by Scheme 1:

Scheme 1

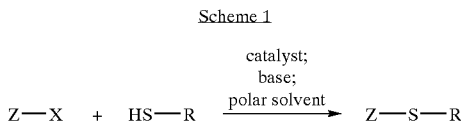

wherein

X represents I, Br, Cl, alkylsulfonate, or arylsulfonate;

Z represents optionally substituted aryl, heteroaryl, or alkenyl;

catalyst comprises a copper atom or ion;

base represents a Bronsted base; and

R represents optionally substituted alkyl, cycloalkyl, aryl, heteroaryl, aralkyl, heteroaralkyl, alkenylalkyl, or alkynylalkyl.

2. The method of claim 1, wherein X represents I.

3. The method of claim 1, wherein X represents Br.

4. The method of claim 1, wherein Z represents optionally substituted aryl.

5. The method of claim 1, wherein Z represents optionally substituted phenyl.

6. The method of claim 1, wherein the base is a carbonate, phosphate, oxide, hydroxide, alkoxide, aryloxide, amine, metal amide, fluoride, or guanidine.

7. The method of claim 1, wherein the base is potassium phosphate, potassium carbonate, cesium carbonate, sodium tert-butoxide, or sodium carbonate.

8. The method of claim 1, wherein X represents I; and Z represents optionally substituted aryl.

9. The method of claim 1, wherein X represents I; and Z represents optionally substituted phenyl.

10. The method of claim 1, wherein X represents I; Z represents optionally substituted aryl; and the base is a carbonate, phosphate, oxide, hydroxide, alkoxide, aryloxide, amine, metal amide, fluoride, or guanidine.

11. The method of claim 1, wherein X represents I; Z represents optionally substituted phenyl; and the base is a carbonate, phosphate, oxide, hydroxide, alkoxide, aryloxide, amine, metal amide, fluoride, or guanidine.

12. The method of claim 1, wherein X represents I; Z represents optionally substituted aryl; and the base is potassium phosphate, potassium carbonate, cesium carbonate, sodium tert-butoxide, or sodium carbonate.

13. The method of claim 1, wherein X represents I; Z represents optionally substituted phenyl; and the base is potassium phosphate, potassium carbonate, cesium carbonate, sodium tert-butoxide, or sodium carbonate.

14. The method of claim 1, wherein X represents Br; and Z represents optionally substituted aryl.

15. The method of claim 1, wherein X represents Br; and Z represents optionally substituted phenyl.

16. The method of claim 1, wherein X represents Br; Z represents optionally substituted aryl; and the base is a carbonate, phosphate, oxide, hydroxide, alkoxide, aryloxide, amine, metal amide, fluoride, or guanidine.

17. The method of claim 1, wherein X represents Br; Z represents optionally substituted phenyl; and the base is a carbonate, phosphate, oxide, hydroxide, alkoxide, aryloxide, amine, metal amide, fluoride, or guanidine.

18. The method of claim 1, wherein X represents Br; Z represents optionally substituted aryl; and the base is potassium phosphate, potassium carbonate, cesium carbonate, sodium tert-butoxide, or sodium carbonate.

19. The method of claim 1, wherein X represents Br; Z represents optionally substituted phenyl; and the base is potassium phosphate, potassium carbonate, cesium carbonate, sodium tert-butoxide, or sodium carbonate.

20. The method of any of claims 1–19, wherein the catalyst is present in less than or equal to about 10 mol % relative to Z—X.

21. The method of any of claims 1–19, wherein the catalyst is present in less than or equal to about 5 mol % relative to Z—X.

22. The method of any of claims 1–19, wherein the method is conducted at a temperature less than about 150 C.

23. The method of any of claims 1–19, wherein the method is conducted at a temperature less than about 100 C.

24. The method of any of claims 1–19, wherein the method is conducted at a temperature less than about 90 C.

25. The method of any of claims 1–19, wherein the method is conducted at a temperature less than about 85 C.

* * * * *

UNITED STATES PATENT AND TRADEMARK OFFICE
CERTIFICATE OF CORRECTION

PATENT NO. : 6,888,032 B2
APPLICATION NO. : 10/631480
DATED : May 3, 2005
INVENTOR(S) : Stephen L. Buchwald et al.

It is certified that error appears in the above-identified patent and that said Letters Patent is hereby corrected as shown below:

In column 1, lines 13-15, replace:

"This invention was made with support from the National Institutes of Health (grant number RO1-GM58160); therefore, the government has certain rights in the invention."

with

--This invention was made with government support under grant number R01 GM058160 awarded by the National Institutes of Health. The government has certain rights in this invention.--

Signed and Sealed this
Fifth Day of July, 2011

David J. Kappos
*Director of the United States Patent and Trademark Office*